(12) United States Patent
Lassner et al.

(10) Patent No.: US 7,157,619 B1
(45) Date of Patent: Jan. 2, 2007

(54) PLANT STEROL ACYLTRANSFERASES

(75) Inventors: Michael Lassner, Redwood City, CA (US); Alison Van Eenennaam, Davis, CA (US)

(73) Assignee: Monsanto Technology, L.L.C., St. Louis, MO (US)

( * ) Notice: Subject to any disclaimer, the term of this patent is extended or adjusted under 35 U.S.C. 154(b) by 947 days.

(21) Appl. No.: 09/651,651

(22) Filed: Aug. 30, 2000

Related U.S. Application Data

(60) Provisional application No. 60/152,493, filed on Aug. 30, 1999.

(51) Int. Cl.
| | |
|---|---|
| C12N 15/29 | (2006.01) |
| C12N 15/54 | (2006.01) |
| C12N 15/63 | (2006.01) |
| C12N 15/82 | (2006.01) |
| A01H 5/00 | (2006.01) |
| A01H 5/10 | (2006.01) |

(52) U.S. Cl. ............... 800/281; 800/287; 800/298; 435/419; 435/320.1; 536/23.1; 536/23.2; 536/23.6

(58) Field of Classification Search ............... 536/23.1, 536/23.2, 23.6; 435/320.1, 419; 800/278, 800/281, 287, 298
See application file for complete search history.

(56) References Cited

U.S. PATENT DOCUMENTS

| | | | |
|---|---|---|---|
| 4,588,717 | A | 5/1986 | Mitchell |
| 5,106,739 | A | 4/1992 | Comai et al. |
| 5,244,887 | A | 9/1993 | Straub |
| 5,270,041 | A | 12/1993 | Eugster et al. |
| 5,348,886 | A | 9/1994 | Lee et al. |
| 5,378,619 | A | 1/1995 | Rogers |
| 5,420,034 | A | 5/1995 | Kridl et al. |
| 5,593,874 | A | 1/1997 | Brown et al. |
| 5,608,152 | A | 3/1997 | Kridl et al. |
| 5,633,435 | A | 5/1997 | Barry et al. |
| 5,639,790 | A | 6/1997 | Voelker et al. |
| 5,693,507 | A | 12/1997 | Daniell |

FOREIGN PATENT DOCUMENTS

| | | |
|---|---|---|
| EP | 0 120 515 | 2/1990 |
| EP | 0 255 378 B1 | 4/1994 |
| WO | WO 96/38047 | 12/1996 |
| WO | WO 97/10328 | 3/1997 |
| WO | WO 97/42830 | 11/1997 |
| WO | WO 98/06405 | 2/1998 |
| WO | WO 98/06714 | 2/1998 |
| WO | WO 99/63096 A2 | 12/1999 |
| WO | WO 99/63096 A3 | 12/1999 |

OTHER PUBLICATIONS

Federspiel N. et al. Gene F21M11.5 as GenBank Accession No. AC003027 Dec. 30, 1998.*
Noiriel A. et al. European Journal of Biochemistry, 2004; vol. 271, pp. 3752-3764.*
Broun P. et al. Science vol. 282; Nov. 13, 1998, pp. 1315-1317.*
GenBank accession AC003027.*
Frentzen, Margrit; "Acyltransferases From Basic Science To Modified Seed Oils"; *Fett/Lipid*; vol. 100, No. 4/05; pp. 161-166; 1998.
Hobbs, Douglas H. et al.; "Cloning Of A cDNA Encoding Diacylglycerol Acyltransferase From *Arabidopsis thaliana* And Its Functional Expression"; *Febs Letters*; vol. 452; No. 3; pp. 145-149; 1999.
Nykiforuk, C.L. et al.; "Brassica Napus Putative Diacylglycerol Acyltransferase (DGAT1) mRNA"; XP002161573.
Taniyama Yoshio et al.; "Cloning And Expression Of A Novel Lysophospholipase Which Structurally Resembles Lecithin Cholesterol Acyltransferase"; *Biochemical and Biophysical Research Communications*; vol. 257; pp. 50-56; 1999.
Altschul et al., "Basic Local Alignment Search Tool", *J. Mole. Biol.*, Oct. 1990, pp. 403-410, vol. 215, No. 3, Academic Press, Great Britain.
Bechtold et al., "In planta *Agrobacterium* mediated gene transfer by infiltration of adult *Arabidopsis thaliana* plants", *Life Sciences*, Oct. 1993, pp. 1194-1199, vol. 316, No. 10, C.R. Acad, France.
Bent et al., RPS2 of *Arabidopsis thaliana*: A Leucine-Rich Repeat Class of Plant Disease Resistance Gene, *Science*, Sep. 1994, pp. 1856-1860, vol. 265, American Assoc. for the Advancement of Science, USA.
Chang et al., "Molecular Cloning and Functional Expression of Human Acyl-Coenzyme A:Cholesterol Acyltransferase cDNA in Mutant Chinese Hamster Ovary Cells", *Journal of Biological Chemisry*, Oct. 1993, pp. 20747-20755, vol. 268, Amer. Soc. Biochem. and Mol. Bio., USA.
Chang et al., "Acyl-Coenzyme A:Cholesterol Acyltransferase", *Annual Review of Biochemistry*, 1997, pp. 613-638, vol. 66, Annual Reviews Inc., USA.

(Continued)

*Primary Examiner*—Russell P. Kallis
(74) *Attorney, Agent, or Firm*—Fulbright & Jaworski L.L.P.

(57) ABSTRACT

The present invention is directed to lecithin:cholesterol acyltransferase-like polypeptides (LCAT) and acyl CoA: cholesterol acyltransferases-like polypeptides (ACAT). The invention provides polynucleotides encoding such cholesterol:acyltansferases-like polypeptides, polypeptides encoded by such polynucleotides, and the use of such polynucleotides to alter sterol composition and oil production in plants and host cells. Also provided are oils produced by the plants and host cells containing the polynucleotides and food products, nutritional supplements, and pharmaceutical composition containing plants or oils of the present invention. The polynucleotides of the present invention include those derived from plant sources.

25 Claims, 7 Drawing Sheets

OTHER PUBLICATIONS

Chen et al., "Functional analysis of regulatory elements in a plant embryo-specific gene", *Proceedings of the National Academy of Science*, Nov. 1986, pp. 8560-8564, vol. 83, No. 22, Natl. Acad. Sci., USA.

Coruzzi et al., Tissue specific and light-regulated expression of a pea nuclear gene encoding the small subunit of ribulose-1,5-bisphosphate carboxylase, *The EMBO Journal*, Aug. 1984, pp. 1671-1679, vol. 3, No. 8, IRL Press, Great Britain.

Coulson, "High-performance searching of biosequence databases", *Trends in Biotechnology*, Mar. 1994, pp. 76-80, vol. 12, No. 3, Elsevier Science Ltd.

Dahlqvist et al., "Phospholipid:diacyglycerol acyltransferase: An enzyme that catalyzes the acyl-CoA-independent formation of triacylglycerol in yeast and plants", *Proc. Natl. Acad. Sci.*, Jun. 2000, pp. 6487-6492, vol. 97, No. 12, Proc. Natl. Acad. Sci., USA.

Depicker et al., Nopaline Synthase: Transcript Mapping and DNA Sequence, *J. Mol. and Appl. Gene.*, 1982, pp. 561-573, vol. 1, No. 6, Raven Press, New York.

Devereux et al., A comprehensive set of sequence analysis programs for the VAX, *Nuc. Acids Res.*, Aug. 1983, pp. 387-395, IRL Press, Great Britain.

Ditta et al., "Broad host range DNA cloning system for Gram-negative bacteria: Construction of a gene bank of *Rhizobium meliloti*", *Proc. Natl. Acad. Sci.*, Dec. 1980, pp. 7347-7351, vol. 77, No. 12, Natl. Acad. Sci., USA.

Fling et al., "Nucleotide sequence of the transposon Tn7 gene encoding an aminoglycoside-modifying enzyme, 3"(9)-0-nucleotidyltransferase", *Nuc. Acids Res.*, May 1985, pp. 7095-7106, vol. 13, No. 19, IRL Press, Great Britain.

Frohman et al., "Rapid production of full-length cDNAs from rare transcripts: Amplification using a single gene-specific oligonucleotide primer", *Proc. Natl. Acad. Sci.*, Dec. 1988, pp. 8998-9002, vol. 85, No. 23, Natl. Acad. Sci., USA.

Goodwin, "Biosynthesis of Plant Sterols and Other Triterpenoids", *Biosynthesis of Isoprenoid Compounds*, 1981, pp. 444-480, vol. 1, John Wiley & Sons, USA.

Henikoff et al., "Amino acid substitution matrices from protein blocks", *Proc. Natl. Acad. Sci.*, Nov. 1992, pp. 10915-10919, vol. 89, No. 22, Natl. Acad. Sci., USA.

Holsters et al., Transfection and Transformation of *Agrobacterium tumefaciens*, Molec. Gen. Genet., 1978, pp. 181-187, vol. 163, Springer International.

Hood et al., "The Hypervirulence of *Agrobacterium tumefaciens* A281 Is Encoded in a Region of pTiBo542 Outside of T-DNA", *J. Bacter.*, Dec. 1986, pp. 1291-1301, vol. 168, No. 3, Amer. Soc. Micro., USA.

Jouanin et al., Localization and restriction maps of the replication origin regions of the plasmids of *Agrobacterium rhizogenes* strain A$_4$, *Molec. Gen. Genet.*, 1985, pp. 370-374, vol. 201, Springer International.

Klein et al., "Transformation of Microbes, Plants and Animals by Particle Bombardment", *Biotechnology*, Mar. 1992, pp. 286-291, vol. 10, No. 3, Nature Publishing Co., USA.

Kridl et al., Isolation and characterization of an expressed napin gene from *Brassica rapa*, *Seed Science Research*, Dec. 1991, pp. 209-219, vol. 1, No. 4, C.A.B. International, U.S.A.

Leisy et al., "Expression of a rice glutelin promoter in transgenic tobacco", *Plant Mol. Bio.*, 1989-90, pp. 41-50, vol. 14, Kluwer Academic Publishers, Belgium.

McBride et al., "Improved binary vectors for *Agrobacterium*-mediated plant transformation", *Plant Mol. Bio.*, Feb. 1990, pp. 269-276, vol. 14, No. 2, Kluwer Academic Publishers, Belgium.

McLean et al., "Human lecithin-cholesterol acyltransferase gene: complete gene sequence and sites of expression", *Nuc. Acids Res.*, Nov. 1986, pp. 9397-9406, vol. 14, No. 23, IRL Press, Great Britain.

Morelli et al., "A short conserved sequence is involved in the light-inducibility of a gene encoding ribulose 1,5-biophosphate carboxylase small subunit of pea", *Nature*, May 1985, pp. 200-204, vol. 315, No. 6016, Macmillan Journals, Ltd., Great Britain.

Napoli et al., Introduction of a Chimeric Chalcone Synthase Gene into Petunia Results in Reversible Co-Suppression of Homologous Genes in trans, *The Plant Cell*, Apr. 1990, pp. 279-289, vol. 2, Amer. Soc. of Plant Phys., USA.

Needleman et al., "A General Method Applicable to the Search for Similarities in the Amino Acid Sequence of Two Proteins", *J. Molec. Biol.*, Mar. 1970, pp. 443-453, vol. 48, Academic Press, Great Britain.

Oelkers et al., "A Lecithin Cholesterol Acyltransferase-like Gene Mediates Diacylglycerol Esterification in Yeast", *J. Bio. Chem.*, May 2000, pp. 15609-15612, vol. 275, No. 21, Amer. Soc. Biochem. and Mol. Biol., USA.

Radke et al., Transformation and regeneration of *Brassica rapa* using *Agrobacterium tumefaciens*, *Plant Cell Reports*, 1992, pp. 499-505, vol. 11, Springer-Verlag.

Radke et al., Transformation of *Brassica napus* L. using *Agrobacterium tumefaciens*: developmentally regulated expression of a reintroduced napin gene, *Theor. Appl. Genet.*, 1988, pp. 685-694, vol. 75, Springer-Verlag.

Schwender et al., "Biosynthesis of Sterols in Green Algae (*Scenedesmus, Chlorella*) According to a Novel, Mevalonate-Independent Pathway", *Phys., Bio. and Mol. Bio Plant Lipids*, 1997, pp. 180-182, Kluwer Academic Publishers, The Netherlands.

Smith et al., "Identification of Common Molecular Subsequences", *J. Mole. Bio.*, Mar. 1981, pp. 195-197, vol. 147, No. 1, Academic Press, Great Britain.

Smith et al., "Antisense RNA inhibition of polygalacturonase gene expression in transgenic tomatoes", *Nature*, Aug. 1988, pp. 725-726, vol. 334, No. 6184, Macmillan Magazines Ltd., Great Britain.

Svab et al., "Stable transformation of plastids in higher plants", *Proc. Natl. Acad. Sci.*, Nov. 1990, pp. 8526-8530, vol. 87, No. 21, Natl. Acad. Sci., USA.

Svab et al., "High-frequency plastid transformation in tobacco by selection for a chimeric aadA gene", *Proc. Natl. Acad. Sci.*, Feb. 1993, pp. 913-917, vol. 90, No. 3, Natl. Acad. Sci., USA.

Uelemen et al., "Tissue-specific Expression and Cholesterol Regulation of Acylcoenzyme A: Cholesterol Acyltransferase (ACAT) in Mice", *J. Biol. Chem.*, Nov. 1995, pp. 16192-16201, vol. 270, No. 44, Amer. Soc. Biochem. and Mol. Biol., USA.

Valvekens et al., "*Agrobacterium tumefaciens*-mediated transformation of *Arabidopsis thaliana* root explants by using kanamycin selection", *Proc. Natl. Acad. Sci.*, Aug. 1988, pp. 5536-5540, vol. 85, No. 15, Natl. Acad. Sci., USA.

Waterhouse et al., "Virus resistance and gene silencing in plants can be induced by simultaneous expression of sense and antisense RNA", *Proc. Natl. Acad. Sci.*, Nov. 1998, pp. 13959-13964, vol. 95, No. 23, Natl. Acad. Sci., USA.

Webb et al., "DNA Extraction from a Previously Recalcitrant Plant Genus", *Plant Mole. Bio. Rep.*, Aug. 1990, pp. 180-185, vol. VIII, No. 3, Inter. Soc. Plant Mole. Bio., USA.

Yang et al., "Sterol Esterification in Yeast: A Two-Gene Process", *Science*, May 1996, pp. 1353-1356, vol. 272, Amer. Assoc. Adv. Sci., USA.

Yu et al., "Molecular Cloning and Characterization of Two Isoforms of *Saccharomyces cerevisiae* Acyl-CoA:Sterol Acyltransferase", *J. Bio. Chem.*, Sep. 1996, pp. 24157-24163, vol. 271, No. 39, Amer. Soc. Biochem. and Mol. Bio., USA.

\* cited by examiner

FIG. 1A

ClustalW Formatted Alignments

```
                        10         20         30         40         50
Yeast (YNR008W) MGTLFRRNVQNQKSDSDENNKGGSVHNKRESRNHIHHQQLGHKRRRGIS
Human LCAT
AtLCAT1
AtLCAT2
AtLCAT3
AtLCAT4

60         70         80         90        100
Yeast (YNR008W) GSAKRNERGKDFDRKRDGNGRKRWRDSRRLIFTLGAFLCVLLPFSFGAYH
Human LCAT                                       LLLGLLLPPAPHWLLNVL
AtLCAT1                           MKK...........ISSHYSVVIALVVTMTS
AtLCAT2                                       SVTASFTVIAVFELICGR
AtLCAT3                      MGANSK...........LEEITRSVEALLKLRN
AtLCAT4                      MSL..............MGWLPCPCWGTNDD
                                                       A   F    N 110        120        130        140        150
Yeast (YNR008W) VHNSDSDLFDNFVNFPDSLKVYLDDWKDVLPQQISSFIDDIQAGNYSTSSL
Human LCAT      FPPHTIPKAELSN.........HTRPAVLVPGCL.
AtLCAT1         NCQAVGSNVY..........SKLSGIIPGFA.
AtLCAT2         TAVEDETEPHGDY.........FLIDVRCNG.
AtLCAT3         QEPYVDPNLN............PVLVPGIA.
AtLCAT4         ENAGEVADRD............PVLIVPGIG.
                                         PVILVPG
```

FIG. 1B

*[Sequence alignment figure showing protein sequence alignment of Yeast (YNR008W), Human LCAT, AtLCAT1, AtLCAT2, AtLCAT3, and AtLCAT4 across residues approximately 160-300]*

FIG. 1C

PLANT STEROL ACYLTRANSFERASES

CROSS-REFERENCE TO RELATED APPLICATIONS

This application claims priority to U.S. provisional application Ser. No. 60/152,493, filed Aug. 30, 1999 and herein incorporated by reference in its entirety for all purposes.

BACKGROUND

1. Technical Field

The present invention is directed to plant acyltransferase-like nucleic acid and amino acid sequences and constructs, and methods related to their use in altering sterol composition and/or content, and oil composition and/or content in host cells and plants.

2. Related Art

Through the development of plant genetic engineering techniques, it is now possible to produce transgenic varieties of plant species to provide plants which have novel and desirable characteristics. For example, it is now possible to genetically engineer plants for tolerance to environmental stresses, such as resistance to pathogens and tolerance to herbicides. It is also possible to improve the nutritional characteristics of the plant, for example to provide improved fatty acid, carotenoid, sterol and tocopherol compositions. However, the number of useful nucleotide sequences for the engineering of such characteristics is thus far limited.

There is a need for improved means to obtain or manipulate compositions of sterols from biosynthetic or natural plant sources. The ability to increase sterol production or alter the sterol compositions in plants may provide for novel sources of sterols for use in human and animal nutrition.

Sterol biosynthesis branches from the farnesyl diphosphate intermediate in the isoprenoid pathway. Sterol biosynthesis occurs via a mevalonate dependent pathway in mammals and higher plants (Goodwin,(1981) *Biosynthesis of Isoprenoid Compounds*, vol 1 (Porter, J. W. & Spurgeon, S. L., eds) pp. 443–480, John Wiley and Sons, New York), while in green algae sterol biosynthesis is thought to occur via a mevalonate independent pathway (Schwender, et al. (1997) *Physiology, Biochemistry, and Molecular Biology of Plant Lipids*, (Williams, J. P., Khan, M. U., and Lem, N. W., eds) pp. 180–182, Kluwer Academic Publishers, Norwell, MA).

The solubility characteristics of sterol esters suggests that this is the storage form of sterols (Chang, et al., (1997) *Annu. Rev. Biochem.*, 66:613–638). Sterol O-acyltransferase enzymes such as acyl CoA:cholesterol acyltransferase (ACAT) and lecithin:cholesterol acyltransferase (LCAT) catalyze the formation of cholesterol esters, and thus are key to controlling the intracellular cholesterol storage. In yeast, it has been reported that overexpression of LRO1, a homolog of human LCAT, and phospholipid:diacylglycerol acyltransferase increased lipid synthesis (Oelkers et al., (2000) *J. Biol. Chem.*, 26:15609–15612; Dahlqvist et al., (2000) *Proc. Natl. Acad. Sci. USA*, 97:6487–6492).

The characterization of various acyltransferase proteins is useful for the further study of plant sterol synthesis systems and for the development of novel and/or alternative sterol sources. Studies of plant mechanisms may provide means to further enhance, control, modify, or otherwise alter the sterol composition of plant cells. Furthermore, such alterations in sterol content and/or composition may provide a means for obtaining tolerance to stress and insect damage. Of particular interest are the nucleic acid sequences of genes encoding proteins which may be useful for applications in genetic engineering.

SUMMARY OF THE INVENTION

The present invention is directed to lecithin:cholesterol acyltransferase-like polypeptides (also referred to herein as LCAT) and acyl CoA:cholesterol acyltransferase-like polypeptides (also referred to herein as ACAT). In particular the invention is related to polynucleotides encoding such sterol:acyltransferases, polypeptides encoded by such polynucleotides, and the use of such polynucleotides to alter sterol composition and oil production. The polynucleotides of the present invention include those derived from plant sources.

One aspect of the invention, therefore, is an isolated nucleic acid sequence encoding a plant lecithin:cholesterol acyltransferase-like polypeptide, a fragment of a plant lecithin:cholesterol acyltransferase-like polypeptide, a plant acyl CoA:cholesterol acyltransferase-like polypeptide or a fragment of a plant acyl CoA:cholesterol acyltransferase-like polypeptide.

Another aspect provides an isolated nucleic acid sequence consisting essentially of SEQ ID NO: 2, 4, 6, 8, 10–29, 43–51, 73 or 75. Also provided is an isolated nucleic acid sequence consisting of SEQ ID NO: 2, 4, 6, 8, 10–29, 43–51, 73 or 75.

Still another aspect provides an isolated nucleic acid sequence comprising a polynucleotide selected from the group consisting of an isolated polynucleotide encoding a polypeptide of SEQ ID NO: 3 or SEQ ID NO: 3 with at least one conservative amino acid substitution; SEQ ID NO: 2; an isolated polynucleotide that has at least 70%, 80%, 90%, or 95% sequence identity with SEQ ID NO: 2; an isolated polynucleotide of at least 10 amino acids that hybridizes under stringent conditions to SEQ ID NO: 2; an isolated polynucleotide complementary to any of the foregoing; and an isolated polynucleotide that hybridizes under stringent conditions to SEQ ID NO: 2 and encodes a plant lecithin:cholesterol acyltransferase-like polypeptide.

Still another aspect provides an isolated nucleic acid sequence consisting essentially of a polynucleotide of the formula 5' X—$(R_1)n$—$(R_2)n$—$(R_3)n$—Y 3' where X is a hydrogen, Y is a hydrogen or a metal, $R_1$ and $R_3$ are any nucleic acid, n is an integer between 0–3000, and $R_2$ is selected from the group consisting of an isolated polynucleotide encoding a polypeptide of SEQ ID NO: 3 or SEQ ID NO: 3 with at least one conservative amino acid substitution; SEQ ID NO: 2; an isolated polynucleotide that has at least 70%, 80%, 90%, or 95% sequence identity with SEQ ID NO: 2; an isolated polynucleotide of at least 10 amino acids that hybridizes under stringent conditions to SEQ ID NO: 2; an isolated polynucleotide complementary to any of the foregoing; and an isolated polynucleotide that hybridizes under stringent conditions to SEQ ID NO: 2 and encodes a plant lecithin:cholesterol acyltransferase-like polypeptide.

Another aspect provides an isolated nucleic acid sequence comprising a polynucleotide selected from the group consisting of an isolated polynucleotide encoding a polypeptide of SEQ ID NO:5 or SEQ ID NO: 5 with at least one conservative amino acid substitution; SEQ ID NO: 4; an isolated polynucleotide that has at least 70%, 80%, 90%, or 95% sequence identity with SEQ ID NO: 4; an isolated polynucleotide of at least 10 amino acids that hybridizes under stringent conditions to SEQ ID NO: 4; an isolated polynucleotide complementary to any of the foregoing; and an isolated polynucleotide that hybridizes under stringent conditions to SEQ ID NO: 4 and encodes a plant lecithin:cholesterol acyltransferase-like polypeptide.

Another aspect provides an isolated nucleic acid sequence consisting essentially of a polynucleotide of the formula 5' X—($R_1$)n—($R_2$)n—($R_3$)n—Y 3' where X is a hydrogen, Y is a hydrogen or a metal, $R_1$ and $R_3$ are any nucleic acid, n is an integer between 0–3000, and $R_2$ is selected from the group consisting of an isolated polynucleotide encoding a polypeptide of SEQ ID NO: 5 or SEQ ID NO: 5 with at least one conservative amino acid substitution; SEQ ID NO: 4; an isolated polynucleotide that has at least 70%, 80%, 90%, or 95% sequence identity with SEQ ID NO: 4; an isolated polynucleotide of at least 10 amino acids that hybridizes under stringent conditions to SEQ ID NO: 4; an isolated polynucleotide complementary to any of the foregoing; and an isolated polynucleotide that hybridizes under stringent conditions to SEQ ID NO: 4 and encodes a plant lecithin:cholesterol acyltransferase-like polypeptide.

Another aspect provides an isolated nucleic acid sequence comprising a polynucleotide selected from the group consisting of an isolated polynucleotide encoding a polypeptide of SEQ ID NO:7 or SEQ ID NO: 7 with at least one conservative amino acid substitution; SEQ ID NO: 6; an isolated polynucleotide that has at least 70%, 80%, 90%, or 95% sequence identity with SEQ ID NO: 6; an isolated polynucleotide of at least 10 amino acids that hybridizes under stringent conditions to SEQ ID NO: 6; an isolated polynucleotide complementary to any of the foregoing; and an isolated polynucleotide that hybridizes under stringent conditions to SEQ ID NO: 6 and encodes a plant lecithin:cholesterol acyltransferase-like polypeptide.

Another aspect provides an isolated nucleic acid sequence consisting essentially of a polynucleotide of the formula 5' X—($R_1$)n—($R_2$)n—($R_3$)n—Y 3' where X is a hydrogen, Y is a hydrogen or a metal, $R_1$ and $R_3$ are any nucleic acid, n is an integer between 0–3000, and $R_2$ is selected from the group consisting of an isolated polynucleotide encoding a polypeptide of SEQ ID NO: 7 or SEQ ID NO: 7 with at least one conservative amino acid substitution; SEQ ID NO: 6; an isolated polynucleotide that has at least 70%, 80%, 90%, or 95% sequence identity with SEQ ID NO: 6; an isolated polynucleotide of at least 10 amino acids that hybridizes under stringent conditions to SEQ ID NO: 6; an isolated polynucleotide complementary to any of the foregoing; and an isolated polynucleotide that hybridizes under stringent conditions to SEQ ID NO: 6 and encodes a plant lecithin:cholesterol acyltransferase-like polypeptide.

Another aspect provides an isolated nucleic acid sequence comprising a polynucleotide selected from the group consisting of an isolated polynucleotide encoding a polypeptide of SEQ ID NO:9 or SEQ ID NO: 9 with at least one conservative amino acid substitution; SEQ ID NO: 8; an isolated polynucleotide that has at least 70%, 80%, 90%, or 95% sequence identity with SEQ ID NO: 8; an isolated polynucleotide of at least 10 amino acids that hybridizes under stringent conditions to SEQ ID NO: 8; an isolated polynucleotide complementary to any of the foregoing; and an isolated polynucleotide that hybridizes under stringent conditions to SEQ ID NO: 8 and encodes a plant lecithin:cholesterol acyltransferase-like polypeptide.

Another aspect provides an isolated nucleic acid sequence consisting essentially of a polynucleotide of the formula 5' X—($R_1$)n—($R_2$)n—($R_3$)n—Y 3' where X is a hydrogen, Y is a hydrogen or a metal, $R_1$ and $R_3$ are any nucleic acid, n is an integer between 0–3000, and $R_2$ is selected from the group consisting of an isolated polynucleotide encoding a polypeptide of SEQ ID NO: 9 or SEQ ID NO: 9 with at least one conservative amino acid substitution; SEQ ID NO:.8; an isolated polynucleotide that has at least 70%, 80%, 90%, or 95% sequence identity with SEQ ID NO: 8; an isolated polynucleotide of at least 10 amino acids that hybridizes under stringent conditions to SEQ ID NO: 8; an isolated polynucleotide complementary to any of the foregoing; and an isolated polynucleotide that hybridizes under stringent conditions to SEQ ID NO: 8 and encodes a plant lecithin:cholesterol acyltransferase-like polypeptide.

Another aspect provides an isolated nucleic acid sequence comprising a polynucleotide selected from the group consisting of an isolated polynucleotide encoding a polypeptide of SEQ ID NO:74 or SEQ ID NO: 74 with at least one conservative amino acid substitution; SEQ ID NO: 73; an isolated polynucleotide that has at least 70%, 80%, 90%, or 95% sequence identity with SEQ ID NO: 73; an isolated polynucleotide of at least 10 amino acids that hybridizes under stringent conditions to SEQ ID NO: 73; an isolated polynucleotide complementary to any of the foregoing; and an isolated polynucleotide that hybridizes under stringent conditions to SEQ ID NO: 73 and encodes a plant lecithin:cholesterol acyltransferase-like polypeptide.

Another aspect provides an isolated nucleic acid sequence consisting essentially of a polynucleotide of the formula 5' X—($R_1$)n—($R_2$)n—($R_3$)n—Y 3' where X is a hydrogen, Y is a hydrogen or a metal, $R_1$ and $R_3$ are any nucleic acid, n is an integer between 0–3000, and $R_2$ is selected from the group consisting of an isolated polynucleotide encoding a polypeptide of SEQ ID NO: 74 or SEQ ID NO: 74 with at least one conservative amino acid substitution; SEQ ID NO: 73; an isolated polynucleotide that has at least 70%, 80%, 90%, or 95% sequence identity with SEQ ID NO: 73; an isolated polynucleotide of at least 10 amino acids that hybridizes under stringent conditions to SEQ ID NO: 73; an isolated polynucleotide complementary to any of the foregoing; and an isolated polynucleotide that hybridizes under stringent conditions to SEQ ID NO: 73 and encodes a plant lecithin:cholesterol acyltransferase-like polypeptide.

Another aspect provides an isolated nucleic acid sequence comprising a polynucleotide selected from the group consisting of an isolated polynucleotide encoding a polypeptide of SEQ ID NO:76 or SEQ ID NO: 76 with at least one conservative amino acid substitution; SEQ ID NO: 75; an isolated polynucleotide that has at least 70%, 80%, 90%, or 95% sequence identity with SEQ ID NO: 75; an isolated polynucleotide of at least 10 amino acids that hybridizes under stringent conditions to SEQ ID NO: 75; an isolated polynucleotide complementary to any of the foregoing; and an isolated polynucleotide that hybridizes under stringent conditions to SEQ ID NO: 75 and encodes a plant lecithin:cholesterol acyltransferase-like polypeptide.

Another aspect provides an isolated nucleic acid sequence consisting essentially of a polynucleotide of the formula 5' X—($R_1$)n—($R_2$)n—($R_3$)n—Y 3' where X is a hydrogen, Y is a hydrogen or a metal, $R_1$ and $R_3$ are any nucleic acid, n is an integer between 0–3000, and $R_2$ is selected from the group consisting of an isolated polynucleotide encoding a polypeptide of SEQ ID NO: 76 or SEQ ID NO: 76 with at least one conservative acid substitution; SEQ ID NO: 75; an isolated polynucleotide that has at least 70%, 80%, 90%, or 95% sequence identity with SEQ ID NO: 75; an isolated polynucleotide of at least 10 amino acids that hybridizes under stringent conditions to SEQ ID NO: 75; an isolated polynucleotide complementary to any of the foregoing; and an isolated polynucleotide that hybridizes under stringent conditions to SEQ ID NO: 75 and encodes a plant lecithin: cholesterol acyltransferase-like polypeptide.

Another aspect provides an isolated nucleic acid sequence comprising a polynucleotide selected from the group consisting of SEQ ID NO: 42 or a degenerate variant thereof; an isolated polynucleotide that has at least 70%, 80%, 90%, or 95% sequence identity with SEQ ID NO: 42; an isolated polynucleotide of at least 10 amino acids that hybridizes under stringent conditions to SEQ ID NO: 42; an isolated polynucleotide complementary to any of the foregoing; and an isolated polynucleotide that hybridizes under stringent conditions to SEQ ID NO: 42 and encodes an acyl CoA: cholesterol acyltransferase-like polypeptide.

Another aspect provides an isolated nucleic acid sequence consisting essentially of 30 a polynucleotide of the formula 5' X—$(R_1)$n—$(R_2)$n—$(R_3)$n—Y 3' where X is a hydrogen, Y is a hydrogen or a metal, $R_1$ and $R_3$ are any nucleic acid, n is an integer between 0–3000, and $R_2$ is selected from the group consisting of SEQ ID NO: 42 or a degenerate variant thereof, an isolated polynucleotide that has at least 70%, 80%, 90%, or 95% sequence identity with SEQ ID NO: 42; an isolated polynucleotide of at least 10 amino acids that hybridizes under stringent conditions to SEQ ID NO: 42; an isolated polynucleotide complementary to any of the foregoing; and an isolated polynucleotide that hybridizes under stringent conditions to SEQ ID NO: 42 and encodes a acyl CoA:cholesterol acyltransferase-like polypeptide.

Also provided is a recombinant nucleic acid construct comprising a regulatory sequence operably linked to a polynucleotide encoding a lecithin:cholesterol acyltransferase-like polypeptide and/or an acyl CoA:cholesterol acyltransferase-like polypeptide. In one embodiment, the sterol acyl transferases are plant sterol acyl transferases. In another embodiment, the recombinant nucleic acid constructs further comprises a termination sequence. The regulatory sequence can be a constitutive promoter, an inducible promoter, a developmentally regulated promoter, a tissue specific promoter, an organelle specific promoter, a seed specific promoter or a combination of any of the foregoing. Also provided is a plant containing this recombinant nucleic acid construct and the seed and progeny from such a plant. This recombinant nucleic acid construct can also be introduced into a suitable host cell to provide yet another aspect of the invention. If the host cell is a plant host cell, the cell can be used to generate a plant to provide another aspect of the invention. Further aspects include seed and progeny from such a plant.

Yet another aspect is a purified polypeptide comprising, SEQ ID NO: 3, SEQ ID NO: 5, SEQ ID NO: 7, SEQ ID NO: 9, SEQ ID NO: 74, SEQ ID NO: 76, or any of the preceding sequences with at least one conservative amino acid substitution.

Still another aspect provides a purified immunogenic polypeptide comprising at least 10 consecutive amino acids from an amino acid sequence selected from the group consisting of SEQ ID NO: 3, 5, 7, 9, 74, 76 and any of the preceding sequences containing at least one conservative amino acid substitution. Also provided are antibodies, either polyclonal or monoclonal, that specifically bind the preceding immunogenic polypeptides.

One aspect provides a method for producing a lecithin: cholesterol acyltransferase-like polypeptide or an acyl CoA: cholesterol acyltransferase-like polypeptide comprising culturing a host cell containing any recombinant nucleic acid construct of the present invention under condition permitting expression of said lecithin:cholesterol acyltransferase-like polypeptide or acyl CoA:cholesterol acyltransferase-like polypeptide.

Another aspect provides a method for modifying the sterol content of a host cell, comprising transforming a host cell with a recombinant construct containing a regulatory sequence operably linked to a polynucleotide encoding a lecithin:cholesterol acyltransferase-like polypeptide and culturing said host cell under conditions wherein said host cell expresses a lecithin:cholesterol acyltransferase-like polypeptide such that said host cell has a modified sterol composition as compared to host cells without the recombinant construct.

An additional aspect is a method for modifying the sterol content of a host cell comprising transforming a host cell with a recombinant construct containing a regulatory sequence operably linked to a polynucleotide encoding an acyl CoA:cholesterol acyltransferase-like polypeptide and culturing said host cell under conditions wherein said host cell expresses an acyl CoA:cholesterol acyltransferase-like polypeptide such that said host cell has a modified sterol composition as compared to host cells without the recombinant construct.

A further aspect is a plant comprising a recombinant construct containing a regulatory sequence operably linked to a polynucleotide encoding a lecithin:cholesterol acyltransferase-like polypeptide wherein expression of said recombinant construct results in modified sterol composition of said plant as compared to the same plant without said recombinant construct.

Another aspect provides a plant comprising a recombinant construct containing a regulatory sequence operably linked to a polynucleotide encoding an acyl CoA:cholesterol acyltransferase-like polypeptide wherein expression of said recombinant construct results in modified sterol composition of said plant as compared to the same plant without said recombinant construct.

In a further aspect is provided an oil obtained from any of the plants or host cells of the present invention.

In still another aspect is provided a method for producing an oil with a modified sterol composition comprising providing any of the plants or host cells of the present invention and extracting oil from the plant by any known method. Also provided is an oil produced by the preceding method.

Still another aspect provides a method for altering oil production by a host cell comprising, transforming a host cell with a recombinant construct containing a regulatory sequence operably linked to a polynucleotide encoding a lecithin:cholesterol acyltransferase-like polypeptide and culturing the host cell under conditions wherein the host cell expresses a lecithin:cholesterol acyltransferase-like polypeptide such that the host cell has an altered oil production as compared to host cells without the recombinant construct.

Another aspect provides a method for altering oil production by a host cell comprising, transforming a host cell with a recombinant construct containing a regulatory sequence operably linked to a polynucleotide encoding an acyl CoA: cholesterol acyltransferase-like polypeptide and culturing the host cell under conditions wherein the host cell expresses an acyl CoA:cholesterol acyltransferase-like polypeptide such that the host cell has an altered oil production as compared to host cells without the recombinant construct.

Also provided is a plant comprising a recombinant construct containing a regulatory sequence operably linked to a polynucleotide encoding a lecithin:cholesterol acyltransferase-like polypeptide wherein expression of said recombinant construct results in an altered production of oil by said plant as compared to the same plant without said recombinant construct.

In a further aspect is provided a plant comprising a recombinant construct containing a regulatory sequence operably linked to a polynucleotide encoding an acyl CoA:cholesterol acyltransferase-like polypeptide wherein expression of said recombinant construct results in an altered production of oil by said plant as compared to the same plant without said recombinant construct.

Additional aspects provide a food, food ingredient or food product comprising any oil, plant or host cell of the present invention; a nutritional or dietary supplement comprising any oil, plant or host cell of the present invention; and a pharmaceutical composition comprising any oil, plant or host cell of the present invention along with a suitable diluent, carrier or excipient.

Additional aspects will be apparent from the descriptions and examples that follow.

BRIEF DESCRIPTION OF THE DRAWINGS

These and other features, aspects, and advantages of the present invention will become better understood with regard to the following description, appended claims and accompanying figures where:

FIG. 1 shows an alignment of yeast (SEQ ID NO: 76), and human (SEQ ID NO:1) lecithin:cholesterol acyltransferase protein sequences with *Arabidopsis* LCAT1 (SEQ ID NO: 3), LCAT2 (SEQ ID NO: 5), LCAT3 (SEQ ID NO: 7), and LCAT4 (SEQ ID NO: 9) deduced amino acid sequences.

DETAILED DESCRIPTION

Figure 2:
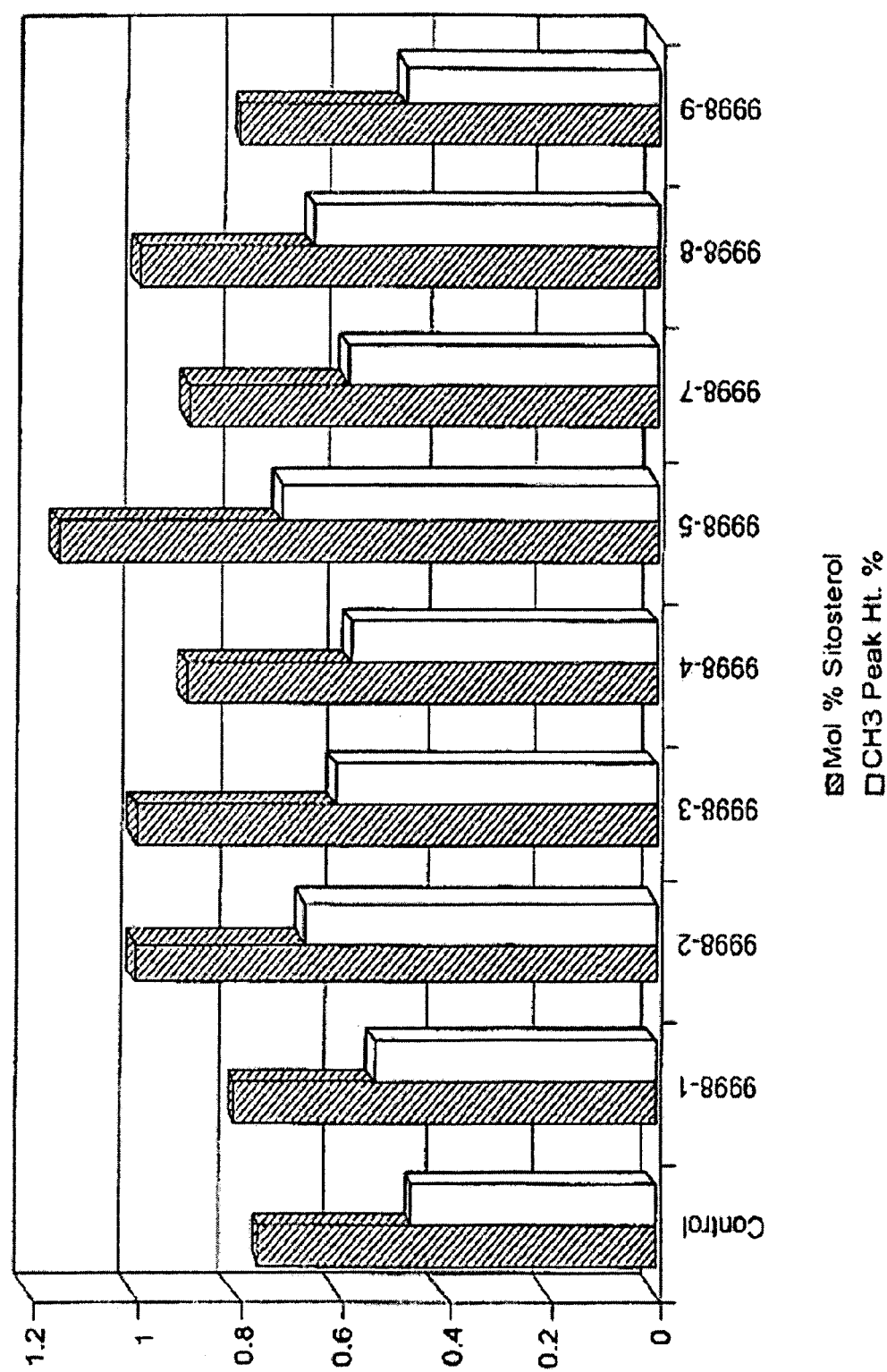
FIG. 2 shows the results of NMR sterol ester analysis on T2 seed from plant expressing LCAT4 under the control of the napin promoter (pCGN9998).

The following detailed description is provided to aid those skilled in the art in practicing the present invention. Even so, this detailed description should not be construed to unduly limit the present invention as modifications and variations in the embodiments discussed herein can be made by those of ordinary skill in the art without departing from the spirit or scope of the present inventive discovery.

All publications, patents, patent applications and other references cited in this application are herein incorporated by reference in their entirety as if each individual publication, patent, patent application or other reference were specifically and individually indicated to be incorporated by reference.

The present invention relates to lecithin:cholesterol acyltransferase, particularly the isolated nucleic acid sequences encoding lecithin:cholesterol-like polypeptides (LCAT) from plant sources and acyl CoA:cholesterol:acyltransferase, particularly the isolated nucleic acid sequences encoding acyl CoA:cholesterol acyltransferase-like polypeptides (ACAT) from plant sources. Lecithin:cholesterol acyltransferase-like as used herein includes any nucleic acid sequence encoding an amino acid sequence from a plant source, such as a protein, polypeptide or peptide, obtainable from a cell source, which demonstrates the ability to utilize lecithin (phosphatidyl choline) as an acyl donor for acylation of sterols or glycerides to form esters under enzyme reactive conditions along with such proteins polypeptides and peptides. Acyl CoA:cholesterol acyltransferase-like as used herein includes any nucleic acid sequence encoding an amino acid sequence from a plant source, such as a protein, polypeptide or peptide, obtainable from a cell source, which demonstrates the ability to utilize acyl CoA as an acyl donor for acylation of sterols or glycerides to form esters under enzyme reactive conditions along with such proteins polypeptides and peptides. By "enzyme reactive conditions" is meant that any necessary conditions are available in an environment (i.e., such factors as temperature, pH, lack of inhibiting substances) which will permit the enzyme to function.

The term "sterol" as applied to plants refers to any chiral tetracyclic isopentenoid which may be formed by cyclization of squalene oxide through the transition state possessing stereochemistry similar to the trans-syn-trans-anti-trans-anti configuration, for example, protosteroid cation, and which retains a polar group at C-3 (hydroxyl or keto), an all-trans-anti stereochemistry in the ring system, and a side-chain 20R-configuration (Parker, et al. (1992) In Nes, et al., Eds., *Regulation of Isopentenoid Metabolism*, ACS Symposium Series No. 497, p. 110; American Chemical Society, Washington, D.C.).

Sterols may or may not contain a C-5-C-6 double bond, as this is a feature introduced late in the biosynthetic pathway. Sterols contain a $C_8$–$C_{10}$ side chain at the C-17 position.

The term "phytosterol," which applies to sterols found uniquely in plants, refers to a sterol containing a C-5, and in some cases a C-22, double bond. Phytosterols are further characterized by alkylation of the C-17 side-chain with a methyl or ethyl substituent at the C-24 position. Major phytosterols include, but are not limited to, sitosterol, stigmasterol, campesterol, brassicasterol, etc. Cholesterol, which lacks a C-24 methyl or ethyl side-chain, is found in plants, but is not unique thereto, and is not a "phytosterol."

"Phytostanols" are saturated forms of phytosterols wherein the C-5 and, when present, C-22 double bond(s) is (are) reduced, and include, but are not limited to, sitostanol, campestanol, and 22-dihydrobrassicastanol.

"Sterol esters" are further characterized by the presence of a fatty acid or phenolic acid moiety rather than a hydroxyl group at the C-3 position.

The term "sterol" includes sterols, phytosterols, phytosterol esters, phytostanols, and phytostanol esters.

The term "sterol compounds" includes sterols, phyotsterols, phytosterol esters, phytostanols, and phytostanol esters.

The term "phytosterol compound" refers to at least one phytosterol, at least one phytosterol ester, or a mixture thereof.

The term "phytostanol compound" refers to at least one phytostanol, at least one phytostanol ester, or a mixture thereof.

The term "glyceride" refers to a fatty acid ester of glycerol and includes mono-, di-, and tri-acylglycerols.

As used herein, "recombinant construct" is defined either by its method of production or its structure. In reference to its method of production, e.g., a product made by a process, the process is use of recombinant nucleic acid techniques, e.g., involving human intervention in the nucleotide sequence, typically selection or production. Alternatively, in terms of structure, it can be a sequence comprising fusion of two or more nucleic acid sequences which are not naturally contiguous or operatively linked to each other As used herein, "regulatory sequence" means a sequence of DNA concerned with controlling expression of a gene; e.g. promoters, operators and attenuators. A "heterologous regulatory sequence" is one which differs from the regulatory sequence naturally associated with a gene.

As used herein, "polynucleotide" and "oligonucleotide" are used interchangeably and mean a polymer of at least two nucleotides joined together by a phosphodiester bond and may consist of either ribonucleotides or deoxynucleotides.

As used herein, "sequence" means the linear order in which monomers appear in a polymer, for example, the order of amino acids in a polypeptide or the order of nucleotides in a polynucleotide.

As used herein, "polypeptide", "peptide", and "protein" are used interchangeably and mean a compound that consist of two or more amino acids that are linked by means of peptide bonds.

As used herein, the terms "complementary" or "complementarity" refer to the pairing of bases, purines and pyrimidines, that associate through hydrogen bonding in double stranded nucleic acids. For example, the following base pairs are complementary: guanine and cytosine; adenine and thymine; and adenine and uracil. The terms, as used herein, include complete and partial complementarity.

Isolated Proteins, Polypeptides and Polynucleotides

A first aspect of the present invention relates to isolated LCAT polynucleotides. The polynucleotide sequences of the present invention include isolated polynucleotides that encode the polypeptides of the invention having a deduced amino acid sequence selected from the group of sequences set forth in the Sequence Listing and to other polynucleotide sequences closely related to such sequences and variants thereof.

The invention provides a polynucleotide sequence identical over its entire length to each coding sequence as set forth in the Sequence Listing. The invention also provides the coding sequence for the mature polypeptide or a fragment thereof, as well as the coding sequence for the mature polypeptide or a fragment thereof in a reading frame with other coding sequences, such as those encoding a leader or secretory sequence, a pre-, pro-, or prepro-protein sequence. The polynucleotide can also include non-coding sequences, including for example, but not limited to, non-coding 5' and 3' sequences, such as the transcribed, untranslated sequences, termination signals, ribosome binding sites, sequences that stabilize mRNA, introns, polyadenylation signals, and additional coding sequence that encodes additional amino acids. For example, a marker sequence can be included to facilitate the purification of the fused polypeptide. Polynucleotides of the present invention also include polynucleotides comprising a structural gene and the naturally associated sequences that control gene expression.

The invention also includes polynucleotides of the formula:

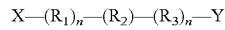

wherein, at the 5' end, X is hydrogen, and at the 3' end, Y is hydrogen or a metal, $R_1$ and $R_3$ are any nucleic acid residue, n is an integer between 0 and 3000, preferably between 1 and 1000 and $R_2$ is a nucleic acid sequence of the invention, particularly a nucleic acid sequence selected from the group set forth in the Sequence Listing and preferably SEQ ID NOs: 2, 4, 6, 8, 10–29, 33, 42–51, 73 and 75. In the formula, $R_2$ is oriented so that its 5' end residue is at the left, bound to $R_1$, and its 3' end residue is at the right, bound to $R_3$. Any stretch of nucleic acid residues denoted by either R group, where R is greater than 1, may be either a heteropolymer or a homopolymer, preferably a heteropolymer.

The invention also relates to variants of the polynucleotides described herein that encode for variants of the polypeptides of the invention. Variants that are fragments of the polynucleotides of the invention can be used to synthesize full-length polynucleotides of the invention. Preferred embodiments are polynucleotides encoding polypeptide variants wherein 5 to 10, 1 to 5, 1 to 3, 2, 1 or no amino acid residues of a polypeptide sequence of the invention are substituted, added or deleted, in any combination. Particularly preferred are substitutions, additions, and deletions that are silent such that they do not alter the properties or activities of the polynucleotide or polypeptide.

Further preferred embodiments of the invention that are at least 50%, 60%, or 70% identical over their entire length to a polynucleotide encoding a polypeptide of the invention, and polynucleotides that are complementary to such polynucleotides. More preferable are polynucleotides that comprise a region that is at least 80% identical over its entire length to a polynucleotide encoding a polypeptide of the invention and polynucleotides that are complementary thereto. In this regard, polynucleotides at least 90% identical over their entire length are particularly preferred, those at least 95% identical are especially preferred. Further, those with at least 97% identity are highly preferred and those with at least 98% and 99% identity are particularly highly preferred, with those at least 99% being the most highly preferred.

Preferred embodiments are polynucleotides that encode polypeptides that retain substantially the same biological function or activity as determined by the methods described herein as the mature polypeptides encoded by the polynucleotides set forth in the Sequence Listing.

The invention further relates to polynucleotides that hybridize to the above-described sequences. In particular, the invention relates to polynucleotides that hybridize under stringent conditions to the above-described polynucleotides. An example of stringent hybridization conditions is overnight incubation at 42° C. in a solution comprising 50% formamide, 5×SSC (150 mM NaCl, 15 mM trisodium citrate), 50 mM sodium phosphate (pH 7.6), 5× Denhardt's solution, 10% dextran sulfate, and 20 micrograms/milliliter denatured, sheared salmon sperm DNA, followed by washing the hybridization support in 0.1×SSC at approximately 65° C. Also included are polynucleotides that hybridize under a wash stringency of 0.1×SSC or 0.1×SSPE (at 50° C. Other hybridization and wash conditions are well known and are exemplified in Sambrook, et al., Molecular Cloning: A Laboratory Manual, Second Edition, Cold Spring Harbor, N.Y. (1989), particularly Chapter 11.

The invention also provides a polynucleotide consisting essentially of a polynucleotide sequence obtainable by screening an appropriate library containing the complete gene for a polynucleotide sequence set for in the Sequence Listing under stringent hybridization conditions with a probe having the sequence of said polynucleotide sequence or a fragment thereof; and isolating said polynucleotide sequence. Methods for screening libraries are well known in the art and can be found for example in Sambrook, et al., *Molecular Cloning: A Laboratory Manual*, Second Edition, Cold Spring Harbor, N.Y. (1989), particularly Chapter 8 and Ausubel et al., *Short Protocols in Molecular Biology*, 3$^{rd}$ ed, Wiley and Sons, 1995, chapter 6. Nucleic acid sequences useful for obtaining such a polynucleotide include, for example, probes and primers as described herein and in particular SEQ ID NO: 2, 4, 6, 8, 10–29, 33, 42–51, 73 and 75. These sequences are particularly useful in screening libraries obtained from *Arabidopsis*, soybean and corn for sequences encoding lecithin:cholesterol acyltransferase and lecithin:cholesterol acyltransferase-like polypeptides and for screening libraries for sequences encoding acyl CoA:cholesterol acyl transferase and acyl CoA:cholesterol acyl transferase-like polypeptides.

As discussed herein regarding polynucleotide assays of the invention, for example, polynucleotides of the invention can be used as a hybridization probe for RNA, cDNA, or genomic DNA to isolate full length cDNAs or genomic clones encoding a polypeptide and to isolate cDNA or genomic clones of other genes that have a high sequence similarity to a polynucleotide set forth in the Sequence Listing and in particular SEQ ID NO: 2, 4, 6, 8, 10–29, 33, 42–51, 73 and 75. Such probes will generally comprise at least 15 bases. Preferably such probes will have at least 30 bases and can have at least 50 bases. Particularly preferred probes will have between 30 bases and 50 bases, inclusive.

The coding region of each gene that comprises or is comprised by a polynucleotide sequence set forth in the Sequence Listing may be isolated by screening using a DNA sequence provided in the Sequence Listing to synthesize an oligonucleotide probe. A labeled oligonucleotide having a sequence complementary to that of a gene of the invention is then used to screen a library of cDNA, genomic DNA or mRNA to identify members of the library which hybridize to the probe. For example, synthetic oligonucleotides are prepared which correspond to the LCAT EST sequences. The oligonucleotides are used as primers in polymerase chain reaction (PCR) techniques to obtain 5' and 3' terminal sequence of LCAT genes. Alternatively, where oligonucleotides of low degeneracy can be prepared from particular LCAT peptides, such probes may be used directly to screen gene libraries for LCAT gene sequences. In particular, screening of cDNA libraries in phage vectors is useful in such methods due to lower levels of background hybridization.

Typically, a LCAT sequence obtainable from the use of nucleic acid probes will show 60–70% sequence identity between the target LCAT sequence and the encoding sequence used as a probe. However, lengthy sequences with as little as 50–60% sequence identity may also be obtained. The nucleic acid probes may be a lengthy fragment of the nucleic acid sequence, or may also be a shorter, oligonuoleotide probe. When longer nucleic acid fragments are employed as probes (greater than about 100 bp), one may screen at lower stringencies in order to obtain sequences from the target sample which have 20–50% deviation (i.e., 50–80% sequence homology) from the sequences used as probe. Oligonucleotide probes can be considerably shorter than the entire nucleic acid sequence encoding an LCAT enzyme, but should be at least about 10, preferably at least about 15, and more preferably at least about 20 nucleotides. A higher degree of sequence identity is desired when shorter regions are used as opposed to longer regions. It may thus be desirable to identify regions of highly conserved amino acid sequence to design oligonucleotide probes for detecting and recovering other related LCAT genes. Shorter probes are often particularly useful for polymerase chain reactions (PCR), especially when highly conserved sequences can be identified. (See, Gould, et al., *PNAS USA* (1989) 86:1934–1938.).

Another aspect of the present invention relates to LCAT polypeptides. Such polypeptides include isolated polypeptides set forth in the Sequence Listing, as well as polypeptides and fragments thereof, particularly those polypeptides which exhibit LCAT activity and also those polypeptides which have at least 50%, 60% or 70% identity, preferably at least 80% identity, more preferably at least 90% identity, and most preferably at least 95% identity to a polypeptide sequence selected from the group of sequences set forth in the Sequence Listing, and also include portions of such polypeptides, wherein such portion of the polypeptide preferably includes at least 30 amino acids and more preferably includes at least 50 amino acids.

"Identity", as is well understood in the art, is a relationship between two or more polypeptide sequences or two or more polynucleotide sequences, as determined by comparing the sequences. In the art, "identity" also means the degree of sequence relatedness between polypeptide or polynucleotide sequences, as determined by the match between strings of such sequences. "Identity" can be readily calculated by known methods including, but not limited to, those described in *Computational Molecular Biology*, Lesk, A. M., ed., Oxford University Press, New York (1988); *Biocomputing: Informatics and Genome Projects*, Smith, D. W., ed., Academic Press, New York, 1993; *Computer Analysis of Sequence Data*, Part I, Griffin, A. M. and Griffin, H. G., eds., Humana Press, New Jersey (1994); *Sequence Analysis in Molecular Biology*, von Heinje, G., Academic Press (1987); *Sequence Analysis Primer*, Gribskov, M. and Devereux, J., eds., Stockton Press, New York (1991); and Carillo, H., and Lipman, D., SIAM *J Applied Math*, 48:1073 (1988). Methods to determine identity are designed to give the largest match between the sequences tested. Moreover, methods to determine identity are codified in publicly available programs. Computer programs which can be used to determine identity between two sequences include, but are not limited to, GCG (Devereux, J., et al., *Nucleic Acids Research* 12(1):387 (1984); suite of five BLAST programs, three designed for nucleotide sequences queries (BLASTN, BLASTX, and TBLASTX) and two designed for protein sequence queries (BLASTP and TBLASTN) (Coulson, *Trends in Biotechnology*, 12: 76–80 (1994); Birren, et al., *Genome Analysis*, 1: 543–559 (1997)). The BLAST X program is publicly available from NCBI and other sources (BLASTManual, Altschul, S., et al., NCBI NLM NIH, Bethesda, Md. 20894; Altschul, S., et al., *J. Mol. Biol.*, 215:403–410 (1990)). The well known Smith Waterman algorithm can also be used to determine identity.

Parameters for polypeptide sequence comparison typically include the following:

Algorithm: Needleman and Wunsch, *J. Mol. Biol.* 48:443–453 (1970)

Comparison matrix: BLOSSUM62 from Hentikoff and Hentikoff, *Proc. Natl. Acad. Sci USA* 89:10915–10919 (1992)
Gap Penalty: 12
Gap Length Penalty: 4
A program which can be used with these parameters is publicly available as the "gap" program from Genetics Computer Group, Madison Wis. The above parameters along with no penalty for end gap are the default parameters for peptide comparisons.

Parameters for polynucleotide sequence comparison include the following:
Algorithm: Needleman and Wunsch, J. Mol. Biol. 48:443–453 (1970)
Comparison matrix: matches=+10; mismatches=0
Gap Penalty: 50
Gap Length Penalty: 3
A program which can be used with these parameters is publicly available as the "gap" program from Genetics Computer Group, Madison Wis. The above parameters are the default parameters for nucleic acid comparisons.

The invention also includes polypeptides of the formula:

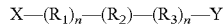

wherein, at the amino terminus, X is hydrogen, and at the carboxyl terminus, Y is hydrogen or a metal, $R_1$ and $R_3$ are any amino acid residue, n is an integer between 0 and 1000, and $R_2$ is an amino acid sequence of the invention, particularly an amino acid sequence selected from the group set forth in the Sequence Listing and preferably SEQ ID NOs: 3, 5, 7, 9, 74 and 76. In the formula, $R_2$ is oriented so that its amino terminal residue is at the left, bound to $R_1$, and its carboxy terminal residue is at the right, bound to $R_3$. Any stretch of amino acid residues denoted by either R group, where R is greater than 1, may be either a heteropolymer or a homopolymer, preferably a heteropolymer.

Polypeptides of the present invention include isolated polypeptides encoded by a polynucleotide comprising a sequence selected from the group of a sequence contained in SEQ ID NOs: 2, 4, 6, 8, 73 and 75.

The polypeptides of the present invention can be mature protein or can be part of a fusion protein.

Fragments and variants of the polypeptides are also considered to be a part of the invention. A fragment is a variant polypeptide which has an amino acid sequence that is entirely the same as part but not all of the amino acid sequence of the previously described polypeptides. The fragments can be "free-standing" or comprised within a larger polypeptide of which the fragment forms a part or a region, most preferably as a single continuous region. Preferred fragments are biologically active fragments which are those fragments that mediate activities of the polypeptides of the invention, including those with similar activity or improved activity or with a decreased activity. Also included are those polypeptides and polypeptide fragments that are antigenic or immunogenic in an animal, particularly a human and antibodies, either polyclonal or monoclonal that specifically bind the antigenic fragments. In one preferred embodiment, such antigenic or immunogenic fragments comprise at least 10 consecutive amino acids from the amino acid sequences disclosed herein or such sequences with at least one conservative amino acid substitution. In additional embodiments, such antigenic or immunogenic fragments comprise at least 15, at least 25, at least 50 or at least 100 consecutive amino acids from the amino acid sequences disclosed herein or such sequences with at least one conservative amino acid substitution. Methods for the production of antibodies from polypeptides and polypeptides conjugated to carrier molecules are well known in the art and can be found for example in Ausubel et al., *Short Protocols in Molecular Biology*, 3$^{rd}$ ed., Wiley & Sons, 1995, particularly chapter 11.

Variants of the polypeptide also include polypeptides that vary from the sequences set forth in the Sequence Listing by conservative amino acid substitutions, substitution of a residue by another with like characteristics. Those of ordinary skill in the art are aware that modifications in the amino acid sequence of a peptide, polypeptide, or protein can result in equivalent, or possibly improved, second generation peptides, etc., that display equivalent or superior functional characteristics when compared to the original amino acid sequence. The present invention accordingly encompasses such modified amino acid sequences. Alterations can include amino acid insertions, deletions, substitutions, truncations, fusions, shuffling of subunit sequences, and the like, provided that the peptide sequences produced by such modifications have substantially the same functional properties as the naturally occurring counterpart sequences disclosed herein.

One factor that can be considered in making such changes is the hydropathic index of amino acids. The importance of the hydropathic amino acid index in conferring interactive biological function on a protein has been discussed by Kyte and Doolittle (*J. Mol. Biol.,* 157: 105–132, 1982). It is accepted that the relative hydropathic character of amino acids contributes to the secondary structure of the resultant protein. This, in turn, affects the interaction of the protein with molecules such as enzymes, substrates, receptors, DNA, antibodies, antigens, etc.

Based on its hydrophobicity and charge characteristics, each amino acid has been assigned a hydropathic index as follows: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate/glutamine/aspartate/asparagine (−3.5); lysine (−3.9); and arginine (−4.5).

As is known in the art, certain amino acids in a peptide or protein can be substituted for other amino acids having a similar hydropathic index or score and produce a resultant peptide or protein having similar biological activity, i.e., which still retains biological functionality. In making such changes, it is preferable that amino acids having hydropathic indices within ±2 are substituted for one another. More preferred substitutions are those wherein the amino acids have hydropathic indices within ±1. Most preferred substitutions are those wherein the amino acids have hydropathic indices within ±0.5.

Like amino acids can also be substituted on the basis of hydrophilicity. U.S. Pat. No. 4,554,101 discloses that the greatest local average hydrophilicity of a protein, as governed by the hydrophilicity of its adjacent amino acids, correlates with a biological property of the protein. The following hydrophilicity values have been assigned to amino acids: arginine/lysine (+3.0); aspartate/glutamate (+3.0±1); serine (+0.3); asparagine/glutamine (+0.2); glycine (0); threonine (−0.4); proline (−0.5±1); alanine/histidine (−0.5); cysteine (−1.0); methionine (−1.3); valine (−1.5); leucine/isoleucine (−1.8); tyrosine (−2.3); phenylalanine (−2.5); and tryptophan (−4). Thus, one amino acid in a peptide, polypeptide, or protein can be substituted by another amino acid having a similar hydrophilicity score and still produce a resultant protein having similar biological activity, i.e., still retaining correct biological function. In making such changes, amino acids having hydropathic indices within ±2 are preferably substituted for one another, those within ±1 are more preferred, and those within ±0.5 are most preferred.

As outlined above, amino acid substitutions in the peptides of the present invention can be based on the relative similarity of the amino acid side-chain substituents, for example, their hydrophobicity, hydrophilicity, charge, size, etc. Exemplary substitutions that take various of the foregoing characteristics into consideration in order to produce conservative amino acid changes resulting in silent changes within the present peptides, etc., can be selected from other members of the class to which the naturally occurring amino acid belongs. Amino acids can be divided into the following four groups: (1) acidic amino acids; (2) basic amino acids; (3) neutral polar amino acids; and (4) neutral non-polar amino acids. Representative amino acids within these various groups include, but are not limited to: (1) acidic (negatively charged) amino acids such as aspartic acid and glutamic acid; (2) basic (positively charged) amino acids such as arginine, histidine, and lysine; (3) neutral polar amino acids such as glycine, serine, threonine, cysteine, cystine, tyrosine, asparagine, and glutamine; and (4) neutral non-polar amino acids such as alanine, leucine, isoleucine, valine, proline, phenylalanine, tryptophan, and methionine. It should be noted that changes which are not expected to be advantageous can also be useful if these result in the production of functional sequences.

Variants that are fragments of the polypeptides of the invention can be used to produce the corresponding full length polypeptide by peptide synthesis. Therefore, these variants can be used as intermediates for producing the full-length polypeptides of the invention.

The polynucleotides and polypeptides of the invention can be used, for example, in the transformation of host cells, such as plant cells, animal cells, yeast cells, bacteria, bacteriophage, and viruses, as further discussed herein.

The invention also provides polynucleotides that encode a polypeptide that is a mature protein plus additional amino or carboxyl-terminal amino acids, or amino acids within the mature polypeptide (for example, when the mature form of the protein has more than one polypeptide chain). Such sequences can, for example, play a role in the processing of a protein from a precursor to a mature form, allow protein transport, shorten or lengthen protein half-life, or facilitate manipulation of the protein in assays or production. It is contemplated that cellular enzymes can be used to remove any additional amino acids from the mature protein.

A precursor protein, having the mature form of the polypeptide fused to one or more prosequences may be an inactive form of the polypeptide. The inactive precursors generally are activated when the prosequences are removed. Some or all of the prosequences may be removed prior to activation. Such precursor protein are generally called proproteins.

Preparation of Expression Constructs and Methods of Use

Of interest is the use of the nucleotide sequences in recombinant DNA constructs to direct the transcription or transcription and translation (expression) of the acyltransferase sequences of the present invention in a host cell. Of particular interest is the use of the polynucleotide sequences of the present invention in recombinant DNA constructs to direct the transcription or transcription and translation (expression) of the acyltransferase sequences of the present invention in a host plant cell.

The expression constructs generally comprise a regulatory sequence functional in a host cell operably linked to a nucleic acid sequence encoding a lecithin:cholesterol acyltransferase-like polypeptide or acyl CoA:cholesterol acyltransferase-like polypeptide of the present invention and a transcriptional termination region functional in a host plant cell. Of particular interest is the use of promoters (also referred to as transcriptional initiation regions) functional in plant host cells.

Those skilled in the art will recognize that there are a number of promoters which are functional in plant cells, and have been described in the literature including constitutive, inducible, tissue specific, organelle specific, developmentally regulated and environmentally regulated promoters. Chloroplast and plastid specific promoters, chloroplast or plastid functional promoters, and chloroplast or plastid operable promoters are also envisioned.

One set of promoters are constitutive promoters such as the CaMV35S or FMV35S promoters that yield high levels of expression in most plant organs. Enhanced or duplicated versions of the CaMV35S and FMV35S promoters are useful in the practice of this invention (Odell, et al. (1985) *Nature* 313:810–812; Rogers, U.S. Pat. No. 5,378,619). Other useful constitutive promoters include, but are not limited to, the mannopine synthase (mas) promoter, the nopaline synthase (nos) promoter, and the octopine synthase (ocs) promoter.

Useful inducible promoters include heat-shock promoters (Ou-Lee et al. (1986) *Proc. Natl. Acad. Sci. USA* 83: 6815; Ainley et al. (1990) *Plant Mol. Biol.* 14: 949), a nitrate-inducible promoter derived from the spinach nitrite reductase gene (Back et al. (1991) *Plant Mol. Biol.* 17: 9), hormone-inducible promoters (Yamaguchi-Shinozaki et al. (1990) *Plant Mol. Biol.* 15: 905; Kares et al. (1990) *Plant Mol. Biol.* 15: 905), and light-inducible promoters associated with the small subunit of RuBP carboxylase and LHCP gene families (Kuhlemeier et al. (1989) *Plant Cell* 1: 471; Feinbaum et al. (1991) *Mol. Gen. Genet.* 226: 449; Weisshaar et al. (1991) *EMBO J.* 10: 1777; Lam and Chua (1990) *Science* 248: 471; Castresana et al. (1988) *EMBO J.* 7: 1929; Schulze-Lefert et al. (1989) *EMBO J.* 8: 651).

In addition, it may also be preferred to bring about expression of the acyltransferase gene in specific tissues of the plant, such as leaf, stem, root, tuber, seed, fruit, etc., and the promoter chosen should have the desired tissue and developmental specificity. Examples of useful tissue-specific, developmentally-regulated promoters include fruit-specific promoters such as the E4 promoter (Cordes et al. (1989) *Plant Cell* 1:1025), the E8 promoter (Deikman et al. (1988) *EMBO J.* 7: 3315), the kiwifruit actinidin promoter (Lin et al. (1993) *PNAS* 90: 5939), the 2A11 promoter (Houck et al., U.S. Pat. No. 4,943,674), and the tomato pZ130 promoter (U.S. Pat. Nos. 5,175,095 and 5,530,185); the β-conglycinin 7S promoter (Doyle et al. (1986) *J. Biol. Chem.* 261: 9228; Slighton and Beachy (1987) *Planta* 172: 356), and seed-specific promoters (Knutzon et al. (1992) *Proc. Natl. Acad. Sci. USA* 89: 2624; Bustos et al. (1991) *EMBO J.* 10: 1469; Lam and Chua (1991) *J. Biol. Chem.* 266: 17131; Stayton et al. (1991) *Aust. J. Plant. Physiol.* 18: 507). Fruit-specific gene regulation is discussed in U.S. Pat. No. 5,753,475. Other useful seed-specific promoters include, but are not limited to, the napin, phaseolin, zein, soybean trypsin inhibitor, 7S, ADR12, ACP, stearoyl-ACP desaturase, oleosin, *Lasquerella* hydroxylase, and barley aldose reductase promoters (Bartels (1995) *Plant J.* 7: 809–822), the EA9 promoter (U.S. Pat. No. 5,420,034), and the Bce4 promoter (U.S. Pat. No. 5,530,194). Useful embryo-specific promoters include the corn globulin 1 and oleosin promoters. Useful endosperm-specific promoters include the rice glutelin-1 promoter, the promoters for the low-pI βamylase gene (Amy32b) (Rogers et al. (1984) *J. Biol. Chem.* 259: 12234), the high-pI βamylase gene (Amy 64) (Khurseed et al. (1988) *J. Biol. Chem.* 263: 18953), and the promoter for a barley thiol protease gene ("Aleurain") (Whittier et al. (1987) *Nucleic Acids Res.* 15: 2515).

Of particular interest is the expression of the nucleic acid sequences of the present invention from transcription initiation regions which are preferentially expressed in a plant seed tissue. Examples of such seed preferential transcription initiation sequences include those sequences derived from sequences encoding plant storage protein genes or from genes involved in fatty acid biosynthesis in oilseeds. Examples of such promoters include the 5' regulatory regions from such genes as napin (Kridl et al., *Seed Sci. Res.* 1:209:219 (1991)), phaseolin, zein, soybean trypsin inhibitor, ACP, stearoyl-ACP desaturase, soybean α' subunit of β-conglycinin (soy 7s, (Chen et al., *Proc. Natl. Acad. Sci.*, 83:8560–8564 (1986))) and oleosin. Seed-specific gene regulation is discussed in EP 0 255 378 B1 and U.S. Pat. Nos. 5,420,034 and 5,608,152. Promoter hybrids can also be constructed to enhance transcriptional activity (Hoffman, U.S. Pat. No. 5,106,739), or to combine desired transcriptional activity and tissue specificity.

It may be advantageous to direct the localization of proteins conferring LCAT to a particular subcellular compartment, for example, to the mitochondrion, endoplasmic reticulum, vacuoles, chloroplast or other plastidic compartment. For example, where the genes of interest of the present invention will be targeted to plastids, such as chloroplasts, for expression, the constructs will also employ the use of sequences to direct the gene to the plastid. Such sequences are referred to herein as chloroplast transit peptides (CTP) or plastid transit peptides (PTP). In this manner, where the gene of interest is not directly inserted into the plastid, the expression construct will additionally contain a gene encoding a transit peptide to direct the gene of interest to the plastid. The chloroplast transit peptides may be derived from the gene of interest, or may be derived from a heterologous sequence having a CTP. Such transit peptides are known in the art. See, for example, Von Heijne et al. (1991) *Plant Mol. Biol. Rep.* 9:104–126; Clark et al. (1989) *J. Biol. Chem.* 264:17544–17550; della-Cioppa et al. (1987) *Plant Physiol.* 84:965–968; Romer et al. (1993) *Biochem. Biophys. Res Commun.* 196:1414–1421; and, Shah et al. (1986) *Science* 233:478–481.

Depending upon the intended use, the constructs may contain the nucleic acid sequence which encodes the entire LCAT protein, a portion of the LCAT protein, the entire ACAT protein, or a portion of the ACAT protein. For example, where antisense inhibition of a given LCAT or ACAT protein is desired, the entire sequence is not required. Furthermore, where LCAT or ACAT sequences used in constructs are intended for use as probes, it may be advantageous to prepare constructs containing only a particular portion of a LCAT or ACAT encoding sequence, for example a sequence which is discovered to encode a highly conserved region.

The skilled artisan will recognize that there are various methods for the inhibition of expression of endogenous sequences in a host cell. Such methods include, but are not limited to antisense suppression (Smith, et al. (1988) *Nature* 334:724–726), co-suppression (Napoli, et al. (1989) *Plant Cell* 2:279–289), ribozymes (PCT Publication WO 97/10328), and combinations of sense and antisense Waterhouse, et al. (1998) *Proc. Natl. Acad. Sci. USA* 95:13959–13964. Methods for the suppression of endogenous sequences in a host cell typically employ the transcription or transcription and translation of at least a portion of the sequence to be suppressed. Such sequences may be homologous to coding as well as non-coding regions of the endogenous sequence.

Regulatory transcript termination regions may be provided in plant expression constructs of this invention as well. Transcript termination regions may be provided by the DNA sequence encoding the diacylglycerol acyltransferase or a convenient transcription termination region derived from a different gene source, for example, the transcript termination region which is naturally associated with the transcript initiation region. The skilled artisan will recognize that any convenient transcript termination region which is capable of terminating transcription in a plant cell may be employed in the constructs of the present invention.

Alternatively, constructs may be prepared to direct the expression of the LCAT or ACAT sequences directly from the host plant cell plastid. Such constructs and methods are known in the art and are generally described, for example, in Svab, et al. (1990) *Proc. Natl. Acad. Sci. USA* 87:8526–8530 and Svab and Maliga (1993) *Proc. Natl. Acad. Sci. USA* 90:913–917 and in U.S. Pat. No. 5,693,507.

A plant cell, tissue, organ, or plant into which the recombinant DNA constructs containing the expression constructs have been introduced is considered transformed, transfected, or transgenic. A transgenic or transformed cell or plant also includes progeny of the cell or plant and progeny produced from a breeding program employing such a transgenic plant as a parent in a cross and exhibiting an altered phenotype resulting from the presence of a LCAT nucleic acid sequence.

Plant expression or transcription constructs having a plant LCAT as the DNA sequence of interest for increased or decreased expression thereof may be employed with a wide variety of plant life, particularly, plant life involved in the production of vegetable oils for edible and industrial uses. Most especially preferred are temperate oilseed crops. Plants of interest include, but are not limited to, rapeseed (Canola and High Erucic Acid varieties), sunflower, safflower, cotton, soybean, peanut, coconut and oil palms, and corn. Depending on the method for introducing the recombinant constructs into the host cell, other DNA sequences may be required. Importantly, this invention is applicable to dicotyledyons and monocotyledons species alike and will be readily applicable to new and/or improved transformation and regulation techniques.

Of particular interest, is the use of plant LCAT and ACAT constructs in plants to produce plants or plant parts, including, but not limited to leaves, stems, roots, reproductive, and seed, with a modified content of lipid and/or sterol esters and to alter the oil production by such plants.

Of particular interest in the present invention, is the use of ACAT genes in conjunction with the LCAT sequences to increase the sterol content of seeds. Thus, overexpression of a nucleic acid sequence encoding an ACAT and LCAT in an oilseed crop may find use in the present invention to increase sterol levels in plant tissues and/or increase oil production.

It is contemplated that the gene sequences may be synthesized, either completely or in part, especially where it is desirable to provide plant-preferred sequences. Thus, all or a portion of the desired structural gene (that portion of the gene which encodes the LCAT or ACAT protein) may be synthesized using codons preferred by a selected host. Host-preferred codons may be determined, for example, from the codons used most frequently in the proteins expressed in a desired host species.

One skilled in the art will readily recognize that antibody preparations, nucleic acid probes (DNA and RNA) and the like may be prepared and used to screen and recover "homologous" or "related" sequences from a variety of plant sources. Homologous sequences are found when there is an identity of sequence, which may be determined upon comparison of sequence information, nucleic acid or amino acid, or through hybridization reactions between a known LCAT and a candidate source. Conservative changes, such as Glu/Asp, Val/Ile, Ser/Thr, Arg/Lys and Gln/Asn may also be considered in determining sequence homology. Amino acid sequences are considered homologous by as little as 25% sequence identity between the two complete mature proteins. (See generally, Doolittle, R. F., OF URES and ORFS (University Science Books, CA, 1986.)

Thus, other LCATs may be obtained from the specific sequences provided herein. Furthermore, it will be apparent that one can obtain natural and synthetic sequences, including modified amino acid sequences and starting materials for synthetic-protein modeling from the exemplified LCAT and ACAT sequences and from sequences which are obtained through the use of such exemplified sequences. Modified amino acid sequences include sequences which have been mutated, truncated, increased and the like, whether such sequences were partially or wholly synthesized. Sequences which are actually purified from plant preparations or are identical or encode identical proteins thereto, regardless of the method used to obtain the protein or sequence, are equally considered naturally derived.

For immunological screening, antibodies to the protein can be prepared by injecting rabbits or mice with the purified protein or portion thereof, such methods of preparing antibodies being well known to those in the art. Either monoclonal or polyclonal antibodies can be produced, although typically polyclonal antibodies are more useful for gene isolation. Western analysis may be conducted to determine that a related protein is present in a crude extract of the desired plant species, as determined by cross-reaction with the antibodies to the encoded proteins. When cross-reactivity is observed, genes encoding the related proteins are isolated by screening expression libraries representing the desired plant species. Expression libraries can be constructed in a variety of commercially available vectors, including lambda gt11, as described in Sambrook, et al. (*Molecular Cloning: A Laboratory Manual*, Second Edition (1989) Cold Spring Harbor Laboratory, Cold Spring Harbor, N.Y.).

To confirm the activity and specificity of the proteins encoded by the identified nucleic acid sequences as acyltransferase enzymes, in vitro assays are performed in insect cell cultures using baculovirus expression systems. Such baculovirus expression systems are known in the art and are described by Lee, et al. U.S. Pat. No. 5,348,886, the entirety of which is herein incorporated by reference.

In addition, other expression constructs may be prepared to assay for protein activity utilizing different expression systems. Such expression constructs are transformed into yeast or prokaryotic host and assayed for acyltransferase activity. Such expression systems are known in the art and are readily available through commercial sources.

The method of transformation in obtaining such transgenic plants is not critical to the instant invention, and various methods of plant transformation are currently available. Furthermore, as newer methods become available to transform crops, they may also be directly applied hereunder. For example, many plant species naturally susceptible to *Agrobacterium* infection may be successfully transformed via tripartite or binary vector methods of *Agrobacterium* mediated transformation. In many instances, it will be desirable to have the construct bordered on one or both sides by T-DNA, particularly having the left and right borders, more particularly the right border. This is particularly useful when the construct uses *A. tumefaciens* or *A. rhizogenes* as a mode for transformation, although the T-DNA borders may find use with other modes of transformation. In addition, techniques of microinjection, DNA particle bombardment, and electroporation have been developed which allow for the transformation of various monocot and dicot plant species.

Normally, included with the DNA construct will be a structural gene having the necessary regulatory regions for expression in a host and providing for selection of transformant cells. The gene may provide for resistance to a cytotoxic agent, e.g. antibiotic, heavy metal, toxin, etc., complementation providing prototrophy to an auxotrophic host, viral immunity or the like. Depending upon the number of different host species the expression construct or components thereof are introduced, one or more markers may be employed, where different conditions for selection are used for the different hosts.

Non-limiting examples of suitable selection markers include genes that confer resistance to bleomycin, gentamycin, glyphosate, hygromycin, kanamycin, methotrexate, phleomycin, phosphinotricin, spectinomycin, streptomycin, sulfonamide and sulfonylureas. Maliga et al., *Methods in Plant Molecular Biology*, Cold Spring Harbor Laboratory Press, 1995, p. 39. Examples of markers include, but are not limited to, alkaline phosphatase (AP), myc, hemagglutinin (HA), β glucuronidase (GUS), luciferase, and green fluorescent protein (GFP).

Where *Agrobacterium* is used for plant cell transformation, a vector may be used which may be introduced into the *Agrobacterium* host for homologous recombination with T-DNA or the Ti- or Ri-plasmid present in the *Agrobacterium* host. The Ti- or Ri-plasmid containing the T-DNA for recombination may be armed (capable of causing gall formation) or disarmed (incapable of causing gall formation), the latter being permissible, so long as the vir genes are present in the transformed *Agrobacterium* host. The armed plasmid can give a mixture of normal plant cells and gall.

In some instances where *Agrobacterium* is used as the vehicle for transforming host plant cells, the expression or transcription construct bordered by the T-DNA border region(s) will be inserted into a broad host range vector capable of replication in *E. coli* and *Agrobacterium*, there being broad host range vectors described in the literature. Commonly used is pRK2 or derivatives thereof. See, for example, Ditta, et al., (*Proc. Nat. Acad. Sci., U.S.A.* (1980) 77:7347–7351) and EPA 0 120 515, which are incorporated herein by reference. Alternatively, one may insert the sequences to be expressed in plant cells into a vector containing separate replication sequences, one of which stabilizes the vector in *E. coli*, and the other in *Agrobacterium*. See, for example, McBride and Summerfelt (*Plant Mol. Biol.* (1990) 14:269–276), wherein the pRiHRI (Jouanin, et al., *Mol. Gen. Genet.* (1985) 201:370–374) origin of replication is utilized and provides for added stability of the plant expression vectors in host *Agrobacterium* cells.

Included with the expression construct and the T-DNA can be one or more markers, which allow for selection of transformed *Agrobacterium* and transformed plant cells. A number of markers have been developed for use with plant cells, such as resistance to chloramphenicol, kanamycin, the aminoglycoside G418, hygromycin, or the like. The particular marker employed is not essential to this invention, one or another marker being preferred depending on the particular host and the manner of construction.

For transformation of plant cells using *Agrobacterium*, explants may be combined and incubated with the transformed *Agrobacterium* for sufficient time for transformation, the bacteria killed, and the plant cells cultured in an appropriate selective medium. Once callus forms, shoot formation can be encouraged by employing the appropriate plant hormones in accordance with known methods and the shoots transferred to rooting medium for regeneration of plants. The plants may then be grown to seed and the seed used to establish repetitive generations and for isolation of vegetable oils.

Thus, in another aspect of the present invention, methods for modifying the sterol and/or stanol composition of a host cell. Of particular interest are methods for modifying the sterol and/or stanol composition of a host plant cell. In general the methods involve either increasing the levels of sterol ester compounds as a proportion of the total sterol compounds. The method generally comprises the use of expression constructs to direct the expression of the polynucleotides of the present invention in a host cell.

Also provided are methods for reducing the proportion of sterol ester compounds as a percentage of total sterol compounds in a host plant cell. The method generally comprises the use of expression constructs to direct the suppression of endogenous acyltransferase proteins in a host cell.

Of particular interest is the use of expression constructs to modify the levels of sterol compounds in a host plant cell. Most particular, the methods find use in modifying the levels of sterol compounds in seed oils obtained from plant seeds.

Also of interest is the use of expression constructs of the present invention to alter oil production in a host cell and in particular to increase oil production. Of particular interest is the use of expression constructs containing nucleic acid sequences encoding LCAT and/or ACAT polypeptides to transform host plant cells and to use these host cells to regenerate whole plants having increase oil production as compared to the same plant not containing the expression construct.

The oils obtained from transgenic plants having modified sterol compound content find use in a wide variety of applications. Of particular interest in the present invention is the use of the oils containing modified levels of sterol compounds in applications involved in improving human nutrition and cardiovascular health. For example, phytostanols are beneficial for lowering serum cholesterol (Ling, et al. (1995) *Life Sciences* 57:195–206).

Cholesterol-lowering compositions comprise the oils and sterol ester compound compositions obtained using the methods of the present invention. Such cholesterol lowering compositions include, but are not limited to foods, food products, processed foods, food ingredients, food additive compositions, or dietary/nutritional supplements that contain oils and/or fats. Non-limiting examples include margarines; butters; shortenings; cooking oils; frying oils; dressings, such as salad dressings; spreads; mayonnaises; and vitamin/mineral supplements. Patent documents relating to such compositions include, U.S. Pat. Nos. 4,588,717 and 5,244,887, and PCT International Publication Nos. WO 96/38047, WO 97/42830, WO 98/06405, and WO 98/06714. Additional non-limiting examples include toppings; dairy products such as cheese and processed cheese; processed meat; pastas; sauces; cereals; desserts, including frozen and shelf-stable desserts; dips; chips; baked goods; pastries; cookies; snack bars; confections; chocolates; beverages; unextracted seed; and unextracted seed that has been ground, cracked, milled, rolled, extruded, pelleted, defatted, dehydrated, or otherwise processed, but which still contains the oils, etc., disclosed herein.

The cholesterol-lowering compositions can also take the form of pharmaceutical compositions comprising a cholesterol-lowering effective amount of the oils or sterol compound compositions obtained using the methods of the present invention, along with a pharmaceutically acceptable carrier, excipient, or diluent. These pharmaceutical compositions can be in the form of a liquid or a solid. Liquids can be solutions or suspensions; solids can be in the form of a powder, a granule, a pill, a tablet, a gel, or an extrudate. U.S. Pat. No. 5,270,041 relates to sterol-containing pharmaceutical compositions.

Thus, by expression of the nucleic acid sequences encoding acyltransferase-like sequences of the present invention in a host cell, it is possible to modify the lipid content and/or composition as well as the sterol content and/or composition of the host cell.

The invention now being generally described, it will be more readily understood by reference to the following examples which are included for purposes of illustration only and are not intended to limit the present invention.

EXAMPLES

Example 1

RNA Isolations

Total RNA from the inflorescence and developing seeds of *Arabidopsis thaliana* was isolated for use in construction of complementary (cDNA) libraries. The procedure was an adaptation of the DNA isolation protocol of Webb and Knapp (D. M. Webb and S. J. Knapp, (1990) Plant Molec. Reporter, 8, 180–185). The following description assumes the use of Ig fresh weight of tissue. Frozen seed tissue was powdered by grinding under liquid nitrogen. The powder was added to 10 ml REC buffer (50 mM Tris-HCl, pH 9, 0.8M NaCl, 10 mM EDTA, 0.5% w/v CTAB (cetyltrimethyl-ammonium bromide)) along with 0.2 g insoluble polyvinylpolypyrrolidone, and ground at room temperature. The homogenate was centrifuged for 5 minutes at 12,000×g to pellet insoluble material. The resulting supernatant fraction was extracted with chloroform, and the top phase was recovered.

The RNA was then precipitated by addition of 1 volume RecP (50 mM Tris-HCL pH9, 10 mM EDTA and 0.5% (w/v) CTAB) and collected by brief centrifugation as before. The RNA pellet was redissolved in 0.4 ml of 1M NaCl. The RNA pellet was redissolved in water and extracted with phenol/chloroform. Sufficient 3M potassium acetate (pH 5) ws added to make the mixture 0.3M in acetate, followed by addition of two volumes of ethanol to precipitate the RNA. After washing with ethanol, this final RNA precipitate was dissolved in water and stored frozen.

Alternatively, total RNA may be obtained using TRIzol reagent (BRL-Lifetechnologies, Gaithersburg, Md.) following the manufacturer's protocol. The RNA precipitate was dissolved in water and stored frozen.

Example 2

Identification of LCAT Sequences

Searches were performed on a Silicon Graphics Unix computer using additional Bioaccellerator hardware and GenWeb software supplied by Compugen Ltd. This software and hardware enabled the use of the Smith-Waterman algorithm in searching DNA and protein databases using profiles as queries. The program used to query protein databases was profilesearch. This is a search where the query is not a single sequence but a profile based on a multiple alignment of amino acid or nucleic acid sequences. The profile was used to query a sequence data set, i.e., a sequence database. The profile contained all the pertinent information for scoring each position in a sequence, in effect replacing the "scoring matrix" used for the standard query searches. The program used to query nucleotide databases with a protein profile was tprofilesearch. Tprofilesearch searches nucleic acid databases using an amino acid profile query. As the search is running, sequences in the database are translated to amino acid sequences in six reading frames. The output file for tprofilesearch is identical to the output file for profilesearch except for an additional column that indicates the frame in which the best alignment occurred.

The Smith-Waterman algorithm, (Smith and Waterman (1981) *J. Molec. Biol.*, 147:195–197), was used to search for similarities between one sequence from the query and a group of sequences contained in the database.

A protein sequence of Lecithin: cholesterol acyltransferase from human (McLean J, et al. (1986) *Nucleic Acids Res.* 14(23):9397–406 SEQ ID NO: 1)) was used to search the NCBI non-redundant protein database using BLAST. Three sequences were identified from *Arabidopsis*, GenBank accessions AC004557 (referred to herein as LCAT1, SEQ ID NO:2), AC003027 (referred to herein as LCAT2, SEQ ID NO:4), and AL024486 (referred to herein as LCAT3, SEQ ID NO:6). The deduced amino acid sequences are provided in SEQ ID NOs: 3, 5, and 7, respectively.

The profile generated from the queries using PSI-BLAST was excised from the hyper text markup language (html) file. The worldwide web (www)/html interface to psiblast at ncbi stores the current generated profile matrix in a hidden field in the html file that is returned after each iteration of psiblast. However, this matrix has been encoded into string62 (s62) format for ease of transport through html. String62 format is a simple conversion of the values of the matrix into html legal ascii characters.

The encoded matrix width (x axis) is 26 characters, and comprise the consensus characters, the probabilities of each amino acid in the order A,B,C,D,E,F,G,H,I,K,L,M,N, P,Q, R,S,T,V,W,X,Y,Z (where B represents D and N, and Z represents Q and E, and X represents any amino acid), gap creation value, and gap extension value.

The length (y axis) of the matrix corresponds to the length of the sequences identified by PSI-BLAST. The order of the amino acids corresponds to the conserved amino acid sequence of the sequences identified using PSI-BLAST, with the N-terminal end at the top of the matrix. The probabilities of other amino acids at that position are represented for each amino acid along the x axis, below the respective single letter amino acid abbreviation.

Thus, each row of the profile consists of the highest scoring (consensus) amino acid, followed by the scores for each possible amino acid at that position in sequence matrix, the score for opening a gap that that position, and the score for continuing a gap at that position.

The string62 file is converted back into a profile for use in subsequent searches. The gap open field is set to 11 and the gap extension field is set to 1 along the x axis. The gap creation and gap extension values are known, based on the settings given to the PSI-BLAST algorithm. The matrix is exported to the standard GCG profile form. This format can be read by GenWeb.

The algorithm used to convert the string62 formatted file to the matrix is outlined in Table 1.

TABLE 1

1. if encoded character z then the value is blast score min
2. if encoded character Z then the value is blast score max
3. else if the encoded character is uppercase then its value is (64-(ascii # of char))
4. else if the encoded character is a digit the value is ((ascii # of char)-48)
5. else if the encoded character is not uppercase then the value is ((ascii # of char) - 87)
6. ALL B positions are set to min of D and N amino acids at that row in sequence matrix
7. ALL Z positions are set to min of Q and E amino acids at that row in sequence matrix
8. ALL X positions are set to min of all amino acids at that row in sequence matrix
9. kBLAST_SCORE_MAX = 999;
10. kBLAST_SCORE_MIN = -999;
11. all gap opens are set to 11
12. all gap lens are set to 1

The protein sequences of LCAT1, LCAT2, and LCAT3 as well as the PSI-BLAST profile were used to search public and proprietary databases for additional LCAT sequences. Two EST sequences were identified which appear to be identical to LCAT1 and LCAT3, respectively. One additional *Arabidopsis* sequence was identified from the proprietary databases, LCAT4 (SEQ ID NO:8). The deduced protein sequence of LCAT4 is provided in SEQ ID NO:9. Two additional genomic sequences were identified using the PSI-BLAST profile from libraries of *Arabidopsis* ecotypes Columbia and Landsberg, LCAT7 (SEQ ID NO:10) and LCAT8 (SEQ ID NO:11). The LCAT7 sequence was present in both the Columbia and Landsberg genomic libraries, while the LCAT8 sequence was only present in the Columbia library.

An open reading frame was predicted from the genomic sequence of LCAT7 in the *Arabidopsis* public database and this sequence was called MSH12 (referred to herein as LCAT5, SEQ ID NO: 73). The deduced protein sequence of LCAT5 is provided in SEQ ID NO: 74.

Figure 1C:
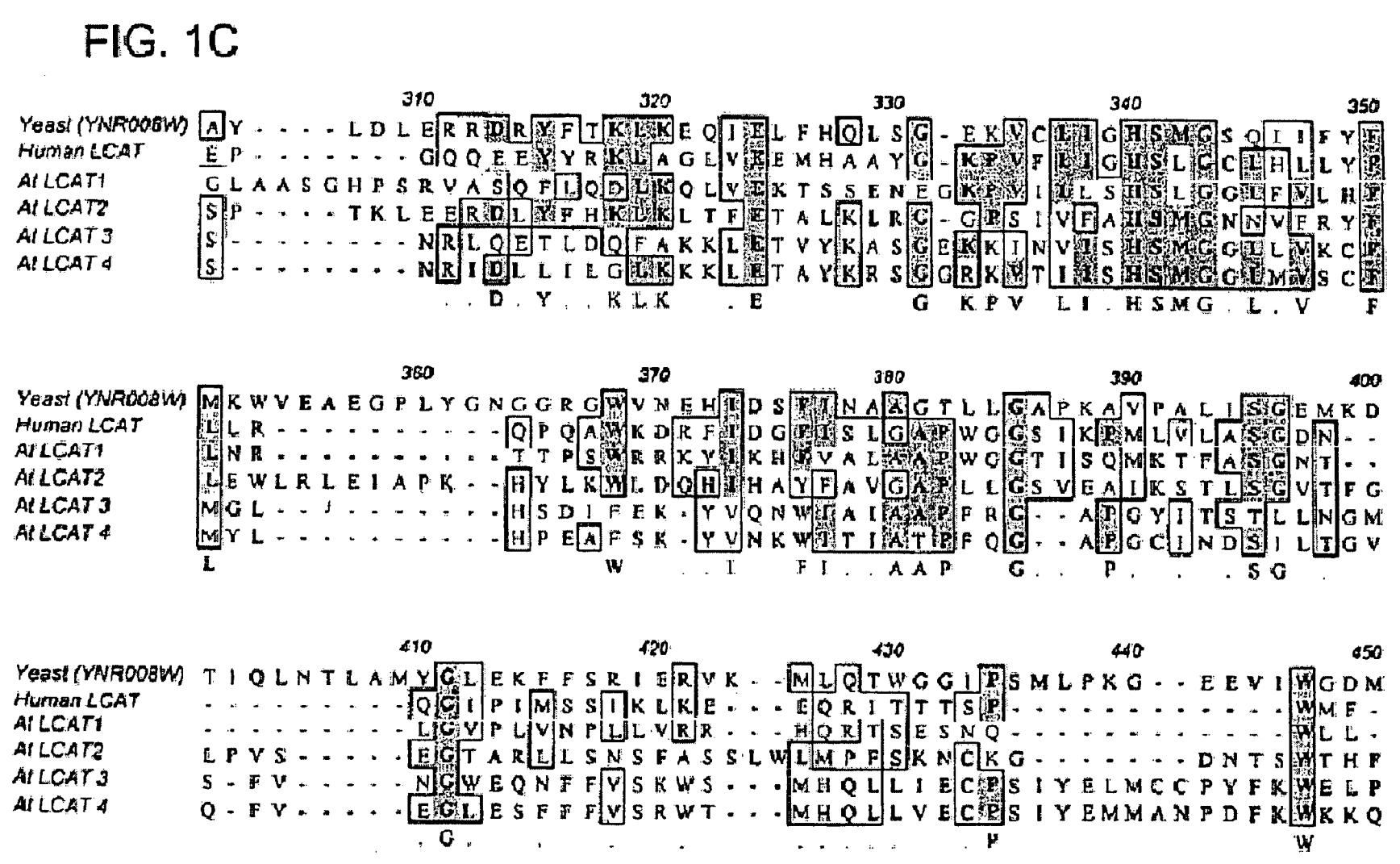

The PSI-BLAST profile and the LCAT sequences were used to query the public yeast database and proprietary libraries containing corn and soy EST sequences. The yeast genome contains only one gene, LRO1 (LCAT Related Open reading frame, YNR008W, FIG. 1) with distinct similarity to the human LCAT. The DNA sequence of LRO1 is provided in SEQ ID NO: 75 and the protein sequence is provided in SEQ ID NO: 76. Seven EST sequences were identified from soybean libraries as being LCAT sequences. Two sequences from soy (SEQ ID NOs: 12 and 13) are most closely related to the *Arabidopsis* LCAT1 sequence, a single sequence was identified as being most closely related to LCAT2 (SEQ ID NO: 14), three were closely related to LCAT3 (SEQ ID NOs: 15–17), and an additional single sequence was identified (SEQ ID NO: 18). A total of 11 corn EST sequences were identified as being related to the *Arabidopsis* LCAT sequences. Two corn EST sequences (SEQ ID NOs: 19 and 20) were most closely related to LCAT1, two sequences were identified as closely related to LCAT2 (SEQ ID NOs:

21 and 22), four corn EST sequences were identified as closely related to LCAT3 (SEQ ID NOs: 23–26), and an additional three corn EST sequences were also identified (SEQ ID NOs: 27–29).

Example 3

Identification of ACAT Sequences

Since plant ACATs are unknown in the art, searches were performed to identify known and related ACAT sequences from mammalian sources from public databases. These sequences were then used to search public and proprietary EST databases to identify plant ACAT-like sequences.

A public database containing mouse Expressed Sequence Tag (EST) sequences (dBEST) was searched for ACAT-like sequences. The search identified two sequences (SEQ ID 30 and 31) which were related (approximately 20% identical), but divergent, to known ACAT sequences.

In order to identify ACAT-like sequences from other organisms, the two mouse ACAT sequences were used to search public and proprietary databases containing EST sequences from human and rat tissues. Results of the search identified several sequences from the human database and from the rat database which were closely related to the mouse sequences. The human and rat ACAT-like EST sequences were assembled, using the GCG assembly program, to construct a complete inferred cDNA sequence by identifying overlapping sequences (SEQ ID NOs: 32 and 33, respectively).

The protein sequence of the human ACAT-like sequence was aligned with known ACAT sequences from human (Chang, et al. (1993) *J. Biol. Chem.* 268:20747–20755, SEQ ID NO:34), mouse (Uelmen, et al. (1995) *J. Biol. Chem.* 270:26192–26201 SEQ ID NO:35) and yeast (Yu, et al. (1996) *J. Biol. Chem.* 271:24157–24163, SEQ ID NO:36 and Yang, et al. (1996) *Science* 272:1353–1356, SEQ ID NO:37) using MacVector (Oxford Molecular, Inc.). Results of the alignment demonstrated that the sequence was related to the known sequences, however the related sequence was only about 25% similar to the known sequences.

The protein sequence of the human sterol O-acyltransferase (ACAT, Acyl CoA:Cholesterol acyltransferase, Accession number A48026) related sequence was used to search protein and nucleic acid Genbank databases. A single plant homologue was identified in the public *Arabidopsis* EST database (Accession A042298, SEQ ID NO:38). The protein sequence (SEQ ID NO:39)was translated from the EST sequence, and was found to contain a peptide sequence conserved in both mammalian and yeast ACATs (Chang et al., (1997) *Ann. Rev. Biochem.,* 66:613–638).

To obtain the entire coding region corresponding to the *Arabidopsis* ACAT-like EST, synthetic oligo-nucleotide primers were designed to amplify the 5' and 3' ends of partial cDNA clones containing ACAT-like sequences. Primers were designed according to the *Arabidopsis* ACAT-like EST sequence and were used in Rapid Amplification of cDNA Ends (RACE) reactions (Frohman et al. (1988) *Proc. Natl. Acad. Sci. USA* 85:8998–9002).

Primers were designed (5'-TGCAAATTGACGAGCA-CACCAACCCCTTC-3' (SEQ ID NO:40) and 5'-AAGGAT-GCTTTGAGTTCCTGACAATAGG-3' (SEQ ID NO:41)) to amplify the 5' end from the *Arabidopsis* ACAT EST sequence. Amplification of flanking sequences from cDNA clones were performed using the Marathon cDNA Amplification kit (Clontech, CA).

The sequence derived from the 5'-RACE amplification was used to search proprietary *Arabidopsis* EST libraries. A single EST accession, LIB25-088-C7 (SEQ ID NO:42), was identified which contained a sequence identical to the 5'-RACE sequence. Furthermore, LIB25-088-C7 was found to contain the complete putative coding sequence for the *Arabidopsis* ACAT-like product.

The nucleic acid as well as the putative translation product sequences of A042298 were used to search public and proprietary databases. Four EST sequences were identified in both soybean (SEQ ID NOs:43–46) and maize (SEQ ID NOs:47–50) proprietary databases, and a single ACAT-like sequence was identified from *Mortierrella alpina* EST sequences (SEQ ID NO:51).

Sequence alignments between ACAT sequences from several different sources were compared to identify the similarity between the sequences. Nucleotide sequences from known human and mouse ACATs, as well as nucleotide sequences from known yeast ACATs were compared to the ACAT-like EST sequences from human and *Arabidopsis*.

Analysis of the sequence alignments revealed several classes of ACATs based on sequence similarity. The known human and mouse ACATs, being 88% similar in the nucleotide sequence, formed one class of ACATs. Another class of ACATs included the yeast ACATs which are less than 20% similar to the known human and mouse class ACATs.

The final class of ACATs included the *Arabidopsis* and human sequences disclosed in the present invention. This class is approximately 22% similar to the known human and mouse ACAT class and approximately 23% similar to the yeast class of ACATs. Thus, the ACAT sequences disclosed in the present invention represent a novel class of ACAT enzymes. Partial mouse sequences of this class are also provided.

Example 4

Expression Construct Preparation

Constructs were prepared to direct expression of the LCAT1, LCAT2, LCAT3, LCAT4, LCAT5 and the yeast LRO1 sequences in plants and cultured insect cells. The entire coding region of each LCAT was amplified from the appropriate EST clone or an *Arabidopsis* genomic cDNA library using the following oligonucleotide primers in a polymerase chain reactions (PCR). The LCAT1 coding sequence was amplified from the EST clone Lib25-082-Q1-E1-G4 using the primers 5'-GGATCCGCGGCCGCACAATGAAAAAAATATCTT CACATTATTCGG-3' (SEQ ID NO:52) and 5'-GGATC-CCCTGCAGGTCATTCATTGACGGCATTAACATTGG-3' (SEQ ID NO:53). The LCAT2 coding sequence was amplified from an *Arabidopsis* genomic cDNA library using the synthetic oligo nucleotide primers 5'-GGATCCGCGGCCGCACAATGGGAGCGAATTCGA AATCAGTAACG-3' (SEQ ID NO:54) and 5'-GGATC-CCCTGCAGGTTAATACCCACTTTTATCAAGCTCCC-3' (SEQ ID NO:55). The LCAT3 coding sequence was amplified from the EST clone LIB22-004-Q1-E1-B4 using the synthetic oligo nucleotide primers 5'-GGATCCGCGGCCGCACAATGTCTCTATTACTGGA AGAGATC-3' (SEQ ID NO:56) and 5'-GGATCCCCTG-CAGGTTATGCATCAACAGAGACACTTACAGC-3' (SEQ ID NO:57). The LCAT4 coding sequence was amplified from the EST clone LIB23-007-Q1-E1-B5 using the synthetic oligo nucleotide primers 5'-GGATCCGCGGCCGCACAATGGGCTGGATTCCGT GTCCGTGC-3' (SEQ ID NO:58) and 5'-GGATCCCCTG-CAGGTTAACCAGAATCAACTACTTTGTG-3' (SEQ ID NO:59). The LCAT5 coding sequence was amplified from LIB23-053-Q1-E1-E3 using the synthetic oligo nucleotide primers 5'-GGATCCGCGGCCGCACAATGCCCCTTATTCATCG G-3' (SEQ ID NO:77) and 5'-GGATCCCCTGCAGGTCA-CAGCTTCAGGTCAATACG-3' (SEQ ID NO:78).

The yeast LROI coding sequence was amplified from genomic yeast DNA using the synthetic oligo nucleotide primers 5'GGATCCGCGGCCGCACAATGGGCACACTGTTTCG AAG3' (SEQ ID NO:79) and 5'GGATCCCCTGCAGGT-TACATTGGGAAGGGCATCTGAG3' (SEQ ID NO:80).

The entire coding region of the *Arabidopsis* ACAT sequence (SEQ ID NO: 42) was amplified from the EST clone LIB25-088-C7 using oligonucleotide primers 5'-TC-GACCTGCAGGAAGCTTAGAAATGGCGATTTTGGAT TC-3' (SEQ ID NO: 60) and 5'-GGATCCGCGGCCGCT-CATGACATCGATCCTTTTCGG-3' (SEQ ID NO: 61) in a polymerase chain reaction (PCR).

Each resulting PCR product was subcloned into pCR2.1Topo (Invitrogen) and labeled pCGN9964 (LCAT1), pCGN9985 (LCAT2), pCGN9965 (LCAT3), pCGN9995 (LCAT4), pCGN10964 (LCAT5), pCGN10963 (LRO1), and pCGN8626 (ACAT). Double stranded DNA sequence was obtained to verify that no errors were introduced by the PCR amplification.

4A. Baculovirus Expression Constructs

Constructs are prepared to direct the expression of the *Arabidopsis* LCAT and yeast LCAT sequences in cultured insect cells. The entire coding region of the LCAT proteins was removed from the respective constructs by digestion with NotI and Sse8387I, followed by gel electrophoresis and gel purification. The fragments containing the LCAT coding sequences were cloned into NotI and PstI digested baculovirus expression vector pFastBac1 (Gibco-BRL, Gaithersburg, Md.). The resulting baculovirus expression constructs were referred to as pCGN9992 (LCAT1), pCGN9993 (LCAT2), pCGN9994 (LCAT3), pCGN10900 (LCAT4), pCGN10967 (LCAT5), and pCGN10962 (LRO1).

4B. Plant Expression Construct Preparation

A plasmid containing the napin cassette derived from pCGN3223 (described in U.S. Pat. No. 5,639,790, the entirety of which is incorporated herein by reference) was modified to make it more useful for cloning large DNA fragments containing multiple restriction sites, and to allow the cloning of multiple napin fusion genes into plant binary transformation vectors. An adapter comprised of the self annealed oligonucleotide of sequence 5'-CGCGATT-TAAATGGCGCGCCCTGCAGGCGGCCGCCTGCAGGG CGCGCCATTTAA AT-3' (SEQ ID NO:62) was ligated into the cloning vector pBC SK+(Stratagene) after digestion with the restriction endonuclease BssHII to construct vector pCGN7765. Plarnids pCGN3223 and pCGN7765 were digested with NotI and ligated together. The resultant vector, pCGN7770, contained the pCGN7765 backbone with the napin seed specific expression cassette from pCGN3223.

The cloning cassette, pCGN7787, contained essentially the same regulatory elements as pCGN7770, with the exception of the napin regulatory regions of pCGN7770 have been replaced with the double CAMV 35S promoter and the tm1 polyadenylation and transcriptional termination region.

A binary vector for plant transformation, pCGN5139, was constructed from pCGN1558 (McBride and Summerfelt, (1990) Plant Molecular Biology, 14:269–276). In pCGN5139, the polylinker of pCGN1558 was replaced as a HindIII/Asp718 fragment with a polylinker containing unique restriction endonuclease sites, AscI, PacI, XbaI, SwaI, BamHI, and NotI. The Asp718 and HindIII restriction endonuclease sites are retained in pCGN5139.

A series of turbo binary vectors was constructed to allow for the rapid cloning of DNA sequences into binary vectors containing transcriptional initiation regions (promoters) and transcriptional termination regions.

The plasmid pCGN8618 was constructed by ligating oligonucleotides 5'-TCGAGGATCCGCGGCCGCAAGCT-TCCTGCAGG-3' (SEQ ID NO:63) and 5'-TCGACCTG-CAGGAAGCTTGCGGCCGCGGATCC-3' (SEQ ID NO:64) into SalI/XhoI-digested pCGN7770. A fragment containing the napin promoter, polylinker and napin 3' region was excised from pCGN8618 by digestion with Asp718I; the fragment was blunt-ended by filling in the 5' overhangs with Klenow fragment then ligated into pCGN5139 that had been digested with Asp718I and HindIII and blunt-ended by filling in the 5' overhangs with Klenow fragment. A plasmid containing the insert oriented so that the napin promoter was closest to the blunted Asp718I site of pCGN5139 and the napin 3' was closest to the blunted HindII site was subjected to sequence analysis to confirm both the insert orientation and the integrity of cloning junctions. The resulting plasmid was designated pCGN8622.

The plasmid pCGN8619 was constructed by ligating oligonucleotides 5'-TCGACCTGCAGGAAGCTTGCGGC-CGCGGATCC-3' (SEQ ID NO:65) and 5'-TCGAGGATC-CGCGGCCGCAAGCTTCCTGCAGG-3' (SEQ ID NO:66) into SalI/XhoI-digested pCGN7770. A fragment containing the napin promoter, polylinker and napin 3' region was removed from pCGN8619 by digestion with Asp718I; the fragment was blunt-ended by filling in the 5' overhangs with Klenow fragment then ligated into pCGN5139 that had been digested with Asp718I and HindIII and blunt-ended by filling in the 5' overhangs with Klenow fragment. A plasmid containing the insert oriented so that the napin promoter was closest to the blunted Asp718I site of pCGN5139 and the napin 3' was closest to the blunted HindIII site was subjected to sequence analysis to confirm both the insert orientation and the integrity of cloning junctions. The resulting plasmid was designated pCGN8623.

The plasmid pCGN8620 was constructed by ligating oligonucleotides 5'-TCGAGGATCCGCGGCCGCAAGCT-TCCTGCAGGAGCT-3' (SEQ ID NO:67) and 5'-CCTG-CAGGAAGCTTGCGGCCGCGGATCC-3' (SEQ ID NO:68) into SalI/SacI-digested pCGN7787. A fragrnent containing the d35S promoter, polylinker and tm13' region was removed from pCGN8620 by complete digestion with Asp718I and partial digestion with NotI. The fragment was blunt-ended by filling in the 5' overhangs with Klenow fragment then ligated into pCGN5139 that had been digested with Asp718I and HindIII and blunt-ended by filling in the 5' overhangs with Klenow fragment. A plasmid containing the insert oriented so that the d35S promoter was closest to the blunted Asp718I site of pCGN5139 and the tm13' was closest to the blunted HindIII site was subjected to sequence analysis to confirm both the insert orientation and the integrity of cloning junctions. The resulting plasmid was designated pCGN8624.

The plasmid pCGN8621 was constructed by ligating oligonucleotides 5'-TCGACCTGCAGGAAGCTTGCGGC- CGCGGATCCAGCT-3' (SEQ ID NO:69) and 5'-GGATC-CGCGGCCGCAAGCTTCCTGCAGG-3' (SEQ ID NO:70) into SalI/SacI-digested pCGN7787. A fragment containing the d35S promoter, polylinker and tml13' region was removed from pCGN8621 by complete digestion with Asp718I and partial digestion with NotI. The fragment was blunt-ended by filling in the 5' overhangs with Klenow fragment then ligated into pCGN5139 that had been digested with Asp718I and HindIII and blunt-ended by filling in the 5' overhangs with Klenow fragment. A plasmid containing the insert oriented so that the d35S promoter was closest to the blunted Asp718I site of pCGN5139 and the tm13' was closest to the blunted HindIII site was subjected to sequence analysis to confirm both the insert orientation and the integrity of cloning junctions. The resulting plasmid was designated pCGN8625.

The plasmid construct pCGN8640 is a modification of pCGN8624 described above. A 938 bp PstI fragment isolated from transposon Tn7 which encodes bacterial spectinomycin and streptomycin resistance (Fling et al. (1985), *Nucleic Acids Research* 13(19):7095–7106), a determinant for *E. coli* and *Agrobacterium* selection, was blunt ended with Pfu polymerase. The blunt ended fragment was ligated into pCGN8624 that had been digested with SpeI and blunt ended with Pfu polymerase. The region containing the PstI fragment was sequenced to confirm both the insert orientation and the integrity of cloning junctions.

The spectinomycin resistance marker was introduced into pCGN8622 and pCGN8623 as follows. A 7.7 Kbp AvrII-SnaBI fragment from pCGN8640 was ligated to a 10.9 Kbp AvrII-SnaBI fragment from pCGN8623 or pCGN8622, described above. The resulting plasmids were pCGN8641 and pCGN8643, respectively.

The plasmid pCGN8644 was constructed by ligating oligonucleotides 5'-GATCACCTGCAGGAAGCTTGCG-GCCGCGGATCCAATGCA-3' (SEQ ID NO:71) and 5'-TTGGATCCGCGGCCGCAAGCTTCCTGCAGGT-3' (SEQ ID NO:72) into BamHI-PstI digested pCGN8640.

4C. Plant LCAT Expression Construct Preparation

The coding sequence of LCAT1 was cloned from pCGN9964 as a NotI/Sse8387I fragment into pCGN8640, pCGN8641, pCGN8643, and pCGN8644 to create the expression constructs pCGN9960, pCGN9961, pCGN9962, and pCGN9963, respectively. The construct pCGN9960 was designed to express the LCAT1 coding sequence in the sense orientation from the constitutive promoter CaMV 35S. The construct pCGN9961 was designed to express the LCAT1 coding sequence in the antisense orientation from the napin promoter. The construct pCGN9962 was designed to express the LCAT1 coding sequence in the sense orientation from the napin promoter. The construct pCGN9963 was designed to express the LCAT1 coding sequence in the antisense orientation from the constitutive promoter CaMV 35S.

The coding sequence of LCAT2 was cloned from pCGN9985 as a NotI/Sse8387I fragment into pCGN8640, pCGN8641, pCGN8643, and pCGN8644 to create the expression constructs pCGN9981, pCGN9982, pCGN9983, and pCGN9984, respectively. The construct pCGN9981 was designed to express the LCAT2 coding sequence in the sense orientation from the constitutive promoter CaMV 35S. The construct pCGN9982 was designed to express the LCAT2 coding sequence in the antisense orientation from the napin promoter. The construct pCGN9983 was designed to express the LCAT2 coding sequence in the sense orientation from the napin promoter. The construct pCGN9984 was designed to express the LCAT2 coding sequence in the antisense orientation from the constitutive promoter CaMV 35S.

The coding sequence of LCAT3 was cloned from pCGN9965 as a NotI/Sse8387I fragment into pCGN8640, pCGN8641, pCGN8643, and pCGN8644 to create the expression constructs pCGN9966, pCGN9967, pCGN9968, and pCGN9969, respectively. The construct pCGN9966 was designed to express the LCAT3 coding sequence in the sense orientation from the constitutive promoter CaMV 35S. The construct pCGN9967 was designed to express the LCAT3 coding sequence in the antisense orientation from the napin promoter. The construct pCGN9968 was designed to express the LCAT3 coding sequence in the sense orientation from the napin promoter. The construct pCGN9969 was designed to express the LCAT3 coding sequence in the antisense orientation from the constitutive promoter CaMV 35S.

The coding sequence of LCAT4 was cloned from pCGN9995 as a NotI/Sse8387I fragment into pCGN8640, pCGN8641, pCGN8643, and pCGN8644 to create the expression constructs pCGN9996, pCGN9997, pCGN9998, and pCGN9999, respectively. The construct pCGN9996 was designed to express the LCAT4 coding sequence in the sense orientation from the constitutive promoter CaMV 35S. The construct pCGN9997 was designed to express the LCAT4 coding sequence in the antisense orientation from the napin promoter. The construct pCGN9998 was designed to express the LCAT4 coding sequence in the sense orientation from the napin promoter. The construct pCGN9999 was designed to express the LCAT4 coding sequence in the antisense orientation from the constitutive promoter CaMV 35S.

The coding sequence of LCAT5 was cloned from pCGN10964 as a NotI/Sse8387I fragment into pCGN9977 and pCGN9979, to create the expression constructs pCGN10965, and pCGN10966, respectively. The construct pCGN10965 was designed to express the LCAT5 coding sequence in the sense orientation from the constitutive promoter CaMV 35S. The construct pCGN10966 was designed to express the LCAT5 coding sequence in the sense orientation from the napin promoter.

The coding sequence of LRO1 was cloned from pCGN10963 as a NotI/Sse8387I fragment into pCGN9977 and pCGN9979, to create the expression constructs pCGN10960, and pCGN10961, respectively. The construct pCGN10960 was designed to express the LRO1 coding sequence in the sense orientation from the constitutive promoter CaMV 35S. The construct pCGN10961 was designed to express the LRO1 coding sequence in the sense orientation from the napin promoter.

4D. Plant ACAT Expression Construct Preparation

A fragment containing the *Arabidopsis* ACAT-like coding region was removed from pCGN8626 by digestion with Sse8387I and Not I. The fragment containing the ACAT-like sequence was ligated into PstI-Not I digested pCGN8622. The resulting plasmid was designated pCGN8627. DNA sequence analysis confirmed the integrity of the cloning junctions.

A fragment containing the *Arabidopsis* ACAT-like coding region (SEQ ID NO: 42) was removed from pCGN8626 by digestion with Sse8387I and Not I. The fragment was ligated into PstI-Not I digested pCGN8623. The resulting plasmid was designated pCGN8628. DNA sequence analysis confirmed the integrity of the cloning junctions.

A fragment containing the *Arabidopsis* ACAT-like coding region was removed from pCGN8626 by digestion with Sse8387 and Not I. The fragment was ligated into PstI-Not I digested pCGN8624. The resulting plasmid was designated pCGN8629. DNA sequence analysis confirmed the integrity of the cloning junctions.

A fragment containing the *Arabidopsis* ACAT-like coding region was removed from pCGN8626 by digestion with Sse8387 and Not I. The fragment was ligated into PstI-Not I digested pCGN8625. The resulting plasmid was designated pCGN8630. DNA sequence analysis confirmed the integrity of the cloning junctions.

An additional expression construct for the suppression of endogenous ACAT-like activity was also prepared. The construct pCGN8660 was constructed by cloning approximately 1 Kb of the *Arabidopsis* ACAT-like coding region from pCGN8626 in the sense orientation, and the full-length *Arabidopsis* ACAT-like coding region in the antisense orientation under the regulatory control of the napin transcription initiation sequence.

For expression of the rat ACAT-like sequence in plants, the NotI-Sse8387I fragment of pCGN8592 was cloned into NotI-PstI digested binary vectors pCGN8621, pCGN8622, and pCGN8624 to yield plasmids, pCGN 9700, pCGN9701, and pCGN9702, respectively. Plasmid pCGN9700 expresses a sense transcript of the rat ACAT-like cDNA under control of a napin promoter, plasmid pCGN9701 expresses an antisense transcript of the rat ACAT-like cDNA under control of a napin promoter, and plasmid pCGN9702 expresses a sense transcript of the rat ACAT-like cDNA under control of a double 35S promoter. Plasmids pCGN 9700, pCGN9701, and pCGN9702 were introduced in *Agrobacterium tumefaciens* EHA101.

Constructs were prepared to direct the expression of the rat ACAT-like sequence in the seed embryo of soybean and the endosperm of corn. For expression of the rat ACAT-like DNA sequence in soybean, a 1.5 kb NotI/Sse8387I fragment from pCGN8592 containing the coding sequence of the rat ACAT-like sequence was blunt ended using Mung bean nuclease, and ligated into the SmaI site of the turbo 7S binary/cloning vector pCGN8809 to create the vector pCGN8817 for transformation into soybean by particle bombardment. The vector pCGN8817 contained the operably linked components of the promoter region of the soybean α' subunit of β-conglycinin (7S promoter, (Chen et al., (1986), *Proc. Natl. Acad. Sci.*, 83:856014 8564), the DNA sequence coding for the entire rat ACAT-like protein, and the transcriptional termination region of pea RuBisCo small subunit, referred to as E9 3' (Coruzzi, et al. (1984) *EMBO J.* 3:1671–1679 and Morelli, et al. (1985) *Nature* 315:200–204). This construct further contained sequences for the selection of positive transformed plants by screening for resistance to glyphosate using the CP4 EPSPS (U.S. Pat. No. 5,633,435) expressed under the control of the figwort mosaic virus (FMV) promoter (U.S. Pat. No. 5,378,619) and the transcriptional termination region of E9.

For expression of the rat ACAT-like sequence in the corn endosperm, a 1.5 kb NotI/Sse8387I fragment from pCGN8592 containing the coding sequence of the rat ACAT-like sequence was blunt ended using Mung bean nuclease, and ligated into the BamHI site of the rice pGt1 expression cassette pCGN8592 for expression from the pGt1 promoter (Leisy, D. J. et al., Plant Mol. Biol. 14 (1989) 41–50) and the HSP70 intron sequence (U.S. Pat. No. 5,593,874). This cassette also included the transcriptional termination region downstream of the cloning site of nopaline synthase, nos 3' (Depicker et al., *J. Molec. Appl. Genet.* (1982) 1: 562–573). A 7.5 kb fragment containing the pgtl promoter, the DNA sequence encoding the rat ACAT-like protein, and the nos transcriptional termination sequence was cloned into the binary vector pCGN8816 to create the vector pCGN8818 for transformation into corn. This construct also contained sequences for the selection of positive transformants with kanamycin using the kanamycin resistance gene from Tn5 bacteria under the control of the CAMV 35S promoter and tm1 transcriptional termination regions.

Example 5

Expression in Insect Cell Culture

A baculovirus expression system was used to express the LCAT cDNAs in cultured insect cells.

The baculovirus expression constructs pCGN9992, pCGN9993, pCGN9994, pCGN10900, pCGN10962, and pCGN10967 were transformed and expressed using the BAC-to-BAC Baculovirus Expression System (Gibco-BRL, Gaithersburg, Md.) according to the manufacturer's directions.

The transformed insect cells were used to assay for acyltransferase activities using methods known in the art (see Example 8).

Example 6

Plant Transformation

A variety of methods have been developed to insert a DNA sequence of interest into the genome of a plant host to obtain the transcription or transcription and translation of the sequence to effect phenotypic changes. Transgenic plants were obtained by *Agrobacterium*-mediated transformation as described by Radke et al. (*Theor. Appl. Genet.* (1988) 75:685–694; *Plant Cell Reports* (1992) 11:499–505). Alternatively, microprojectile bombardment methods, such as described by Klein et al. (*Bio/Technology* 10:286–291) may also be used to obtain nuclear transformed plants. Other plant species may be similarly transformed using related techniques.

The plant binary constructs described above were used in plant transformation to direct the expression of the sterol acyltransferases in plant tissues. Binary vector constructs were transformed into strain EHA101 *Agrobacterium* cells (Hood et al., *J. Bacteriol* (1986) 168:1291–1301), by the method of Holsters et al. (*Mol. Gen. Genet.* (1978) 163: 181–187). Transgenic *Arabidopsis thaliana* plants were obtained by *Agrobacterium*-mediated transformation as described by Valverkens et al., (*Proc. Nat. Acad. Sci*. (1988) 85:5536–5540), Bent et al. ((1994), *Science* 265:1856–1860), and Bechtold et al. ((1993), *C. R.Acad. Sc., Life Sciences* 316:1194–1199).

Example 7

Plant Assays for Modified Sterol Content/Profile

7a: NMR of T2 Seed

Seed from plants expressing LCAT 1 through 4 under the control of the napin promoter were analyzed by NMR. *Arabidopsis* seeds from transgenic plants were placed directly into wide-mouth MAS NMR sample tubes.

High-resolution spectra were measured at 11.7 T (1H=500 MHz, 13C=125 mHz) using Varian NMR Instruments (Palo Alto, Calif.) Inova™ NMR spectrometers equipped with carbon-observe MAS Nanoprobes™. The 13C spectra were acquired without a field-frequency lock at ambient temperature (approx. 21–22° C.) for 14 hours using the following conditions: spectral width=29.996 kHz, acquisition time=2.185 seconds, p/2 pulse (3.8 ms) with no relaxation delay, 1H g B2=2.5 kHz with Waltz decoupling. Data processing conditions were typically: digital resolution 0.11 Hz, 0.3 to 1.5 Hz line broadening and time-reversed linear prediction of the first three data points. Chemical shifts were referenced by adding neat tetramethylsilane (TMS) to *Arabidopsis* seeds and using the resulting referencing parameters for subsequent spectra. The 13C resolution was 2–3 Hz for the most narrow seed resonances. Spectral resolution was independent of MAS spinning speeds (1.5–3.5 kHz) and data were typically obtained with 1.5 kHz spinning speeds. Spinning sidebands were approx. 1% of the main resonance. Phytosterol 13C assignments were based on model samples composed of triolein, β-sitosterol and cholesterol oleate. Triacylglycerol 13C assignments were made from comparison with literature assignments or with shifts computed from a 13C NMR database (Advanced Chemical Development, Inc., version 3.50, Toronto Canada).

The results of these analyses are displayed in FIG. 2 and show that there was a trend of an approximately 2 fold increase of phytosterols in the seeds derived from plant line 5 expressing the LCAT 4 gene (pCGN9998) under the control of the napin promoter. During the course of this analysis it was also noted that the average oil content of seed from plants expressing the LCAT2 construct (pCGN9983) under the control of the napin promoter was higher than that of controls. This is the first in planta evidence supporting the concept that overexpression of a nucleotide sequence encoding a lecithin:cholesterol acyltransferase-like polypeptide can increase oil content.

7b: HPLC/MS of T2 Seed

Seed oil from T2 plants expressing LCAT1 through 4 under the control of the napin promoter was extracted using an accelerated solvent extractor (ASE) method. Seed samples were ground, using a mortar and pestle, to achieve a fine homogeneous meal. Oil was obtained using a Dionex Accelerated Solvent Extractor (ASE). Clean ground seed was added to an equal amount of diatomaceous earth. The ground seed sample and the diatomaceous earth were thoroughly mixed until a homogeneous texture was achieved. The sample was then loaded into the instrument and oil extraction was achieved using hexane under validated laboratory protocols.

Oil from these seed samples was then analyzed for sterol ester analysis using HPLC/MS for free campesterol, stigmasterol, and sitosterol and their fatty acid esters. To the autosampler vial containing approximately 0.1 grams oil was added 0.3 mLs $CDCl_3$. One-hundred microliters of this solution was added to 900 microliters $CHCl_3$. Five microliters of this diluted sample was subsequently injected into an HPLC/MS with positive ion atmospheric pressure ionization. The individual components in the oils were separated using two 4.6×50 mm $C_8$ Zorbax columns in series and a gradient using acetonitrile and acetonitrile with 40% $CHCl_3$. The sterol concentrations were calculated assuming each sterol and its fatty acids have the same molar responses. This was observed to be the case with cholesterol and its esters and was assumed to be the case for campesterol, stigmasterol, and sitosterol. In the present study, the sterol identified as stigmasterol was actually an isomer of this compound.

Figure 3:
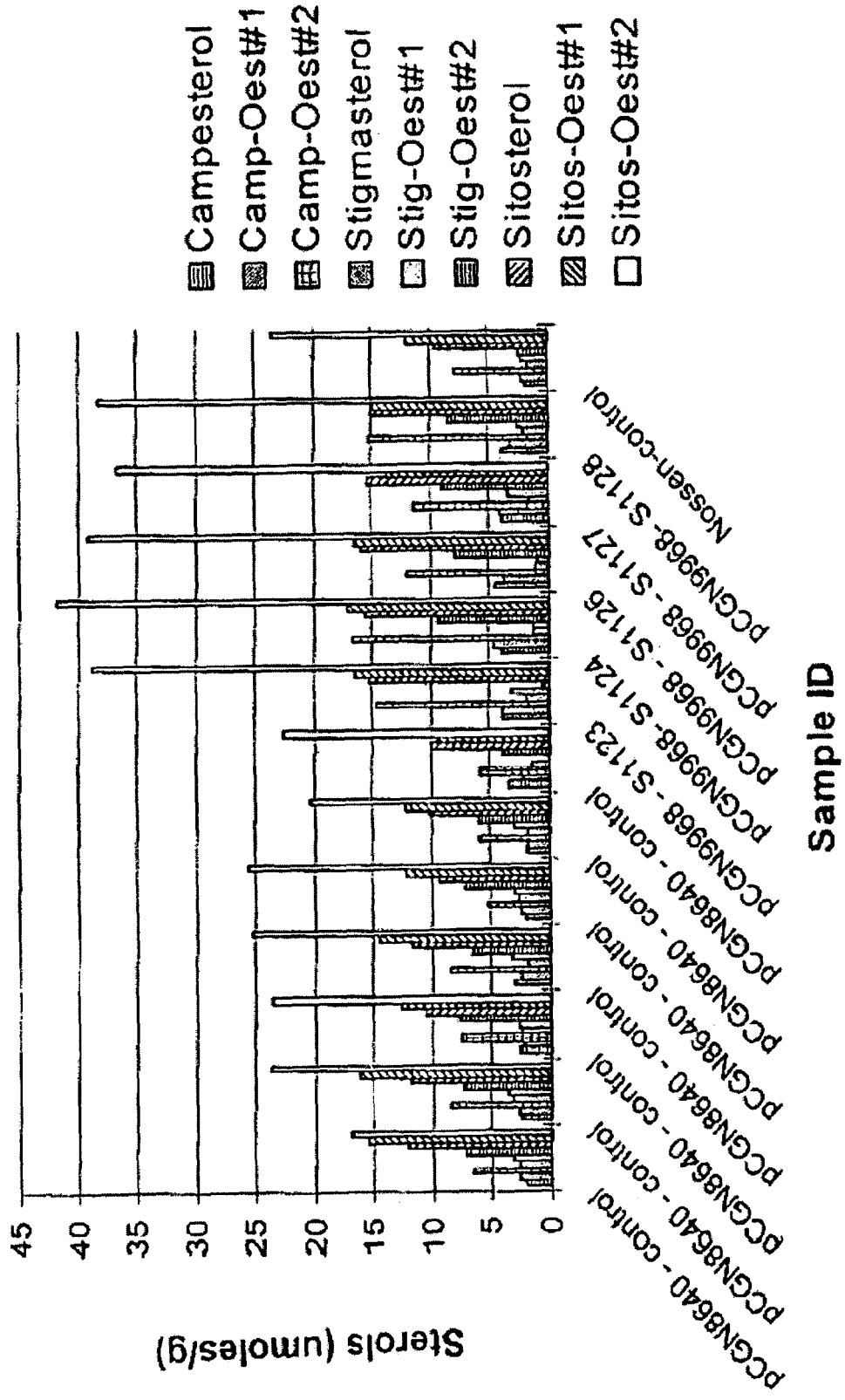
FIG. 3 shows the results of HPLC/MS sterol analysis on oil extracted from T2 seed from control lines (pCGN8640) and lines expressing LCAT3 (pCGN9968) under the control of the napin promoter.
Figure 4:
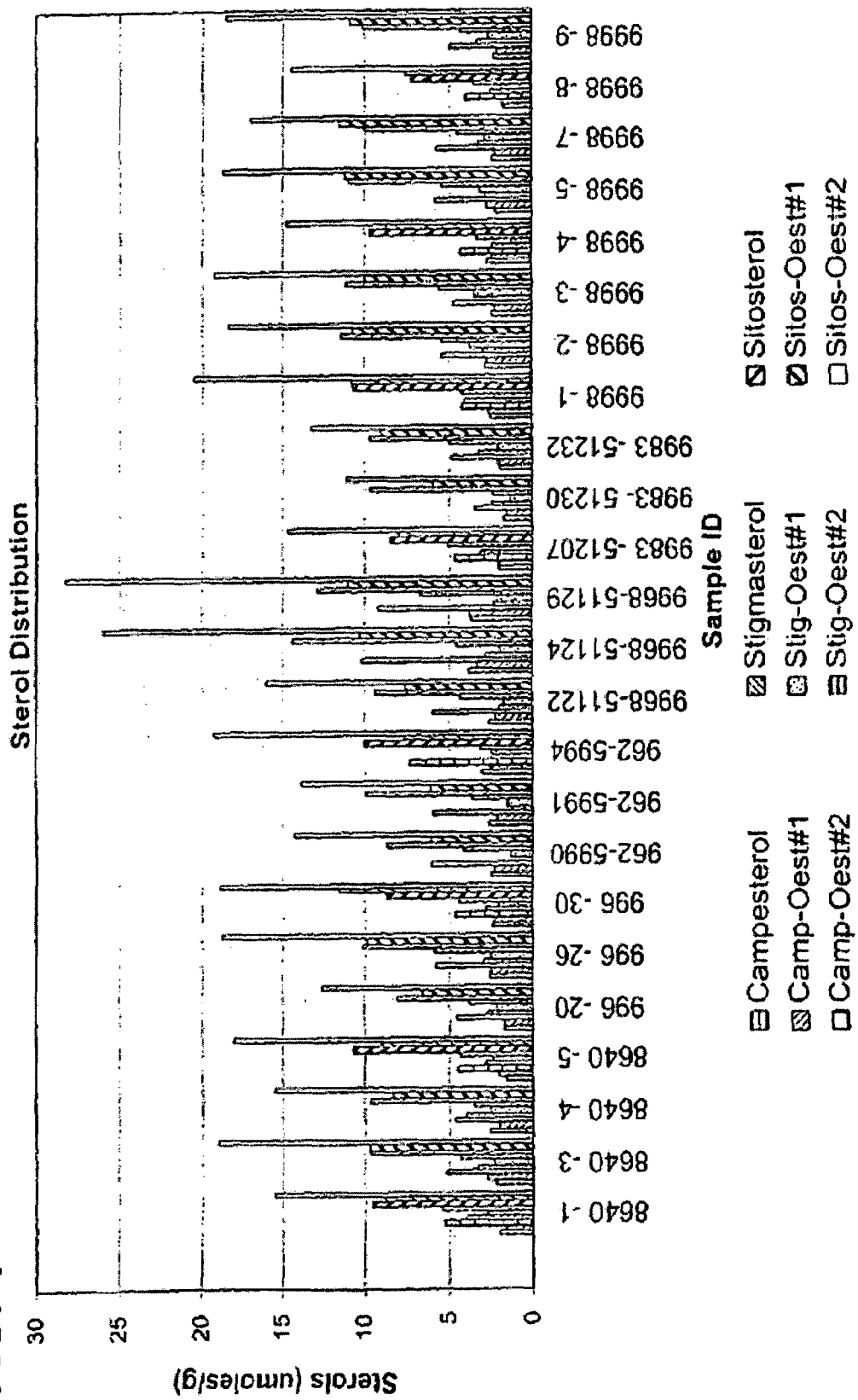
FIG. 4 shows the results of HPLC/MS sterol analysis on oil extracted from T2 seed from control lines (pCGN8640), and plant line expressing LCAT1 (pCGN9962), LCAT2 (pCGN9983), LCAT3 (pCGN9968), and LCAT4 (pCGN9998) under the control of the napin promoter. Additionally, data from 3 lines expressing LCAT4 under the control of the $^{35}$S promoter (pCGN9996) are shown.

The results of these analyses are displayed in FIGS. 3 and 4 and show that there were sterol ester enhancements on the order of 50%. in the seeds derived from six out of seven T2 plant lines expressing LCAT3 (pCGN9968) under the control of the napin promoter.

Example 8

Baculovirus Insect Cell Culture for Sterol Esterification Activity

Baculovirus expression construct pCGN9992, pCGN9993, pCGN9994 and pCGN10900 (see Example 4) were transformed and expressed using the BAC-TOBAC Baculovirus Expression System (Gibco-BRI, Gaithersburg, Md.) according to the manufacturer's instructions except harvesting of recombinant viruses was done 5 days post-transfection. The supernatant from the transfection mixture was used for generating virus stock which in turn was used for infecting Sf9 cells used in the assay.

The transformed cells were assayed for lecithin:sterol acyltransferase activities using the method described herein. Insect cells were centrifuged and the resulting cell pellet was either used immediately or stored at −70 C for later analysis. Cells were resuspended in Medium A (100 mM Tricine/NaOH, pH 7.8, 10% (w/v) glycerol, 280 mM NaCl with: 0.1 μM Aprotinin, 1 μM Leupeptin, and 100 μM Pefabloc (all from Boehringer Mannheim, Germany) and lysed by sonication (2×10 sec). Cell walls and other debris were pelleted by centrifugation (14,000×g, 10 min, 4° C.). The supernatant was transferred to a new vial and membranes pelleted by centrifugation (100,000×g, Ti 70.1 rotor, 46,000 rpm for 1 hour at 4° C.). Total membranes were resuspended in Medium A. Lecithin:sterol acyltransferase activity was assayed in a 0.1 ml reaction mixture containing 100 mM Tris/HCl, pH 7, 28 mM NaCl, 0.03% Triton X-100, 0.1 mM sitosterol, 20 μM 1,2-[$^{14}$C]-palmitoyl-phosphatidyl choline (246420 dpm/nmole), and 0.05–20 mg of membrane protein. After 15 minutes at 30° C., the reaction was terminated by addition of a 0.5 ml solution of methylene chloride:methanol (4:1, v/v) containing 100 μg cholesterol and cholesterol ester as cold carriers. A portion (0.1 ml) of the bottom organic layer was removed and evaporated under nitrogen gas. The concentrated extract was resuspended in 30 μl of hexane and spotted onto a silica gel-G thin layer chromatographic plate. The plate was migrated in hexane:diethyl ether:acetic acid (80:20:1) to the top, then air dried. Radioactivity was determined by exposure to a Low Energy Phosphor-imaging Screen. Following exposure, the screen was read on a phosphorimager.

The LCAT 4 protein from pCGN10900 in baculovirus membranes showed a radioactive spot in the region of the TLC plate where cholesterol ester migrates indicating that LCAT 4 has the ability to catalyze the transfer of an acyl group from lecithin (PC) to sitosterol to make a sitosterol ester.

Example 9

Plant Assay for Modified Lipid Content

Nir (near infrared spectroscopy spectral scanning) can be used to determine the total oil content of Arabidopsis seeds in a non-destructive way provided that a spectral calibration curve has been developed and validated for seed oil content. A seed oil spectral calibartion curve was developed using seed samples from 85 *Arabidopsis* plants. Seed was cleaned and scanned using a Foss NIR model 6500 (Foss-Nirs Systems, Inc.). Approximately 50 to 100 milligrams of whole seeds, per sample, were packed in a mini sample ring cup with quartz lens [1H-0307] consisting a mini-insert [1H-0337] and scanned in reflectance mode to obtain the spectral data. The seed samples were then ground, using a mortar and pestle, to achieve a fine homogeneous meal. The ground samples were measured for oil using an accelerated solvent extractor (ASE).

Measurement for the total oil content was performed on the Dionex Accelerated Solvent Extractor (ASE). Approximately 500 mg of clean ground seed was weighed to the nearest 0.1 mg onto a 9×9 cm weigh boat. An equal amount of diatomaceous earth was added using a top-loading balance accurate to the nearest 0.01 g. The ground seed sample and the diatomaceous earth were thoroughly mixed until a homogeneous texture was achieved. The sample was loaded on to the instrument and oil extraction was achieved using hexane under validated laboratory protocols. Standard Rapeseed samples were obtained from the Community Bureau of Reference (BCR). The ASE extraction method was validated using the BCR reference standards. A total percent oil recovery of 99% to 100% was achieved. "As-is" oil content was calculated to the nearest 0.01 mass percentage using the formula:

Oil Content=100% ×(vial plus extracted oil wt−initial vial wt)/(sample wt)

The analytical data generated by ASE were used to perform spectral calibrations. Nir calibration equations were generated using the built-in statistical package within the NirSytems winisi software. The spectral calibration portion of the software is capable of calibration and self-validation. From a total of 85 samples, 57 samples were used to generate the total percent oil calibration. The remaining samples were used to validate the oil calibrations. Optimized smoothing, derivative size, and mathematical treatment (modified partial least square) was utilized to generate the calibration. The samples that were not used in building respective calibrations were used as a validation set. Statistical tools such as correlation coefficient (R), coefficient of determination ($R^2$), standard error of prediction (SEP), and the standard error of prediction corrected for bias (SEPC) were used to evaluate the calibration equations.

T2 seeds from plants that had been transformed with the LCAT genes were cleaned and scanned using a Foss NIR model 6500 (Foss-Nirs Systems, Inc.). Approximately 50 to 100 milligrams of whole seeds, per sample, were packed in a mini sample ring cup with quartz lens [1H-0307] consisting a mini-insert [1H-0337] and scanned in reflectance mode to obtain the spectral data. Oil percentage in each seed sample was determined using the seed oil spectral calibration curve detailed above.

Figure 5:
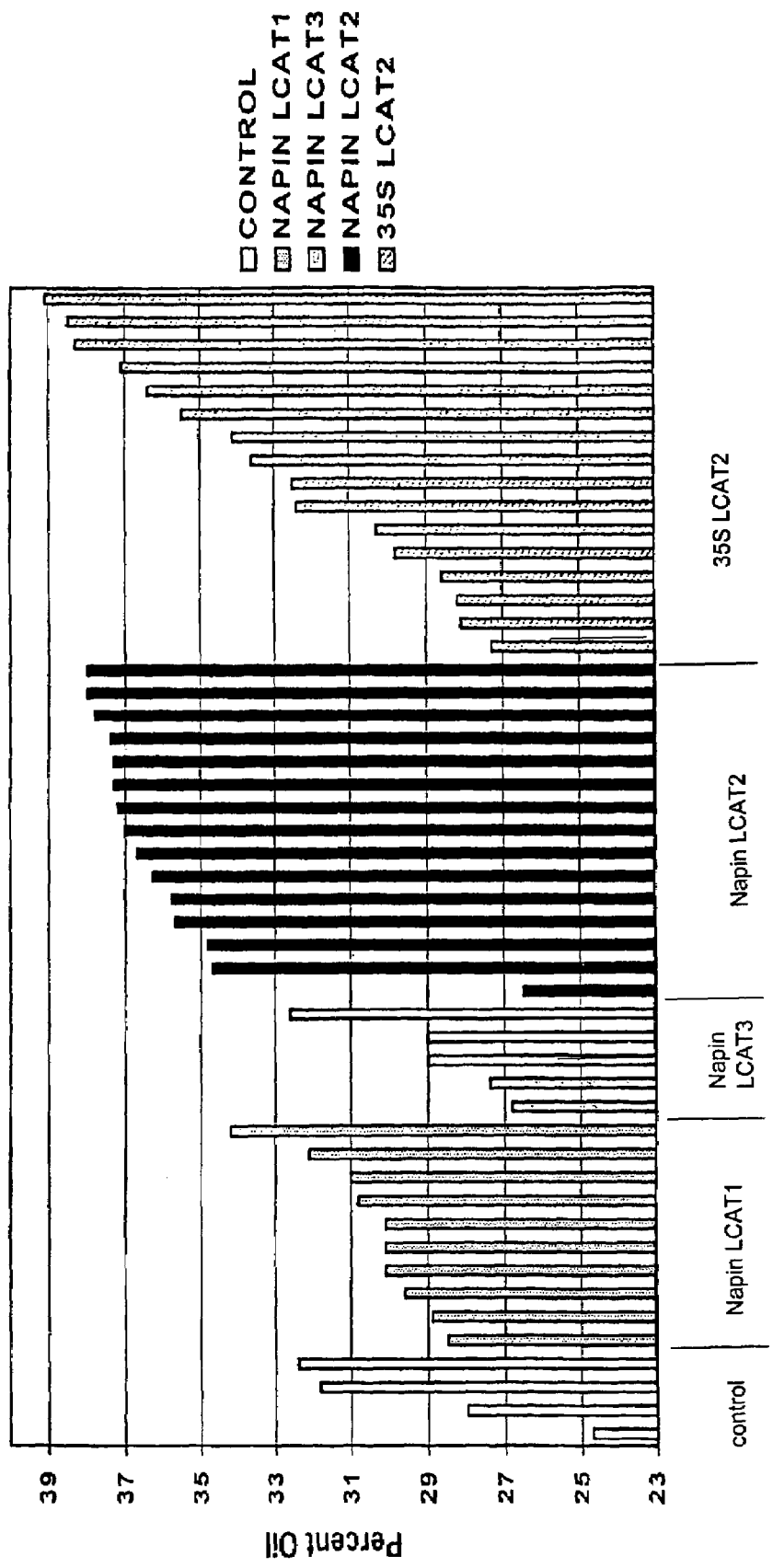
FIG. 5 shows the results of Nir analysis of the oil content of T2 seed from control lines (pCGN8640), and plant lines expressing LCAT1 (pCGN9962), LCAT2 (pCGN9983), and LCAT3 (pCGN9968) under the control of the napin promoter. Additionally, data from 16 lines expressing LCAT2 under the control of the 35S promoter pCGN9981) are shown.

The results of these analyses are found in FIG. 5 and Table 2 and show that there was a significant increase in the oil level in seed from T2 plants expressing the LCAT2 gene. This increase in oil was seen in plants when LCAT2 was driven by either the 35S constitutive promoter or the seed-specific napin promoter. These results show that overexpression of a nucleic acid sequence encoding a lecithin:cholesterol acyltransferase-like polypeptide can increase seed oil production in plants.

TABLE 2

|  | Construct number | Seed Oil Percentage (%) |
| --- | --- | --- |
| CONTROL |  | 24.7 |
| CONTROL |  | 28.0 |
| CONTROL |  | 31.8 |
| CONTROL |  | 32.4 |
| NAPIN LCAT1 | PCGN9962 | 28.5 |
| NAPIN LCAT1 | PCGN9962 | 28.9 |
| NAPIN LCAT1 | PCGN9962 | 29.6 |
| NAPIN LCAT1 | PCGN9962 | 30.1 |
| NAPIN LCAT1 | PCGN9962 | 30.1 |
| NAPIN LCAT1 | PCGN9962 | 30.1 |
| NAPIN LCAT1 | PCGN9962 | 30.8 |
| NAPIN LCAT1 | PCGN9962 | 31.0 |
| NAPIN LCAT1 | pCGN9962 | 32.1 |
| NAPIN LCAT1 | pCGN9962 | 34.2 |
| NAPIN LCAT3 | pCGN9968 | 26.8 |
| NAPIN LCAT3 | pCGN9968 | 27.4 |
| NAPIN LCAT3 | pCGN9968 | 29.0 |
| NAPIN LCAT3 | pCGN9968 | 29.0 |
| NAPIN LCAT3 | pCGN9968 | 32.6 |
| NAPIN LCAT2 | pCGN9983 | 26.5 |
| NAPIN LCAT2 | pCGN9983 | 34.7 |
| NAPIN LCAT2 | pCGN9983 | 34.8 |
| NAPIN LCAT2 | pCGN9983 | 35.7 |
| NAPIN LCAT2 | pCGN9983 | 35.8 |
| NAPIN LCAT2 | pCGN9983 | 36.3 |
| NAPIN LCAT2 | pCGN9983 | 36.7 |
| NAPIN LCAT2 | pCGN9983 | 37.0 |
| NAPIN LCAT2 | pCGN9983 | 37.2 |
| NAPIN LCAT2 | pCGN9983 | 37.3 |
| NAPIN LCAT2 | pCGN9983 | 37.3 |
| NAPIN LCAT2 | pCGN9983 | 37.4 |
| NAPIN LCAT2 | pCGN9983 | 37.8 |
| NAPIN LCAT2 | pCGN9983 | 38.0 |
| NAPIN LCAT2 | pCGN9983 | 38.0 |
| 35S LCAT2 | pCGN9981 | 27.3 |
| 35S LCAT2 | pCGN9981 | 28.1 |
| 35S LCAT2 | pCGN9981 | 28.2 |
| 35S LCAT2 | pCGN9981 | 28.6 |
| 35S LCAT2 | pCGN9981 | 29.8 |
| 35S LCAT2 | pCGN9981 | 30.3 |
| 35S LCAT2 | pCGN9981 | 32.4 |
| 35S LCAT2 | pCGN9981 | 32.5 |
| 35S LCAT2 | pCGN9981 | 33.6 |
| 35S LCAT2 | pCGN9981 | 34.1 |
| 35S LCAT2 | pCGN9981 | 35.5 |
| 35S LCAT2 | pCGN9981 | 36.4 |
| 35S LCAT2 | pCGN9981 | 37.1 |
| 35S LCAT2 | pCGN9981 | 38.3 |
| 35S LCAT2 | pCGN9981 | 38.5 |
| 35S LCAT2 | pCGN9981 | 39.1 |

In light of the detailed description of the invention and the examples presented above, it can be appreciated that the several aspects of the invention are achieved.

It is to be understood that the present invention has been described in detail by way of illustration and example in order to acquaint others skilled in the art with the invention, its principles, and its practical application. Particular formulations and processes of the present invention are not limited to the descriptions of the specific embodiments presented, but rather the descriptions and examples should be viewed in terms of the claims that follow and their equivalents. While some of the examples and descriptions above include some conclusions about the way the invention may function, the inventors do not intend to be bound by those conclusions and functions, but put them forth only as possible explanations.

It is to be further understood that the specific embodiments of the present invention as set forth are not intended as being exhaustive or limiting of the invention, and that many alternatives, modifications, and variations will be apparent to those of ordinary skill in the art in light of the foregoing examples and detailed description. Accordingly, this invention is intended to embrace all such alternatives, modifications, and variations that fall within the spirit and scope of the following claims.

What is claimed is:

1. An isolated nucleic acid sequence comprising a coding sequence, wherein the coding sequence comprises a polynucleotide selected from the group consisting of:
   (a) an isolated polynucleotide encoding the polypeptide of SEQ ID NO: 5;
   (b) an isolated polynucleotide comprising the nucleic acid sequence of SEQ ID NO: 4;
   (c) an isolated polynucleotide having at least 95% sequence identity with the nucleic acid sequence of SEQ ID NO: 4;
   (d) an isolated polynucleotide complementary to the polynucleotide of (a), (b), or (c); and
   (e) an isolated polynucleotide that hybridizes under conditions of 5×SSC, 50% formamide and 42° C. to the nucleic acid sequence of SEQ ID NO: 4, wherein the coding sequence encodes a plant acyltransferase polypeptide, and wherein the coding sequence is operably linked to a heterologous regulatory sequence functional in plants.

2. A recombinant nucleic acid construct comprising a heterologous regulatory sequence operably linked to the polynucleotide of claim 1 further comprising a termination sequence.

3. The recombinant construct of claim 2, wherein said regulatory sequence is functional in a plant cell.

4. The recombinant construct of claim 2 wherein said polynucleotide comprises SEQ ID NO: 4.

5. The recombinant construct of claim 2, wherein said regulatory sequence comprises a constitutive promoter.

6. The recombinant construct of claim 2, wherein said regulatory sequence comprises an inducible promoter.

7. The recombinant construct of claim 2, wherein said regulatory sequence is selected from the group consisting of a tissue specific promoter, a developmentally regulated promoter, an organelle specific promoter, and a seed specific promoter.

8. A host cell containing the recombinant construct of claim 2.

9. The host cell of claim 8, wherein said host cell is selected from the group consisting of plant cells and bacteriophage.

10. The host cell of claim 8, wherein said host cell is a plant cell.

11. The host cell of claim 8, wherein said host cell expresses the polypeptide encoded by said recombinant construct of claim 2.

12. A plant comprising at least one host cell of claim 8.

13. A progeny plant of the plant of claim 12, wherein the progeny contains said recombinant construct of claim 2.

14. A seed from the plant of claim 12, wherein the seed contains said recombinant construct of claim 2.

15. A plant comprising the recombinant construct of claim 2.

16. The progeny of the plant of claim 15, wherein the progeny contain said recombinant construct of claim 2.

17. A seed from the plant of claim 15, wherein the seed contains said recombinant construct of claim 2.

18. A plant comprising a recombinant construct containing a heterologous regulatory sequence operably linked to a polynucleotide selected from the group consisting of:

(a) an isolated polynucleotide encoding the polypeptide of SEQ ID NO: 5;

(b) an isolated polynucleotide comprising the nucleic acid sequence of SEQ ID NO: 4;

an isolated polynucleotide having at least 95% sequence identity with the nucleic acid sequence of SEQ ID NO: 4;

(d) an isolated polynucleotide complementary to the polynucleotide of (a), (b), or (c); and (e) an isolated polynucleotide that hybridizes under conditions of 5×SSC, 50% formamide and 42° C. to SEQ ID NO: 4, wherein expression of said recombinant construct results in an increased production of oil by said plant as compared to the same plant without said recombinant construct.

19. The plant of claim 18, wherein said polynucleotide comprises SEQ ID NO: 4.

20. The plant of claim 18, wherein said regulatory sequence is a tissue specific promoter.

21. The plant of claim 18, wherein said regulatory sequence is a seed specific promoter.

22. The isolated nucleic acid of claim 1, wherein the nucleic acid sequence comprises the nucleic acid sequence of SEQ ID NO:4.

23. The isolated nucleic acid of claim 1, wherein the nucleic acid sequence encodes the polypeptide sequence of SEQ ID NO: 5.

24. The isolated nucleic acid of claim 1, wherein the nucleic acid has at least 95% sequence identity with SEQ ID NO: 4.

25. The isolated nucleic acid of claim 1, wherein the nucleic acid hybridizes under conditions of 5×SSC, 50% formamide and 42° C. to the nucleic acid sequence of SEQ ID NO: 4.

* * * * *

UNITED STATES PATENT AND TRADEMARK OFFICE
CERTIFICATE OF CORRECTION

PATENT NO. : 7,157,619 B1 Page 1 of 1
APPLICATION NO. : 09/651651
DATED : January 2, 2007
INVENTOR(S) : Lassner et al.

It is certified that error appears in the above-identified patent and that said Letters Patent is hereby corrected as shown below:

Title page, item [57], line 11, delete "composition" and insert --compositions-- therefor.

In claim 1, column 118, line 66, after " C", delete "." therefor.

In claim 18, column 120, line 9, before "an isolated", insert --(c)-- therefor.

In claim 18, column 120, line 16, after " C", delete "." therefor.

In claim 25, column 120, line 39, after " C", delete "." therefor.

Signed and Sealed this

Third Day of July, 2007

JON W. DUDAS
*Director of the United States Patent and Trademark Office*

SEQUENCE LISTING

<160> NUMBER OF SEQ ID NOS: 80

<210> SEQ ID NO 1
<211> LENGTH: 440
<212> TYPE: PRT
<213> ORGANISM: Homo sapiens

<400> SEQUENCE: 1

Met Gly Pro Pro Gly Ser Pro Trp Gln Trp Val Thr Leu Leu Leu Gly
 1               5                  10                  15

Leu Leu Leu Pro Pro Ala Ala Pro Phe Trp Leu Asn Val Leu Phe
             20                  25                  30

Pro Pro His Thr Thr Pro Lys Ala Glu Leu Ser Asn His Thr Arg Pro
             35                  40                  45

Val Ile Leu Val Pro Gly Cys Leu Gly Asn Gln Leu Glu Ala Lys Leu
         50                  55                  60

Asp Lys Pro Asp Val Val Asn Trp Met Cys Tyr Arg Lys Thr Glu Asp
 65                  70                  75                  80

Phe Phe Thr Ile Trp Leu Asp Leu Asn Met Phe Leu Pro Leu Gly Val
                 85                  90                  95

Asp Cys Trp Ile Asp Asn Thr Arg Val Val Tyr Asn Arg Ser Ser Gly
            100                 105                 110

Leu Val Ser Asn Ala Pro Gly Val Gln Ile Arg Val Pro Gly Phe Gly
        115                 120                 125

Lys Thr Tyr Ser Val Glu Tyr Leu Asp Ser Ser Lys Leu Ala Gly Tyr
    130                 135                 140

Leu His Thr Leu Val Gln Asn Leu Val Asn Asn Gly Tyr Val Arg Asp
145                 150                 155                 160

Glu Thr Val Arg Ala Ala Pro Tyr Asp Trp Arg Leu Glu Pro Gly Gln
                165                 170                 175

Gln Glu Glu Tyr Tyr Arg Lys Leu Ala Gly Leu Val Glu Glu Met His
            180                 185                 190

Ala Ala Tyr Gly Lys Pro Val Phe Leu Ile Gly His Ser Leu Gly Cys
        195                 200                 205

Leu His Leu Leu Tyr Phe Leu Leu Arg Gln Pro Gln Ala Trp Lys Asp
    210                 215                 220

Arg Phe Ile Asp Gly Phe Ile Ser Leu Gly Ala Pro Trp Gly Gly Ser
225                 230                 235                 240

Ile Lys Pro Met Leu Val Leu Ala Ser Gly Asp Asn Gln Gly Ile Pro
                245                 250                 255

Ile Met Ser Ser Ile Lys Leu Lys Glu Glu Gln Arg Ile Thr Thr Thr
            260                 265                 270

Ser Pro Trp Met Phe Pro Ser Arg Met Ala Trp Pro Glu Asp His Val
    275                 280                 285

Phe Ile Ser Thr Pro Ser Phe Asn Tyr Thr Gly Arg Asp Phe Gln Arg
    290                 295                 300

Phe Phe Ala Asp Leu His Phe Glu Glu Gly Trp Tyr Met Trp Leu Gln
305                 310                 315                 320

Ser Arg Asp Leu Leu Ala Gly Leu Pro Ala Pro Gly Val Glu Val Tyr
                325                 330                 335

Cys Leu Tyr Gly Val Gly Leu Pro Thr Pro Arg Thr Tyr Ile Tyr Asp
            340                 345                 350

His Gly Phe Pro Tyr Thr Asp Pro Val Gly Val Leu Tyr Glu Asp Gly

```
                355                 360                 365
Asp Asp Thr Val Ala Thr Arg Ser Thr Glu Leu Cys Gly Leu Trp Gln
        370                 375                 380

Gly Arg Gln Pro Gln Pro Val His Leu Leu Pro Leu His Gly Ile Gln
385                 390                 395                 400

His Leu Asn Met Val Phe Ser Asn Leu Thr Leu Glu His Ile Asn Ala
                405                 410                 415

Ile Leu Leu Gly Ala Tyr Arg Gln Gly Pro Pro Ala Ser Pro Thr Ala
            420                 425                 430

Ser Pro Glu Pro Pro Pro Pro Glu
        435                 440

<210> SEQ ID NO 2
<211> LENGTH: 1299
<212> TYPE: DNA
<213> ORGANISM: Arabidopsis thaliana

<400> SEQUENCE: 2
atgaaaaaaa tatcttcaca ttattcggta gtcatagcga tactcgttgt ggtgacgatg      60
acctcgatgt gtcaagctgt gggtagcaac gtgtacccct tgattctggt tccaggaaac     120
ggaggtaacc agctagaggt acggctggac agagaataca agccaagtag tgtctggtgt     180
agcagctggt tatatccgat tcataagaag agtggtggat ggtttaggct atggttcgat     240
gcagcagtgt tattgtctcc cttcaccagg tgcttcagcg atcgaatgat gttgtactat     300
gaccctgatt tggatgatta ccaaaatgct cctggtgtcc aaacccgggt tcctcatttc     360
ggttcgacca aatcacttct atacctcgac cctcgtctcc gagatgccac atcttacatg     420
gaacatttgg tgaaagctct agagaaaaaa tgcgggtatg ttaacgacca aaccatccta     480
ggagctccat atgatttcag gtacggcctg gctgcttcgg ccacccgtc ccgtgtagcc     540 tcacagttcc tacaagacct caaacaattg gtggaaaaaa ctagcagcga gaacgaagga     600
aagccagtga tactcctctc ccatagccta ggaggacttt cgtcctcca tttcctcaac     660 cgtaccaccc cttcatggcg ccgcaagtac atcaaacact tgttgcact cgctgcgcca     720 tggggtggga cgatctctca gatgaagaca tttgcttctg caacacact cggtgtccct     780 ttagttaacc ctttgctggt cagacggcat cagaggacct ccgagagtaa ccaatggcta     840
cttccatcta ccaaagtgtt tcacgacaga actaaaccgc ttgtcgtaac tccccaggtt     900
aactacacag cttacgagat ggatcggttt tttgcagaca ttggattctc acaaggagtt     960
gtgccttaca agacaagagt gttgcctta acagaggagc tgatgactcc gggagtgcca    1020
gtcacttgca tatatgggag aggagttgat acaccggagg ttttgatgta tggaaaagga    1080
ggattcgata agcaaccaga gattaagtat ggagatggag atgggacggt taatttggcg    1140
agcttagcag ctttgaaagt cgatagcttg aacaccgtag agattgatgg agtttcgcat    1200
acatctatac ttaaagacga gatcgcactt aaagagatta tgaagcagat ttcaattatt    1260
aattatgaat tagccaatgt taatgccgtc aatgaatga                          1299

<210> SEQ ID NO 3
<211> LENGTH: 432
<212> TYPE: PRT
<213> ORGANISM: Arabidopsis thaliana

<400> SEQUENCE: 3

Met Lys Lys Ile Ser Ser His Tyr Ser Val Val Ile Ala Ile Leu Val
1                 5                  10                  15
```

```
Val Val Thr Met Thr Ser Met Cys Gln Ala Val Gly Ser Asn Val Tyr
             20                  25                  30

Pro Leu Ile Leu Val Pro Gly Asn Gly Asn Gln Leu Glu Val Arg
         35                  40                  45

Leu Asp Arg Glu Tyr Lys Pro Ser Ser Val Trp Cys Ser Ser Trp Leu
     50                  55                  60

Tyr Pro Ile His Lys Lys Ser Gly Gly Trp Phe Arg Leu Trp Phe Asp
 65                  70                  75                  80

Ala Ala Val Leu Leu Ser Pro Phe Thr Arg Cys Phe Ser Asp Arg Met
                 85                  90                  95

Met Leu Tyr Tyr Asp Pro Asp Leu Asp Asp Tyr Gln Asn Ala Pro Gly
             100                 105                 110

Val Gln Thr Arg Val Pro His Phe Gly Ser Thr Lys Ser Leu Leu Tyr
             115                 120                 125

Leu Asp Pro Arg Leu Arg Asp Ala Thr Ser Tyr Met Glu His Leu Val
         130                 135                 140

Lys Ala Leu Glu Lys Lys Cys Gly Tyr Val Asn Asp Gln Thr Ile Leu
145                 150                 155                 160

Gly Ala Pro Tyr Asp Phe Arg Tyr Gly Leu Ala Ala Ser Gly His Pro
                 165                 170                 175

Ser Arg Val Ala Ser Gln Phe Leu Gln Asp Leu Lys Gln Leu Val Glu
             180                 185                 190

Lys Thr Ser Ser Glu Asn Glu Gly Lys Pro Val Ile Leu Leu Ser His
         195                 200                 205

Ser Leu Gly Gly Leu Phe Val Leu His Phe Leu Asn Arg Thr Thr Pro
     210                 215                 220

Ser Trp Arg Arg Lys Tyr Ile Lys His Phe Val Ala Leu Ala Ala Pro
225                 230                 235                 240

Trp Gly Gly Thr Ile Ser Gln Met Lys Thr Phe Ala Ser Gly Asn Thr
                 245                 250                 255

Leu Gly Val Pro Leu Val Asn Pro Leu Leu Val Arg Arg His Gln Arg
             260                 265                 270

Thr Ser Glu Ser Asn Gln Trp Leu Leu Pro Ser Thr Lys Val Phe His
         275                 280                 285

Asp Arg Thr Lys Pro Leu Val Val Thr Pro Gln Val Asn Tyr Thr Ala
     290                 295                 300

Tyr Glu Met Asp Arg Phe Phe Ala Asp Ile Gly Phe Ser Gln Gly Val
305                 310                 315                 320

Val Pro Tyr Lys Thr Arg Val Leu Pro Leu Thr Glu Glu Leu Met Thr
                 325                 330                 335

Pro Gly Val Pro Val Thr Cys Ile Tyr Gly Arg Gly Val Asp Thr Pro
             340                 345                 350

Glu Val Leu Met Tyr Gly Lys Gly Phe Asp Lys Gln Pro Glu Ile
         355                 360                 365

Lys Tyr Gly Asp Gly Asp Gly Thr Val Asn Leu Ala Ser Leu Ala Ala
     370                 375                 380

Leu Lys Val Asp Ser Leu Asn Thr Val Glu Ile Asp Gly Val Ser His
385                 390                 395                 400

Thr Ser Ile Leu Lys Asp Glu Ile Ala Leu Lys Glu Ile Met Lys Gln
                 405                 410                 415

Ile Ser Ile Ile Asn Tyr Glu Leu Ala Asn Val Asn Ala Val Asn Glu
             420                 425                 430
```

<210> SEQ ID NO 4
<211> LENGTH: 1641
<212> TYPE: DNA
<213> ORGANISM: Arabidopsis thaliana

<400> SEQUENCE: 4

| | | | | | |
|---|---|---|---|---|---|
| atgggagcga | attcgaaatc | agtaacggct | tccttcaccg | tcatcgccgt | tttttcttg | 60 |
| atttgcggtg | gccgaactgc | ggtggaggat | gagaccgagt | tcacggcga | ctactcgaag | 120 |
| ctatcgggta | taatcattcc | gggatttgcg | tcgacgcagc | tacgagcgtg | gtcgatcctt | 180 |
| gactgtccat | acactccgtt | ggacttcaat | ccgctcgacc | tcgtatggct | agacaccact | 240 |
| aagcttcttt | ctgctgtcaa | ctgctggttt | aagtgtatgg | tgctagatcc | ttataatcaa | 300 |
| acagaccatc | ccgagtgtaa | gtcacggcct | gacagtggtc | tttcagccat | acagaattg | 360 |
| gatccaggtt | acataacagg | tcctctttct | actgtctgga | agagtggct | taagtggtgt | 420 |
| gttgagtttg | gtatagaagc | aaatgcaatt | gtcgctgttc | catacgattg | gagattgtca | 480 |
| ccaaccaaat | tggaagagcg | tgaccttttac | tttcacaagc | tcaagttgac | ctttgaaact | 540 |
| gctttaaaac | tccgtggcgg | cccttctata | gtatttgccc | attcaatggg | taataatgtc | 600 |
| ttcagatact | ttctggaatg | gctgaggcta | gaaattgcac | caaaacatta | tttgaagtgg | 660 |
| cttgatcagc | atatccatgc | ttatttcgct | gttggagctc | ctcttcttgg | ttctgttgag | 720 |
| gcaatcaaat | ctactctctc | tggtgtaacg | tttggccttc | ctgtttctga | gggaactgct | 780 |
| cggttgttgt | ccaattcttt | tgcgtcgtca | ttgtggctta | tgccattttc | aaagaattgc | 840 |
| aagggtgata | acacatcctg | gacgcatttt | tctgggggtg | ctgcaaagaa | agataagcgc | 900 |
| gtataccact | gtgatgaaga | ggaatatcaa | tcaaaatatt | ctggctggcc | gacaaatatt | 960 |
| attaacattg | aaattccttc | cactagcgtt | acagaaacag | ctctagtcaa | catgaccagc | 1020 |
| atggaatgtg | gccttcccac | cctttttgtct | ttcacagccc | gtgaactagc | agatgggact | 1080 |
| cttttcaaag | caatagaaga | ctatgaccca | gatagcaaga | ggatgttaca | ccagttaaag | 1140 |
| aagttgtatc | atgatgaccc | tgttttaat | cctctgactc | cttgggagag | accacctata | 1200 |
| aaaaatgtat | tttgcatata | tggtgctcat | ctaaagacag | aggttggtta | ttactttgcc | 1260 |
| ccaagtggca | aaccttatcc | tgataattgg | atcatcacgg | atatcattta | cgaaactgaa | 1320 |
| ggttccctcg | tgtcaaggtc | tggaactgtg | gttgatggga | acgctggacc | tataactggg | 1380 |
| gatgagacgg | tacctatca | ttcactctct | tggtgcaaga | attggctcgg | acctaaagtt | 1440 |
| aacataacaa | tggctccca | gccagaacac | gatggaagcg | acgtacatgt | ggaactaaat | 1500 |
| gttgatcatg | agcatgggtc | agacatcata | gctaacatga | caaaagcacc | aagggttaag | 1560 |
| tacataacct | tttatgaaga | ctctgagagc | attccgggga | agagaaccgc | agtctgggag | 1620 |
| cttgataaaa | gtgggtatta | a | | | | 1641 |

<210> SEQ ID NO 5
<211> LENGTH: 546
<212> TYPE: PRT
<213> ORGANISM: Arabidopsis thaliana

<400> SEQUENCE: 5

Met Gly Ala Asn Ser Lys Ser Val Thr Ala Ser Phe Thr Val Ile Ala
 1               5                  10                  15

Val Phe Phe Leu Ile Cys Gly Gly Arg Thr Ala Val Glu Asp Glu Thr
             20                  25                  30

Glu Phe His Gly Asp Tyr Ser Lys Leu Ser Gly Ile Ile Ile Pro Gly

-continued

```
            35                  40                  45
Phe Ala Ser Thr Gln Leu Arg Ala Trp Ser Ile Leu Asp Cys Pro Tyr
 50                  55                  60

Thr Pro Leu Asp Phe Asn Pro Leu Asp Leu Val Trp Leu Asp Thr Thr
 65                  70                  75                  80

Lys Leu Leu Ser Ala Val Asn Cys Trp Phe Lys Cys Met Val Leu Asp
                     85                  90                  95

Pro Tyr Asn Gln Thr Asp His Pro Glu Cys Lys Ser Arg Pro Asp Ser
                    100                 105                 110

Gly Leu Ser Ala Ile Thr Glu Leu Asp Pro Gly Tyr Ile Thr Gly Pro
                    115                 120                 125

Leu Ser Thr Val Trp Lys Glu Trp Leu Lys Trp Cys Val Glu Phe Gly
                    130                 135                 140

Ile Glu Ala Asn Ala Ile Val Ala Val Pro Tyr Asp Trp Arg Leu Ser
145                 150                 155                 160

Pro Thr Lys Leu Glu Glu Arg Asp Leu Tyr Phe His Lys Leu Lys Leu
                    165                 170                 175

Thr Phe Glu Thr Ala Leu Lys Leu Arg Gly Gly Pro Ser Ile Val Phe
                    180                 185                 190

Ala His Ser Met Gly Asn Asn Val Phe Arg Tyr Phe Leu Glu Trp Leu
                    195                 200                 205

Arg Leu Glu Ile Ala Pro Lys His Tyr Leu Lys Trp Leu Asp Gln His
                    210                 215                 220

Ile His Ala Tyr Phe Ala Val Gly Ala Pro Leu Leu Gly Ser Val Glu
225                 230                 235                 240

Ala Ile Lys Ser Thr Leu Ser Gly Val Thr Phe Gly Leu Pro Val Ser
                    245                 250                 255

Glu Gly Thr Ala Arg Leu Leu Ser Asn Ser Phe Ala Ser Ser Leu Trp
                    260                 265                 270

Leu Met Pro Phe Ser Lys Asn Cys Lys Gly Asp Asn Thr Ser Trp Thr
                    275                 280                 285

His Phe Ser Gly Gly Ala Ala Lys Lys Asp Lys Arg Val Tyr His Cys
                    290                 295                 300

Asp Glu Glu Glu Tyr Gln Ser Lys Tyr Ser Gly Trp Pro Thr Asn Ile
305                 310                 315                 320

Ile Asn Ile Glu Ile Pro Ser Thr Ser Val Thr Glu Thr Ala Leu Val
                    325                 330                 335

Asn Met Thr Ser Met Glu Cys Gly Leu Pro Thr Leu Leu Ser Phe Thr
                    340                 345                 350

Ala Arg Glu Leu Ala Asp Gly Thr Leu Phe Lys Ala Ile Glu Asp Tyr
                    355                 360                 365

Asp Pro Asp Ser Lys Arg Met Leu His Gln Leu Lys Lys Leu Tyr His
                    370                 375                 380

Asp Asp Pro Val Phe Asn Pro Leu Thr Pro Trp Glu Arg Pro Pro Ile
385                 390                 395                 400

Lys Asn Val Phe Cys Ile Tyr Gly Ala His Leu Lys Thr Glu Val Gly
                    405                 410                 415

Tyr Tyr Phe Ala Pro Ser Gly Lys Pro Tyr Pro Asp Asn Trp Ile Ile
                    420                 425                 430

Thr Asp Ile Ile Tyr Glu Thr Glu Gly Ser Leu Val Ser Arg Ser Gly
                    435                 440                 445

Thr Val Val Asp Gly Asn Ala Gly Pro Ile Thr Gly Asp Glu Thr Val
                    450                 455                 460
```

```
Pro Tyr His Ser Leu Ser Trp Cys Lys Asn Trp Leu Gly Pro Lys Val
465                 470                 475                 480

Asn Ile Thr Met Ala Pro Gln Pro Glu His Asp Gly Ser Asp Val His
                485                 490                 495

Val Glu Leu Asn Val Asp His Glu His Gly Ser Asp Ile Ile Ala Asn
            500                 505                 510

Met Thr Lys Ala Pro Arg Val Lys Tyr Ile Thr Phe Tyr Glu Asp Ser
        515                 520                 525

Glu Ser Ile Pro Gly Lys Arg Thr Ala Val Trp Glu Leu Asp Lys Ser
    530                 535                 540

Gly Tyr
545

<210> SEQ ID NO 6
<211> LENGTH: 1608
<212> TYPE: DNA
<213> ORGANISM: Arabidopsis thaliana

<400> SEQUENCE: 6
atgtctctat tactggaaga gatcattaga tcagtagagg ctttgctgaa gctcagaaat      60
cggaatcaag aaccctatgt tgacccgaat ctaaacccgg ttcttctagt tccaggaatc    120
gctggatcaa ttctaaacgc cgttgatcat gagaacggga cgaagaacg  tgtttgggtt    180 aggatctttg gtgctgatca tgagtttcga acaaagatgt ggtctcgatt tgatccttca    240
actggtaaaa cgatatctct tgatccaaaa acgagtattg ttgttcctca agacagagct    300
gggctacatg caattgatgt cttagaccct gatatgattg ttggccgtga gtctgtgtac    360
tatttccatg agatgattgt tgagatgatc ggatggggat ttgaagaagg gaaaacccct    420
tttggttttg gttatgattt ccgccaaagc aacagactgc aggaaacgtt ggaccagttt    480
gctaaaaagt tggaaactgt ttataaagcc tcaggagaga agaagattaa tgttattagt    540
cattctatgg gaggactatt ggtgaaatgt ttcatgggtc tgcatagtga tatattcgag    600
aagtatgtac agaattggat tgctattgct gctccatttc gaggtgctcc tggatatatc    660
acatcgactt tattgaatgg aatgtcgttt gtcaatggtt gggaacagaa cttttttcgtc    720 tctaagtgga gcatgcatca gctgcttatt gagtgtccat ccatatatga gctgatgtgt    780
tgtccgtatt taaatgggaa gctccctccc gtcttagagc tgtggagaga gaaagagagc    840
aatgatggag ttggaacctc tgatgttgtt cttgagtctt accgtagcct ggagagcctt    900
gaagttttta cgaaatctct ttcgaataat acagctgatt attgtggaga gtcgatcgat    960 cttccttttta actggaagat catggagtgg gctcacaaaa ccaagcaagt attagcctct   1020
gccaagctgc ctccgaaagt taaattctat aacatatatg ggaccaatct agaaacccct   1080
catagtgttt gctatgggaa tgagaagatg cccgttaaag atctaacgaa tctaagatac   1140
ttccagccga catatatatg cgtggatggt gatggcacag tcccgatgga atctgccatg   1200
gcggatgggc ttgaagcagt agcaagagtt ggagtccctg gtgagcaccg aggaatcctc   1260
aacgatcacc gtgtcttccg aatgctcaaa aaatggctaa atgtaggcga accagacccg   1320
ttctacaacc cagtaaacga ttatgtcatc cttcccacca catatgaatt tgagaaattc   1380
catgagaatg gactcgaggt tgcttccgtg aaagaatcgt gggacatcat atcagatgac   1440
aacaatatcg gcacaaccgg gtcaaccgtg aactccatat cagtctctca acctggagat   1500
gatcaaaacc ctcaagctga agctcgtgca accttaaccg tccaaccaca aagcgatggt   1560
```
agacaacatg tagagctcaa tgctgtaagt gtctctgttg atgcataa            1608

<210> SEQ ID NO 7
<211> LENGTH: 535
<212> TYPE: PRT
<213> ORGANISM: Arabidopsis thaliana

<400> SEQUENCE: 7

```
Met Ser Leu Leu Glu Glu Ile Ile Arg Ser Val Glu Ala Leu Leu
 1               5                  10                  15

Lys Leu Arg Asn Arg Asn Gln Glu Pro Tyr Val Asp Pro Asn Leu Asn
             20                  25                  30

Pro Val Leu Val Pro Gly Ile Ala Gly Ser Ile Leu Asn Ala Val
         35                  40                  45

Asp His Glu Asn Gly Asn Glu Glu Arg Val Trp Val Arg Ile Phe Gly
     50                  55                      60

Ala Asp His Glu Phe Arg Thr Lys Met Trp Ser Arg Phe Asp Pro Ser
 65                  70                  75                  80

Thr Gly Lys Thr Ile Ser Leu Asp Pro Lys Thr Ser Ile Val Val Pro
                 85                  90                  95

Gln Asp Arg Ala Gly Leu His Ala Ile Asp Val Leu Asp Pro Asp Met
            100                 105                 110

Ile Val Gly Arg Glu Ser Val Tyr Tyr Phe His Glu Met Ile Val Glu
        115                 120                 125

Met Ile Gly Trp Gly Phe Glu Glu Gly Lys Thr Leu Phe Gly Phe Gly
    130                 135                 140

Tyr Asp Phe Arg Gln Ser Asn Arg Leu Gln Glu Thr Leu Asp Gln Phe
145                 150                 155                 160

Ala Lys Lys Leu Glu Thr Val Tyr Lys Ala Ser Gly Glu Lys Lys Ile
                165                 170                 175

Asn Val Ile Ser His Ser Met Gly Gly Leu Leu Val Lys Cys Phe Met
            180                 185                 190

Gly Leu His Ser Asp Ile Phe Glu Lys Tyr Val Gln Asn Trp Ile Ala
        195                 200                 205

Ile Ala Ala Pro Phe Arg Gly Ala Pro Gly Tyr Ile Thr Ser Thr Leu
    210                 215                 220

Leu Asn Gly Met Ser Phe Val Asn Gly Trp Glu Gln Asn Phe Phe Val
225                 230                 235                 240

Ser Lys Trp Ser Met His Gln Leu Leu Ile Glu Cys Pro Ser Ile Tyr
                245                 250                 255

Glu Leu Met Cys Cys Pro Tyr Phe Lys Trp Glu Leu Pro Pro Val Leu
            260                 265                 270

Glu Leu Trp Arg Glu Lys Glu Ser Asn Asp Gly Val Gly Thr Ser Asp
        275                 280                 285

Val Val Leu Glu Ser Tyr Arg Ser Leu Glu Ser Leu Glu Val Phe Thr
    290                 295                 300

Lys Ser Leu Ser Asn Asn Thr Ala Asp Tyr Cys Gly Glu Ser Ile Asp
305                 310                 315                 320

Leu Pro Phe Asn Trp Lys Ile Met Glu Trp Ala His Lys Thr Lys Gln
                325                 330                 335

Val Leu Ala Ser Ala Lys Leu Pro Pro Lys Val Lys Phe Tyr Asn Ile
            340                 345                 350

Tyr Gly Thr Asn Leu Glu Thr Pro His Ser Val Cys Tyr Gly Asn Glu
        355                 360                 365
```

```
Lys Met Pro Val Lys Asp Leu Thr Asn Leu Arg Tyr Phe Gln Pro Thr
    370                 375                 380
Tyr Ile Cys Val Asp Gly Asp Gly Thr Val Pro Met Glu Ser Ala Met
385                 390                 395                 400
Ala Asp Gly Leu Glu Ala Val Ala Arg Val Gly Val Pro Gly Glu His
                405                 410                 415
Arg Gly Ile Leu Asn Asp His Arg Val Phe Arg Met Leu Lys Lys Trp
                420                 425                 430
Leu Asn Val Gly Glu Pro Asp Pro Phe Tyr Asn Pro Val Asn Asp Tyr
                435                 440                 445
Val Ile Leu Pro Thr Thr Tyr Glu Phe Glu Lys Phe His Glu Asn Gly
    450                 455                 460
Leu Glu Val Ala Ser Val Lys Glu Ser Trp Asp Ile Ile Ser Asp Asp
465                 470                 475                 480
Asn Asn Ile Gly Thr Thr Gly Ser Thr Val Asn Ser Ile Ser Val Ser
                485                 490                 495
Gln Pro Gly Asp Asp Gln Asn Pro Gln Ala Glu Ala Arg Ala Thr Leu
                500                 505                 510
Thr Val Gln Pro Gln Ser Asp Gly Arg Gln His Val Glu Leu Asn Ala
                515                 520                 525
Val Ser Val Ser Val Asp Ala
    530                 535

<210> SEQ ID NO 8
<211> LENGTH: 1344
<212> TYPE: DNA
<213> ORGANISM: Arabidopsis thaliana

<400> SEQUENCE: 8
atgggctgga ttccgtgtcc gtgctgggga accaacgacg atgaaaacgc cggcgaggtg      60
gcggatcgtg atccggtgct tctagtatct ggaattggag ctctattct gcattctaag      120
aagaagaatt caaagtctga aattcgggtt tgggtccgaa tatttctagc taaccttgcc      180
tttaagcaga gcctctggtc tctctataat cccaaaactg ttatacaga gccgttggat      240
gataatattg aagtattggt ccctgatgat gaccatggac tctatgcaat tgacattcta      300
gatccctctt ggtttgtaaa gctttgtcac ttgacggagg tttatcactt tcacgatatg      360
atagaaatgc tggttggatg cggttataag aaggggacta cattattcgg ttatggttac      420
gatttccgtc aaagcaatag gatcgatcta cttatactag gtctgaagaa gaagctggaa      480
actgcatata acgttcaggg gggagaaaaa gtcactatca tctcccattc aatgggagga      540
cttatggttt catgtttcat gtatctccat ccggaggcat tttccaagta tgtaaataaa      600
tggattacaa ttgcaacacc tttccaagga gcaccagggt gcatcaatga ttcaatcttg      660
actggagtgc aatttgtgga agggttagaa agtttctttt ttgtgtcacg ttggacgatg      720
caccaactgt tggtcgaatg cccatctata tatgagatga tggcaaatcc agactttaag      780
tggaaaaagc aaccagagat tcgagtttgg cgtaagaaat ctgaaaacga cgttgatact      840
tctgtagaac tggaatcatt tggcttaatc gagagtattg atctattcaa cgatgcatta      900
aaaaataacg agctaagcta tggtgggaat aaaatagctt tgcccttaa ctttgctatc      960
ctcgactggg ctgctaagac aagagaaatt ctcaacaaag cgcaacttcc tgatggagtg     1020
tccttctata acatatatgg agtgtcactt aatacaccct tgatgtttg ttatggcaca     1080
gagacttctc cgatagacga tttgtctgaa atatgtcaaa ctatgcctga gtatacatat     1140
```

-continued

```
gtagatggag atggaactgt ccctgctgaa tcagctgcag ctgctcagtt taaagcagtt    1200
gctagcgtag gagtttcggg tagccaccgc gggcttctcc gtgatgaaag agtgtttgag    1260
ctcattcaac aatggttagg agttgagccc aagaaggcta acggaagca tttaaggact    1320 cacaaagtag ttgattctgg ttaa                                          1344
```

<210> SEQ ID NO 9
<211> LENGTH: 447
<212> TYPE: PRT
<213> ORGANISM: Arabidopsis thaliana

<400> SEQUENCE: 9

| | | | | | | | | | | | | | | |
|---|---|---|---|---|---|---|---|---|---|---|---|---|---|---|
| Met | Gly | Trp | Ile | Pro | Cys | Pro | Cys | Trp | Gly | Thr | Asn | Asp | Glu | Asn |
| 1 | | | | 5 | | | | | 10 | | | | | 15 |
| Ala | Gly | Glu | Val | Ala | Asp | Arg | Asp | Pro | Val | Leu | Leu | Val | Ser | Gly | Ile |
| | | | 20 | | | | | 25 | | | | | 30 | |
| Gly | Gly | Ser | Ile | Leu | His | Ser | Lys | Lys | Asn | Ser | Lys | Ser | Glu | Ile |
| | | | 35 | | | | 40 | | | | | 45 | | |
| Arg | Val | Trp | Val | Arg | Ile | Phe | Leu | Ala | Asn | Leu | Ala | Phe | Lys | Gln | Ser |
| | 50 | | | | | 55 | | | | | 60 | | | | |
| Leu | Trp | Ser | Leu | Tyr | Asn | Pro | Lys | Thr | Gly | Tyr | Thr | Glu | Pro | Leu | Asp |
| 65 | | | | | 70 | | | | | 75 | | | | | 80 |
| Asp | Asn | Ile | Glu | Val | Leu | Val | Pro | Asp | Asp | His | Gly | Leu | Tyr | Ala |
| | | | | 85 | | | | | 90 | | | | | 95 |
| Ile | Asp | Ile | Leu | Asp | Pro | Ser | Trp | Phe | Val | Lys | Leu | Cys | His | Leu | Thr |
| | | | 100 | | | | | 105 | | | | | 110 | | |
| Glu | Val | Tyr | His | Phe | His | Asp | Met | Ile | Glu | Met | Leu | Val | Gly | Cys | Gly |
| | | 115 | | | | | 120 | | | | | 125 | | | |
| Tyr | Lys | Lys | Gly | Thr | Thr | Leu | Phe | Gly | Tyr | Gly | Tyr | Asp | Phe | Arg | Gln |
| | 130 | | | | | 135 | | | | | 140 | | | | |
| Ser | Asn | Arg | Ile | Asp | Leu | Leu | Ile | Leu | Gly | Leu | Lys | Lys | Lys | Leu | Glu |
| 145 | | | | | 150 | | | | | 155 | | | | | 160 |
| Thr | Ala | Tyr | Lys | Arg | Ser | Gly | Gly | Arg | Lys | Val | Thr | Ile | Ile | Ser | His |
| | | | 165 | | | | | 170 | | | | | 175 | | |
| Ser | Met | Gly | Gly | Leu | Met | Val | Ser | Cys | Phe | Met | Tyr | Leu | His | Pro | Glu |
| | | | 180 | | | | | 185 | | | | | 190 | | |
| Ala | Phe | Ser | Lys | Tyr | Val | Asn | Lys | Trp | Ile | Thr | Ile | Ala | Thr | Pro | Phe |
| | | 195 | | | | | 200 | | | | | 205 | | | |
| Gln | Gly | Ala | Pro | Gly | Cys | Ile | Asn | Asp | Ser | Ile | Leu | Thr | Gly | Val | Gln |
| | 210 | | | | | 215 | | | | | 220 | | | | |
| Phe | Val | Glu | Gly | Leu | Glu | Ser | Phe | Phe | Val | Ser | Arg | Trp | Thr | Met |
| 225 | | | | | 230 | | | | | 235 | | | | | 240 |
| His | Gln | Leu | Leu | Val | Glu | Cys | Pro | Ser | Ile | Tyr | Glu | Met | Met | Ala | Asn |
| | | | | 245 | | | | | 250 | | | | | 255 | |
| Pro | Asp | Phe | Lys | Trp | Lys | Lys | Gln | Pro | Glu | Ile | Arg | Val | Trp | Arg | Lys |
| | | | 260 | | | | | 265 | | | | | 270 | | |
| Lys | Ser | Glu | Asn | Asp | Val | Asp | Thr | Ser | Val | Glu | Leu | Glu | Ser | Phe | Gly |
| | | 275 | | | | | 280 | | | | | 285 | | | |
| Leu | Ile | Glu | Ser | Ile | Asp | Leu | Phe | Asn | Asp | Ala | Leu | Lys | Asn | Asn | Glu |
| | 290 | | | | | 295 | | | | | 300 | | | | |
| Leu | Ser | Tyr | Gly | Gly | Asn | Lys | Ile | Ala | Leu | Pro | Phe | Asn | Phe | Ala | Ile |
| 305 | | | | | 310 | | | | | 315 | | | | | 320 |
| Leu | Asp | Trp | Ala | Ala | Lys | Thr | Arg | Glu | Ile | Leu | Asn | Lys | Ala | Gln | Leu |
| | | | | 325 | | | | | 330 | | | | | 335 | |

```
Pro Asp Gly Val Ser Phe Tyr Asn Ile Tyr Gly Val Ser Leu Asn Thr
            340                 345                 350

Pro Phe Asp Val Cys Tyr Gly Thr Glu Thr Ser Pro Ile Asp Asp Leu
            355                 360                 365

Ser Glu Ile Cys Gln Thr Met Pro Glu Tyr Thr Tyr Val Asp Gly Asp
            370                 375                 380

Gly Thr Val Pro Ala Glu Ser Ala Ala Ala Gln Phe Lys Ala Val
385                 390                 395                 400

Ala Ser Val Gly Val Ser Gly Ser His Arg Gly Leu Leu Arg Asp Glu
            405                 410                 415

Arg Val Phe Glu Leu Ile Gln Gln Trp Leu Gly Val Glu Pro Lys Lys
            420                 425                 430

Ala Lys Arg Lys His Leu Arg Thr His Lys Val Val Asp Ser Gly
            435                 440                 445

<210> SEQ ID NO 10
<211> LENGTH: 3107
<212> TYPE: DNA
<213> ORGANISM: Arabidopsis thaliana

<400> SEQUENCE: 10 ccttttgat  ctttcagctc  aatgagcttt  tctcaatttt  ttgggggaac  tgaatatgtg     60
aatttcaaag  tttccacatc  gagtttattc  acacgtcttg  aatttcgtcc  atcctcgttc    120
tgttatccag  ctttgaactc  ctcccgaccc  tgctatggat  atattaaaaa  aaaagtgttt    180
tgtgggttgc  atctttgtta  cgatctgcat  cttcttcttt  cggctcagtg  ttcatgtttt    240
tgctatggta  gagatgggca  atgttattgt  tgatggtaac  agtggtatag  ttgatagtat    300
cttaactaat  caattatctc  tttgattcag  gcctctatgt  tgggtggaac  acatgtcact    360
tgacaatgaa  actgggttgg  atccagctgg  tattagagtt  cgagctgtat  caggactcgt    420
ggctgctgac  tactttgctc  ctggctactt  tgtctgggca  gtgctgattg  ctaaccttgc    480
acatattgga  tatgaagaga  aaaatatgta  catggctgca  tatgactggc  ggctttcgtt    540
tcagaacaca  gaggttcttt  tctcatcgtt  ctttctatta  ttctgttcca  tgttacgttt    600
ctttcttcat  tacttaaggc  ttaaatatgt  ttcatgttga  attaataggt  acgtgatcag    660
actcttagcc  gtatgaaaag  taatatagag  ttgatggttt  ctaccaatgg  tggaaaaaaa    720
gcagttatag  ttccgcattc  catgggggtc  ttgtattttc  tacatttat   gaagtgggtt    780
gaggcaccag  ctcctctggg  tggcgggggt  gggccagatt  ggtgtgcaaa  gtatattaag    840
gcggtgatga  acattggtgg  accatttctt  ggtgttccaa  aagctgttgc  agggcttttc    900
tctgctgaag  caaaggatgt  tgcagttgcc  aggtattgaa  tatctgctta  tacttttgat    960
gatcagaacc  ttggctctgg  aactcaaagt  tattctacta  aatatcaatt  ctaataacat   1020
tgctatatta  tcgctgcaac  tgacattggt  tgattatttt  gctgcttatg  taactgaaac   1080
tctcttgaga  ttagacaaat  gatgaattga  taattcttac  gcattgctct  gtgatgacca   1140
gtttcttagc  ttcgacgata  acatttgtca  tactgtcttt  tggagggcat  tgaattttgc   1200
tatggaaagc  gctggagctt  ccatgcttgc  attctttacc  aattagcatt  attctgcttc   1260
tttcaatttt  cttgtatatg  catctatggt  cttttatttc  ttcttaatta  aagactcgtt   1320
ggagtagttg  ctctattagt  cgcttggttc  cttaatatag  aactttactt  tcttcgaaaa   1380
ttgcagagcg  attgcccag   gattcttaga  caccgatata  tttagacttc  agaccttgca   1440
gcatgtaatg  agaatgacac  gcacatggga  ctcaacaatg  tctatgttac  cgaagggagg   1500
```

-continued

| | | | | |
|---|---|---|---|---|
| tgacacaata | tggggcgggc | ttgattggtc | accggagaaa | ggccacacct gttgtgggaa | 1560 |
| aaagcaaaag | aacaacgaaa | cttgtggtga | agcaggtgaa | acggagtttt ccaagaaaag | 1620 |
| tcctgttaac | tatggaagga | tgatatcttt | tgggaaagaa | gtagcagagg ctgcgccatc | 1680 |
| tgagattaat | aatattgatt | tcgagtaag | gacatataaa | tcataataaa ccttgtacat | 1740 |
| tttgtgattg | tatgatgaat | atctgtacat | tttatctggt | gaagggtgct gtcaaaggtc | 1800 |
| agagtatccc | aaatcacacc | tgtcgtgacg | tgtggacaga | gtaccatgac atgggaattg | 1860 |
| ctgggatcaa | agctatcgct | gagtataagg | tctacactgc | tggtgaagct atagatctac | 1920 |
| tacattatgt | tgctcctaag | atgatggcgc | gtggtgccgc | tcatttctct tatgggattg | 1980 |
| ctgatgattt | ggatgacacc | aagtatcaag | atcccaaata | ctggtcaaat ccgttagaga | 2040 |
| caaagtaagt | gatttcttga | ttccaactgt | atccttcgtc | ctgatgcatt atcagtcttt | 2100 |
| ttgttttcgg | tcttgttgga | tatggttttc | agctcaaagc | ttacaaagct gtttctgagc | 2160 |
| ctttctcaaa | aaggcttgct | cagttatatt | gaggtgctaa | agttgataca tgtgactctt | 2220 |
| gcttataaat | cctccgtttg | gtttgttctg | cttttcaga | ttaccgaatg ctcctgagat | 2280 |
| ggaaatctac | tcattatacg | gagtggggat | accaacggaa | cgagcatacg tatacaagct | 2340 |
| taaccagtct | cccgacagtt | gcatcccctt | tcagatattc | acttctgctc acgaggagga | 2400 |
| cgaagatagc | tgtctgaaag | caggagttta | caatgtggat | ggggatgaaa cagtacctgt | 2460 |
| cctaagtgcc | gggtacatgt | gtgcaaaagc | gtggcgtggc | aagacaagat tcaacccttc | 2520 |
| cggaatcaag | acttacataa | gagaatacaa | tcactctccg | ccggctaacc tgttggaagg | 2580 |
| gcgcgggacg | cagagtggtg | cccatgttga | tatcatggga | actttgctt tgatcgaaga | 2640 |
| tatcatgagg | gttgccgccg | gaggtaacgg | gtctgatata | ggacatgacc aggtccactc | 2700 |
| tggcatattt | gaatggtcgg | agcgtattga | cctgaagctg | tgaatatcat gatctcttta | 2760 |
| agctgtcctg | tcagcttatg | tgaatccaat | actttgaaag | agagatcatc atcaattcat | 2820 |
| catcatcgtc | atcatcatga | tgctcaactc | acaaagaagc | ctgagaatga tactttggtg | 2880 |
| cgaaattctc | aatacctctt | taatattctt | attgaatgta | aattatacaa tcctatctaa | 2940 |
| tgtttgaacg | ataacgcaaa | acttgctgcg | ccatgttttgt | ttgtcttgtc aaaagcatca | 3000 |
| atttgtgggt | tatacgtagt | gtagaggatg | attcaaattt | gtgataaatt tggtaatcaa | 3060 |
| agttaattct | gaaaatgcaa | caccacatga | actatgtcac | taaggcc | 3107 |

<210> SEQ ID NO 11
<211> LENGTH: 1680
<212> TYPE: DNA
<213> ORGANISM: Arabidopsis thaliana
<220> FEATURE:
<221> NAME/KEY: unsure
<222> LOCATION: (694)
<223> OTHER INFORMATION: n=unkown

<400> SEQUENCE: 11

| | | | | |
|---|---|---|---|---|
| cgcataaggt | gttcgagtgt | ttgcagcttg | agaagttccg | agtccaagag acctggagcc | 60 |
| aaagatctga | accataaaaa | tgaccaatca | aaatccatta | agccaattca atatattcact | 120 |
| aaaaatgtta | tagttctcat | gaatactaac | ataacaagtg | aaagtaaatt taaaaatgtt | 180 |
| catggaccta | acctggcgta | acggtatgtc | tttgccttca | gcagaaagta aattactgac | 240 |
| ggctttaggg | acacctaaaa | aggcgggtcc | aatgttgacg | acggatttga tgtgtttggc | 300 |
| acaccaacct | ggaccacccc | caccgcctcc | atcaggaaga | ggtgtttcta cccatttaag | 360 |
| gaagtgaagg | aaatagatag | cccccattga | atgcggaacc | accacaactt tcttaaaccc | 420 |

-continued

```
attggtggca tacattagct cgattttgct cttcagtcta cttaacgatt ggtcacgtac      480
ctgctcggtt tcaatccaaa actatagat tagtccaaag ctctacaaca atatgtaatt       540
acatacacta aagtagctaa tcatggaggt cttatagtat atcattatca tcattctcta      600
gaccaccagt gttgtcaatg tgatcatata ggtattaata acgactaatc tgagcatacc      660
tcggtgttat ggaaagagag tctccaatca taangaggcc atgtgaaggt tcttgccttc      720
atatccaatt tttgccaaat tctctatgag aactgcccaa gcaaagtagc atggtgcgaa      780
atagtctgca gccactagtc ctgggactgc tcggacacgg attcccggtg gatcgagacc      840
ggtctcactg tctagagata agtgctccaa ccagcacaat ggcctataaa tcaaattaca      900
acaattaaac gaccaagtat acacttcaaa ctaattcaga attgagaaaa tcgaaatgct      960
aaccagaaaa tcatgtaaat caaaaaccgt aacaatcaat atatatatat atattttcca     1020
gaatccatgt taaaaccata accaaaaata tatgaaaatt tagaaatact aaaataatat     1080
gttaaaactg atattctaaa tttagtaagt tttaaaatgc aatgaaatcg tcattcatgt     1140
tttgaacata aatatatttt atagtttttgt aggacgattt tctacttcct atatagaaat    1200
caaaacttac ggtttccatt tccaaattcg aatgacattt aaaaacatat cccaaaaatc     1260
acgattaatt attaatttcc taaaaccatc catcattact tagaaaataa tattttcata    1320
aactagttgc aaaacaataa caaaacccaa agaaccatct ccacccatta accaaaatga    1380
aaatccaaag accatccata acaacaacag tataacacta cgtaaagcca attcaagaag    1440
aaaccaagct taaccaatta tacataccc taaccagacg aaccaaacca atatctgacc     1500
gggtctataa aaatatctcg aaccgaacat aacggtctaa tgtgttacct tctaagaatc    1560
tcggagaagc tagcaccccca aagacgttta cgaaagagtc cttcagcgca aggccgacct   1620
tcccaaagct cgagcccgcc ggttacaatc cccggaacaa gaatcaccgg atgaaacgcc   1680
```

<210> SEQ ID NO 12
<211> LENGTH: 264
<212> TYPE: DNA
<213> ORGANISM: Glycine max
<220> FEATURE:
<221> NAME/KEY: unsure
<222> LOCATION: (39)
<223> OTHER INFORMATION: n=unknown
<221> NAME/KEY: unsure
<222> LOCATION: (175)
<223> OTHER INFORMATION: n=unknown
<221> NAME/KEY: unsure
<222> LOCATION: (241)
<223> OTHER INFORMATION: n=unknown

<400> SEQUENCE: 12

```
ccaagaactc gatgattact tcaacactcc tggggttgng acccgggtcc ctcactttgg      60
ttccaccaac tctcttctct catctcaatc ctcgtctcaa gcatatcacc ggatacatgg     120 caccctggt agattcatta caaaagcttg gctacgctga tggtgagact ctgtntggag    180 cccctttatga ctttagatat ggtctagctg ctgaaggtca cccttcacaa gtgggttcca    240
ngttcctcaa agatctaaag aatt                                             264
```

<210> SEQ ID NO 13
<211> LENGTH: 273
<212> TYPE: DNA
<213> ORGANISM: Glycine max
<220> FEATURE:
<221> NAME/KEY: unsure
<222> LOCATION: (12)

<223> OTHER INFORMATION: n=unknown
<221> NAME/KEY: unsure
<222> LOCATION: (33)
<223> OTHER INFORMATION: n=unknown
<221> NAME/KEY: unsure
<222> LOCATION: (252)
<223> OTHER INFORMATION: n=unknown
<221> NAME/KEY: unsure
<222> LOCATION: (265)..(266)
<223> OTHER INFORMATION: n=unknown
<221> NAME/KEY: unsure
<222> LOCATION: (272)
<223> OTHER INFORMATION: n=unknown

<400> SEQUENCE: 13

```
ccaacatctg anagggtag  agtaggtatt  tcnatctatt  atccatattg  tgatgaagaa    60
ggaacaagaa gagggtctca agattgaggt  tgctacactc  acagttacag  tagttgttgt   120
gatgctgtca ttgctatgca catgtggggc  aagcaacctc  gacccttttga ttctaatacc   180
aggtaacgga gggaaccaac tagaagcaag  gttgaccaat  cagtacaagc  cctctacttt   240
catctgcgat cntggtaccc tctcannaag  ana                                 273
```

<210> SEQ ID NO 14
<211> LENGTH: 419
<212> TYPE: DNA
<213> ORGANISM: Glycine max
<220> FEATURE:
<221> NAME/KEY: unsure
<222> LOCATION: (99)
<223> OTHER INFORMATION: n=unknown
<221> NAME/KEY: unsure
<222> LOCATION: (346)
<223> OTHER INFORMATION: n=unknown
<221> NAME/KEY: unsure
<222> LOCATION: (352)
<223> OTHER INFORMATION: n=unknown
<221> NAME/KEY: unsure
<222> LOCATION: (392)
<223> OTHER INFORMATION: n=unknown
<221> NAME/KEY: unsure
<222> LOCATION: (405)
<223> OTHER INFORMATION: n=unknown
<221> NAME/KEY: unsure
<222> LOCATION: (418)
<223> OTHER INFORMATION: n=unknown

<400> SEQUENCE: 14

```
gctgcatatg attggagaat agcatttcag  aacactgagg  tgagggatca  aacactaagt    60
cggataaaaa gcaacataga acttatggtt  gctactaang  gtggaaataa  ggcagttatt   120
attccacatt caatgggggt cttgtacttc  ctacatttta  tgaaatgggt  tgaagcacca   180
gctccaatgg gtggtggggg aggaccagat  tggtgctcca  aatatataaa  ggcagttgta   240
aacattggtg gaccattttt aggtgttccc  aaggctatag  cagggctatt  ctcagctgag   300
gccaaggata ttgctgttgc caggacgata  gctccaggat  ttttanataa  cnatctgttt   360
ccgcattcaa acccttgcaa catgtaatga  anatgaaccc  gttcnttggg  actcaacna   419
```

<210> SEQ ID NO 15
<211> LENGTH: 272
<212> TYPE: DNA
<213> ORGANISM: Glycine max
<220> FEATURE:
<221> NAME/KEY: unsure
<222> LOCATION: (1)..(272)
<223> OTHER INFORMATION: n=unknown

<400> SEQUENCE: 15

```
tganttgatc ntgngaagtn attctgtgta ttanttccat gacatgaccg ttnnagatnc      60
gtaagtgang ggtntgaaga gggaaagacg cttttttggtn ttngatatga ttttcgccaa    120
agcaacaggt tgcaggaaac aatggatcgg ttggctgcna agttagaatc aanttataat    180
gccgcaggnn ggaagacaat aaacattata nttcattcta tgggcggtct tttccnngan    240
atgtttcntg tgcctgcaaa gcgatatttt ga                                  272
```

<210> SEQ ID NO 16
<211> LENGTH: 237
<212> TYPE: DNA
<213> ORGANISM: Glycine max
<220> FEATURE:
<221> NAME/KEY: unsure
<222> LOCATION: (1)..(237)
<223> OTHER INFORMATION: n=unknown

<400> SEQUENCE: 16

```
gattttcgcc aaagcaacag gttgcaggaa acaatggatc ggttggctgc aaagttagaa     60
tcaatntata atgcngcagg agggaagana ataaacatta taactcattc tatgggcggt    120
cttttggtga aatgnttcat gtgcctgcaa agcgatattt tgagaaata tgttaagaat     180 tgggttgcaa tttgtgcgcc attccagggt gcaccaggaa ccatcaattc naccttt       237
```

<210> SEQ ID NO 17
<211> LENGTH: 244
<212> TYPE: DNA
<213> ORGANISM: Glycine max
<220> FEATURE:
<221> NAME/KEY: unsure
<222> LOCATION: (1)..(244)
<223> OTHER INFORMATION: n=unknown

<400> SEQUENCE: 17

```
gattttcgcc aaagcaacag gttgcaggaa acaatggatc ggtnggctgc aaagttagaa     60
tgcaatttat aatgctgcag gagggaagaa aataaacatt ataactcatt ctatgggcgg    120
tcttttggtg aaatgtttca tgtgcctgca aagcgatatt tttgagaaat atgttaagaa   180
ttgggttgca atttgtgcgc cattccaggg tgcaccagga accatcaatt ctacctttt   240 aaat                                                                244
```

<210> SEQ ID NO 18
<211> LENGTH: 263
<212> TYPE: DNA
<213> ORGANISM: Glycine max

<400> SEQUENCE: 18

```
gatgaaacta aaccgtgggc gactaagctt gtttactcgg ttgatttatg gcaagatcaa     60
gttcgttgct tcatagaaga ggtcattggt gaaccagtct atcttgtggg caactcacta    120
ggaggattgg ttgcattgta ttttgcggca acaaccctc atttagtgaa aggtgtcgca    180
ttgcttaagc aaccctttt tgggggtttc tgccaaatcc cataaaaagt ccaagactag    240
cgaaaatatt tccatgggcc gga                                             263
```

<210> SEQ ID NO 19
<211> LENGTH: 311
<212> TYPE: DNA
<213> ORGANISM: Zea mays
<220> FEATURE:
<221> NAME/KEY: unsure
<222> LOCATION: (1)..(311)
<223> OTHER INFORMATION: n=unknown

<400> SEQUENCE: 19

```
cggacgctgg ncatgttcgg agcccccctac gacttccgct acgcgccgcc gtccccggc     60
cagacgtccg aggtgtactc ccgctacttc aaggagctga tggagctggt cgaggccgcg   120
agcgagagga cccggaagaa ggccgtcatc ctcggccaca gcttcggcgg catggtcgcg   180
ctcgagttcg tccggaacac tccgccggcg tggcggcgcg agcacatcga gcgcctcgtc   240
ctggtcgcgc cgacgctccc cggcgggttc ctggagccgg tgcgcaactt cgcgtccggg   300
acggacatcc t                                                         311
```

<210> SEQ ID NO 20
<211> LENGTH: 1155
<212> TYPE: DNA
<213> ORGANISM: Zea mays

<400> SEQUENCE: 20

```
tcgacccacg cgtccggcca caagaaccct ctcaagtcag actggtgcct cggaaagctg     60
agagccgcac tggaagacat gggataccga gacggagaca ccatgttcgg agcccccctac  120
gacttccgct acgcgccgcc gtccccggc cagacgtccg aggtgtactc ccgctacttc    180
aaggagctga tggagctggt cgaggccgca agcgagagga cccggaagaa ggccgtcatc    240
ctcggccaca gcttcggcgg catggtcgcg ctcgagttcg tccggaacac tccgccggcg    300
tggcggcgcg agcacatcga gcgcctcgtc ctggtcgcgc cgacgctccc cggcgggttc    360
ctggagccgg tgcgcaactt cgcgtccggg acggacatcc tmtacgtgcc agcgacgacg    420
ccgctggcca cgcgagccat gtgragragc ttcgagagcg ccatcgtgaa cttcccgtcg    480
ccggccgtgt tcgggcgcct gcaggcgccg ctcgtggtca ccagggagcg gaactactcc    540
gcgtccgcgc acgacatgga gcgcttcctc gccgccgtcg gctccggcga ggccgcggag    600
cccttcagga gacgggccgt ccccaagatg ggcagcttcg cggcgccgat ggtgcccatg    660
acgtacatca gcggggtcgg caacaggacg ccgctgcggc tggtgttctg gggcgacgac    720
ttcgacgcgg ccccggaggt ggcggcgtac ggggacggag atggcaagat caatttgatc    780
agcgtcttgg cgtttgagaa ggagatgcgt cggcagccgg agcagaagaa gcagttcaaa    840
tccatcaaga tcgataaggc ccagcattct acgatcgtca cggatgattt tgccctgcac    900
agggtcattc aagaaattgt tgaggccaat aatcagaaga ttccatccta aattcttcat    960
gtcatgtatg cattaccgag ctgtgggggc caatagtggg ttgggagttg ggacatcggt  1020
tccgtgctta aaacggtcgt ggtgtggtct caattcaatc gattagttat ttgttaacgt  1080
caattgcttg cctcaaaaaa aaaaaaaaaa aaaaaaaaaa aaaaaaaaaa aaaaaaaaaa  1140
aaaaaaaaar gggcg                                                   1155
```

<210> SEQ ID NO 21
<211> LENGTH: 328
<212> TYPE: DNA
<213> ORGANISM: Zea mays

<400> SEQUENCE: 21

```
gttggaatgc tcttcaactt tcttacgctc atttacattg cttttctctg cggtaaattg     60
ctggcttaaa tgcatgctgc ttgaaccccta taatcagata gaccatcccg aatgcaagtc   120
aaggcctgat agtggtcttc tgcaattaca gagctggacc ctggttatat aacaggtcct   180
ctctcttcag tatggaaaga atgggtcaaa tggtgtgtag agtttggcat tgaagctaat    240
```

-continued

| gcaattatcg ctgttccgta tgattggaga ctgcccccat caatgcttga ggagagagat | 300 |
| ctgtactttc acaattaaac aggatcag | 328 |

<210> SEQ ID NO 22
<211> LENGTH: 356
<212> TYPE: DNA
<213> ORGANISM: Zea mays

<400> SEQUENCE: 22

| gtctttctgc aattacagag ctggaccctg gttatataac aggtttcagg tcctctctct | 60 |
| tcagtatgga agaatgggt caaatggtgt gtagagtttg gcattgaagc taatgcaatt | 120 |
| atcgctgttc cgtatgattg gagactgccc ccatcaatgc ttgaggagag agatctgtac | 180 |
| tttcacaaat taaagtttgt aacacttgcc tcaacttgtt atgaagcaac caatgctata | 240 |
| catctgttag gatcagtaag agttaatggc ccatgacgga ttcaggttcc tgctcaccaa | 300 |
| cagatcccac aagcatacgg ttaccgccaa tgcctgcagt tggacagtac caaccc | 356 |

<210> SEQ ID NO 23
<211> LENGTH: 1552
<212> TYPE: DNA
<213> ORGANISM: Zea mays

<400> SEQUENCE: 23

| tcgacccacg cgtccgcaga catgatcatt ggtgatgaca ctgtgtacta ctatcatgac | 60 |
| atgatagtgg aaatgattaa atgggggatat caagaaggaa aaactctctt tggatttggt | 120 |
| tatgatttcc gtcaaagcaa caggctctca gagacacttg acagattttc taaaaagctg | 180 |
| gagtcagtgt acacagcttc tggtggaaag aagatcaatc tcattactca ttcaatgggg | 240 |
| ggattacttg tgaaatgttt catctcactg cacagtgata tatttgaaaa atatgtcaar | 300 |
| agttggatcg caattgctgc accattccar ggtgcccctg ggtamataac taccaktytg | 360 |
| ctgaatggaa tgtcttttgt craaggatgg gaaycaagat tctttatttc caaawkgkgt | 420 |
| atgcascaat tgctacttga gtgcccatca atctatgagk tgctgscaam ccctaacttt | 480 |
| ccagtggaga gacatcccac tgctacagat ttggagagag aatttggata mcagtggcaa | 540 |
| gaaaagtgcc ctgttagagt cgtatgagcc tgaggaagca ataaagatga ttaaagaggc | 600 |
| tctttccagt aatgagatca ttgctgatgg catgcatatt ccggtgcccc ttaatttgga | 660 |
| tatattgaat tgggcaaaga aacttatgat cttttatgca gtacaaagct tccggaatca | 720 |
| gtgaaattct acaacattta tgggattgat tatgatactc cacatactgt ctgctatggc | 780 |
| agtgaacagc agccggtttc aagtcttagt agcctcttat atgctcaggg aaaatacgtc | 840 |
| tatgttgatg gcgacggatc tgttcccgca gaatcagcaa aggctgacgg atttaatgca | 900 |
| gtggcaaggg ttgggggttgc tcctgaccac cggggaatcg tgtgcagtcg ccgcgcgttc | 960 |
| cggatcgtcc agcactggct gcacgccgga gaacctgacc cgttctacga cccgctgagc | 1020 |
| gactatgtca tactcccaac acgcttacga aatcgagaag catcgtgaga acacggggga | 1080 |
| tgtcacgtca gtagcggagg actggagagat catctcccct aacgacggca agaccatrrg | 1140 |
| gccaggcgag cttcctccta tggtcagcac actgaccacg agccgggaag gcaaggaggg | 1200 |
| agcactggaa gaggcgcatg ccaccgtggt cgttcacccg gagaagaagg gacggcagca | 1260 |
| tgtgcaagtt agggctgtgg gtgtcagcca tggtggctaa agccgtagga gccacgttgg | 1320 |
| ttgtctactc tatctagcag tagcagctat acctctgtgc acgcactgta aaattggatg | 1380 |
| tacatatatg gctatgacct ctgtagggat ctggttttag aagtataaat gggcaccctg | 1440 |

```
cctgcttgta aatgttcaga accgaaaaca caggccctgt tcttttttt cctttttaaa    1500 aaaaataaaa agatggtaaa ggattccatt aaaaaaaaaa aaaaaaaagg cg           1552

<210> SEQ ID NO 24
<211> LENGTH: 227
<212> TYPE: DNA
<213> ORGANISM: Zea mays
<220> FEATURE:
<221> NAME/KEY: unsure
<222> LOCATION: (1)..(227)
<223> OTHER INFORMATION: n=unknown

<400> SEQUENCE: 24
ttggttatga tttccgtcaa agcaacaggc tctcagagac acttgacaga ttttctaaaa     60
agctggagtc agtgtacaca gcttctggtg gaaagaagat caatctcatt actcattcaa    120 tgggggatt acttgtgaaa tgtntcatct cactgcacag tgatatatnt gaaaaatatg     180
tcaagagttg gntcgcaatt gcngcaccat tccaaggtgc ccctggg                  227

<210> SEQ ID NO 25
<211> LENGTH: 1587
<212> TYPE: DNA
<213> ORGANISM: Zea mays
<220> FEATURE:
<221> NAME/KEY: unsure
<222> LOCATION: (1)..(1587)
<223> OTHER INFORMATION: n=unknown

<400> SEQUENCE: 25
ggagattgtc gtgccggagg acgaccacgg cctgtttgcc atcgacattc ttgatccttc     60
ctggtttgta gaactcgacc cacgcgtccg cccaccgtcc gggagattgt cgtgccggag    120
gacgaccacg gcctgtttgc catcgacatt cttgatcctt cctggtttgt agaacttctc    180
catctgtcta tggtgtatca cttccatgat atgattgata tgctcataaa ctgtggatat    240
gagaaaggga ccacactatt tggatatggt tatgattttc gccaaagcaa caggatagac    300
aaagcgatgg ctggtttgag agcaaaactt gagacagctc ataagacctc tggagggaaa    360
aaagttaatt taatctcaca ttctatgggt ggattgctag tacgctgctt catgtctatg    420
aatcatgatg tattcactaa gtatgtcaac aaatggattt gcattgcttg tccattccaa    480
ggtgcccccg gatgcatcaa tgattctcta cttactggat tgcaatttgt ttatggtttt    540
gagagcttct ttttcgtatc tagatgggca atgcaccaat tgcttgtcga atgcccatca    600
atctatgaaa tgttaccaaa tccagaattc aagtggaagg aaaaaccaat tattcaggtt    660
tggcgtaaga accctgaaaa ggatggaact gtggagcttg ttcaatatga agcaactgat    720
tgtgtgtcct tgttcgaaga agctttaagg aataatgagc tcacgtataa cggaaagaaa    780
gtagcactac cattcaatat gtcagtcttc aaatgggcca ccaagactcg ccaaatccta    840
gacaatgctg aattaccaga tactgtgagc ttttacaata tacgggac atcttatgaa     900 actccatacg atgtatgcta tggctcagaa agctctccga ttggagattt gtcagaagtg    960
tgtcacacag tgccggcata cacttatgtg gatggagatt gcacggttcc catagaatcg   1020
gcacgggctg atgggttctc tgcgaaagaa agagttggcg tcaaggcgga ccaccgtggc   1080
ctgctgtccg atgagaacgt attcaagctt ctcaagaaat ggctcggtgt gagcgagaag   1140
aagtcagagt ggcgttgcgt gtctaaatcc tactccaaag tgacctaatt gggttgcctg   1200
tagttcttca ggaagactgt tattttggcc tttcctcctg aagagaagat gaaacaaaat   1260
```

```
tctggtgatt gtattgtatg tctgcacgat gtaaatctct gcaagctgca cggaacaagg    1320
gattagtgcc cttgtacgat gtatcattgg caggcatttn ttttttgaacc tangggcata    1380 tttntttgnc cttccactct ggacntagta aagaatatnt gaatcgacct tanttnnaan    1440
nngtctgnnn nnnnnnnnnn nnnnnnnnnn nnnnnnnnnn nnnnnnnnnn nnnnnnnnnn    1500
nnnnnnnnnn nnaaaaaaaa awgkgaagcc gntnntnntt tnaaaagnnt tttnnnaaaa    1560
aaaaaaaaaa aaaaaaaaaa aaaaaaa                                        1587

<210> SEQ ID NO 26
<211> LENGTH: 300
<212> TYPE: DNA
<213> ORGANISM: Zea mays
<220> FEATURE:
<221> NAME/KEY: unsure
<222> LOCATION: (1)..(300)
<223> OTHER INFORMATION: n=unknown

<400> SEQUENCE: 26
gacaaagcga tggctggttt gagagcaaaa cttgagacag ctcataagac ctctggaggg      60
aaaaaagtta atttaatctc acattctatg ggtggattgc tagtacgctg cttcatgtct    120
atgaatcatg atgtgagttt tcatgttttc tgtgtttttt ttgcttttgc ataaatatcc    180
atgtcaattt cccccatttt ctaggtattc actangtatg tcaacaaatg gatttgcatt    240
gcttgtccat tccaaggtaa cttatgggac atttcaattg tttattanat natggggncc    300

<210> SEQ ID NO 27
<211> LENGTH: 1240
<212> TYPE: DNA
<213> ORGANISM: Zea mays
<220> FEATURE:
<221> NAME/KEY: unsure
<222> LOCATION: (1)..(1240)
<223> OTHER INFORMATION: n=unknown

<400> SEQUENCE: 27
tcgacccacg cgtccggttc ccagttccca ccgtgtagat ggttctggta taaaatgtat      60 tgccatatttt gtaacacaga ttactatata caggttcgtg atcaaacttt gagcagaata    120
aagascaata ttgaactcat agwagsgaca aatggtggaa atagggtggt ggkmgatccc    180
acnactccat ggggtcnttn attttntgcn ttttacgnaa tggntcgaag ccctcctccg    240
tgggggcagt gggtccgaac tggntgtaga accatataaa gctgtaatga atattggagg    300
atctttctta ggagttccta aggctgttgc tgggcttttt ttcttctaag caaaagatgt    360
tgccggttgc taggtataag taatgattca tttatttaaa gcaaaaggga atagcaaaag    420
aatgaatatt attggatgct cgacaagctt gcggagcttt tgctcccaag ccatcttctg    480
gacctcacaa gtccagggag tgcctgcctc tgatcctcat catcaggaac aggctcaagt    540
atgcaccgac ggtaccgtga ggtcatttct atcctgatgc aacaccatgt acttgttgat    600
ggcaaggtca ggactgacaa gacctaccct gctgggttca tggatgtcat ttccatccct    660
aagacaaacg agaactacag gctgctttcg tcttcaccca atcagggatg aggatgccaa    720
gttcaagctc tacaaggtga ggtctgttca gtttggccag aaagacatcc cctatctgaa    780
cacctacgac gaccgcacca tccgctaccc cgacccgctc atcaaggcca acgacaccat    840
caagatcgat ctggagacca acaagatcat ggacttcatc atgtttgacg tcggcaacgt    900
ggtcatggtg atcggcagga ggaataccgg gcgtgtagga gtgatcaara taagggagaa    960
gcataagggc aacttcgaga ccatccacgt gctgcttgra gcttttttgct atgtctagtt   1020
```

-continued

```
ttctcctatt tgttgtacag gaaaacatag aatgaaattc aaatttggtg gccacaaaag      1080
tgtggagact tgatttcata taaagttagg cttaacatta gtgcaaacag ttgtatttta      1140
gtttagattt agagtacact atgtatgcgt tgtttgacaa tgcttattta tgatatattg      1200
aatggtactt atttatatta attaattaaa aaaaaaaaa                             1240
```

<210> SEQ ID NO 28
<211> LENGTH: 324
<212> TYPE: DNA
<213> ORGANISM: Zea mays

<400> SEQUENCE: 28

```
cgaatgctcc tgacatggaa atattttcca tgtacggagt aggcattcct actgaaaggg       60
catatgtcta aagttggcc ccacaggcag aatgttatat acctttccga attgacacct      120
cggctgaagg cggggaggaa aatagctgct tgaaagggg tgtttactta gccgatggtg      180
atgaaactgt tccagttctt agtgcgggct acatgtgtgc aaaaggatgg cgtggcaaaa      240 ctcgttttcaa ccctgccggc agcaagactt acgtgagaga atacagccat tcaccaccct     300
ctactctcct ggaaggcagg ggca                                             324
```

<210> SEQ ID NO 29
<211> LENGTH: 254
<212> TYPE: DNA
<213> ORGANISM: Zea mays

<400> SEQUENCE: 29

```
gaataaagag caacattgaa ctcatggtag caacaaatgg tggaaatagg gtggtggtga       60
tcccacactc catggggggtc ctctatttt tgcattttat gaaatgggtc gaagcacctc      120
ctcccatggg gggtggcggt ggtccagact ggtgtgagaa gcatattaaa gctgtaatga      180
atattggagg acctttctta ggagttccta aggctgttgc tggccttttc tcatctgaag      240
ccaaagatgt tgcc                                                        254
```

<210> SEQ ID NO 30
<211> LENGTH: 518
<212> TYPE: DNA
<213> ORGANISM: Mus musculus

<400> SEQUENCE: 30

```
tggaggacaa cgcggggtct gatacgactc actataggga atttggccct cgagcagtag       60
attcggcacg atgggcacga ggactccatc atgttcctca agctttattc ctaccgggat      120
gtcaacctgt ggtgccgcca gcgaagggtc aaggccaaag ctgtctctac agggaagaag      180
gtcagtgggg ctgctgcgag caagctgtga gctatccaga caacctgacc taccgagatc      240
tcgattactt catctttgct cctactttgt gttatgaact caactttcct cggtcccccc      300
gaatacgaga gcgctttctg ctacgacgag ttcttgagat gctcttttt acccagcttc      360 aagtggggct gatccaacag tggatggtcc ctactatcca gaactccatg gaagcccttt      420
caagagcttc tgcagttttg gagaccgcga gttctacaga gattggtgga atgctgagtc      480
tgtcaccgac ttttggcaga actggaatat ccccgtgg                              518
```

<210> SEQ ID NO 31
<211> LENGTH: 299
<212> TYPE: DNA
<213> ORGANISM: Mus musculus

```
<400> SEQUENCE: 31
ccatgatggc tcaggtccca ctggcctgga ttgtgggccg attcttccaa gggaactatg    60
gcaatgcagc tgtgtgggtg acactcatca ttgggcaacc ggtggctgtc tcatgtatgt   120
ccacgactac tacgtgctca actacgatgc cccagtgggt catgagctac tgccaaaggc   180
agccctccct aacctgggcc tggagttctg gaggggttcc tggctgcctg cacactcctc   240
ctagtctggg aggcctctct gcccctatgc gctactcctg ctcttgggga tggcatttg    299

<210> SEQ ID NO 32
<211> LENGTH: 1895
<212> TYPE: DNA
<213> ORGANISM: Artificial Sequence
<220> FEATURE:
<223> OTHER INFORMATION: Description of Artificial Sequence: Inferred
      cDNA sequence
<221> NAME/KEY: unsure
<222> LOCATION: (1)..(1895)
<223> OTHER INFORMATION: n=unknown

<400> SEQUENCE: 32
gtctggtgtg atggggacag ggagggactt cccctttaccc agcactggtg ttggctgagg    60
tgggtgctga gtctcagagc ttggcatgga gaccagacag ggctgggtct gcaagcctga   120
ggctgccgcc ctgagctcgg gctgggacgt gcccagaggt gttgggagga tctggggtga   180
gtaccctgtg gccaggacta aaggggctnc accctcctgt ccatccctcg cagatcttga   240
gcaatgcccg gttatttctg gagaacctca tcaagtatgg catccggtg gacccccatcc   300 aggtggtttc tctgttcctg aaggatccct atagctggcc cgccccatgc ctggttattg   360
cggccaatgt ctttgctgtg gctgcattcc aggttgagaa gcgcctggcg gtgggtgccc   420
tgacggagca ggcgggactg ctgctgcacg tggccaacct ggccaccatt ctgtgtttcc   480
cagcggctgt ggtcttactg gttgagtcta tcactccagt gggctccctg ctggcgctga   540
tggcgcacac catcctcttc ctcaagctct tctcctaccg cgacgtcaac tcatggtgcc   600
gcagggccag ggccaaggct gcctctgcag ggaagaaggc cagcagtgct gctgccccgc   660
acaccgtgag ctacccggac aatctgacct accgcgatct ctactacttc ctcttcgccc   720
ccaccttgtg ctacgagctc aactttcccc gctctccccg catccggaag cgctttctgc   780
tgcgacggat ccttgagatg ctgttcttca cccagctcca ggtggggctg atccagcagt   840
ggatggtccc caccatccag aactccatga agcccttcaa ggacatggac tactcacgca   900
tcatcgagcg cctcctgaag ctggcggtcc ccaatcacct catctggctc atcttcttct   960
actggctctt ccactcctgc ctgaatgccg tggctgagct catgcagttt ggagaccggg  1020
agttctaccg ggactggtgg aactccgagt ctgtcaccta cttctggcag aactggaaca  1080
tccctgtgca caagtggtgc atcagacact tctacaagcc catgcttcga cgggcagca   1140 gcaagtggat ggcaggaaca gggtgttcc tggcctcggc cttcttccac gagtacctgg  1200
tgagcgtccc tctgcgaatg ttccgcctct gggcgttcac gggcatgatg gctcagatcc  1260
cactggcctg gttcgtgggc cgcttttccc aggcaacta tggcaacgca gctgtgtggc  1320
tgtcgctcat catcggacag ccaatagccg tcctcatgta cgtccacgac tactacgtgc  1380
tcaactatga ggccccagcg gcagaggcct gagctgcacc tgagggcctg gcttctcact  1440
gccacctcac acccgctgcc agagcccacc tctcctccta ggcctcgagt gctggggatg  1500
ggcctggctg cacagcatcc tcctctggtc ccagggaggc ctctctgccc ctatgggct  1560 ctgtcctgca cccctcaggg atggcgacag caggccagac acagtctgat gccagctggg  1620
```

-continued

```
agtcttgctg accctgcccc gggtccgagg gtgtcaataa agtgctgtcc agtgacctct      1680
tcagcctgcc aggggcctgg ggcctggtgg ggggtatggc cacacccaca agggcgagtg      1740
ccagagctgt gtggacagct gtcccaggac ctgccgggga gcagcagctc cactgcagca      1800
gggcgggcat ggccggtagg gggagtgcaa ggccaggcag acgcccccat tccccacact      1860
cccctaccta gaaaagctca gctcaggcgt cctct                                 1895
```

<210> SEQ ID NO 33
<211> LENGTH: 1766
<212> TYPE: DNA
<213> ORGANISM: Artificial Sequence
<220> FEATURE:
<223> OTHER INFORMATION: Description of Artificial Sequence: Inferred cDNA sequence

<400> SEQUENCE: 33

```
cacgactggg ccgcgacgtg gtgcgggccg aagccatggg cgaccgcgga ggcgcgggaa       60
gctctcggcg tcggaggacc ggctcgcggg tttccatcca gggtggtagt gggcccatgg      120
tagacgaaga ggaggtgcga gacgccgctg tgggccccga cttgggcgcc gggggtgacg      180
ctccggctcc ggctccggtt ccggctccag cccacacccg gacaaagac cggcagacca       240 gcgtgggcga cggccactgg gagctgaggt gccatcgtct gcaagactct tgttcagct       300 cagacagcgg tttcagcaat taccgtggta tcctgaattg gtgcgtggtg atgctgatcc      360
tgagtaatgc aaggttattt ttagagaatc ttatcaagta tggcatcctg gtggatccca      420
tccaggtggt gtctctgttt ctgaaggacc cctacagctg gcctgcccca tgcttgatca      480
ttgcatccaa tatctttatt gtggctacat ttcagattga gaagcgcctg tcagtgggtg      540
ccctgacaga gcagatgggg ctgctgctac atgtggttaa cctggccaca attatctgct      600
tcccagcagc tgtggcctta ctggttgagt ctatcactcc agtgggttcc ctgtttgctc      660
tggcatcata ctccatcatc ttcctcaagc ttttctccta ccgggatgtc aatctgtggt      720
gccgccagcg aagggtcaag gccaaagctg tgtctgcagg gaagaaggtc agtgggctg       780 ctgcccagaa cactgtaagc tatccggaca acctgaccta ccgagatctc tattacttca      840
tctttgctcc tactttgtgt tatgaactca actttcctcg atccccccga atacgaaagc      900
gctttctgct acggcgggtt cttgagatgc tcttttcac ccagcttcaa gtggggctga      960
tccagcagtg gatggtccct actatccaga actccatgaa gcccttcaag gacatggact     1020
attcacgaat cattgagcgt ctcttaaagc tggcggtccc caaccatctg atatggctca     1080
tcttcttcta ttggcttttc cactcatgtc tcaatgctgt ggcagagctc ctgcagtttg     1140
gagaccgcga gttctacagg gactggtgga atgctgagtc tgtcacctac ttttggcaga     1200
actggaatat ccccgtgcac aagtggtgca tcagacactt ctacaagcct atgctcagac     1260
tgggcagcaa caaatggatg gccaggactg gggtcttttt ggcgtcagcc ttcttccatg     1320
agtacctagt gagcattccc ctgaggatgt tccgcctctg ggcattcaca gccatgatgg     1380
ctcaggtccc actggcctgg attgtgaacc gcttcttcca agggaactat ggcaatgcag     1440
ctgtgtgggt gacactcatc attgggcaac cggtggctgt gctcatgtat gtccacgact     1500
actacgtgct caactatgat gccccagtgg gggcctgagc tactgccaaa ggccagccct     1560
ccctaacctg ggcctggagt tctggagggc ttcctggctg cctgcacact cctcctagtc     1620
tgggaggcct ctctgcccct atggggccta ctcctgctct tggggatggc acctgagtcc     1680
agctggtatg agccagtgct gggagtctgt gctgaccagg ggctgaggat atcaataaag     1740
```

```
agctatctaa aaaaaaaaaa aaaaaa                                              1766
```

<210> SEQ ID NO 34
<211> LENGTH: 409
<212> TYPE: PRT
<213> ORGANISM: Homo sapiens

<400> SEQUENCE: 34

```
Arg Arg Ser Leu Leu Asp Glu Leu Leu Glu Val Asp His Ile Arg Thr
  1               5                  10                  15

Ile Tyr His Met Phe Ile Ala Leu Leu Ile Leu Phe Ile Leu Ser Thr
                 20                  25                  30

Leu Val Val Asp Tyr Ile Asp Glu Gly Arg Leu Val Leu Glu Phe Ser
             35                  40                  45

Leu Leu Ser Tyr Ala Phe Gly Lys Phe Pro Thr Val Trp Thr Trp
         50                  55                  60

Trp Ile Met Phe Leu Ser Thr Phe Ser Val Pro Tyr Phe Leu Phe Gln
 65                  70                  75                  80

His Trp Arg Thr Gly Tyr Ser Lys Ser Ser His Pro Leu Ile Arg Ser
                 85                  90                  95

Leu Phe His Gly Phe Leu Phe Met Ile Phe Gln Ile Gly Val Leu Gly
            100                 105                 110

Phe Gly Pro Thr Tyr Val Val Leu Ala Tyr Thr Leu Pro Pro Ala Ser
            115                 120                 125

Arg Phe Ile Ile Ile Phe Glu Gln Ile Arg Phe Val Met Lys Ala His
        130                 135                 140

Ser Phe Val Arg Glu Asn Val Pro Arg Val Leu Asn Ser Ala Lys Glu
145                 150                 155                 160

Lys Ser Ser Thr Val Pro Ile Pro Thr Val Asn Gln Tyr Leu Tyr Phe
                165                 170                 175

Leu Phe Ala Pro Thr Leu Ile Tyr Arg Asp Ser Tyr Pro Arg Asn Pro
            180                 185                 190

Thr Val Arg Trp Gly Tyr Val Ala Met Lys Phe Ala Gln Val Phe Gly
        195                 200                 205

Cys Phe Phe Tyr Val Tyr Tyr Ile Phe Glu Arg Leu Cys Ala Pro Leu
    210                 215                 220

Phe Arg Asn Ile Lys Gln Glu Pro Phe Ser Ala Arg Val Leu Val Leu
225                 230                 235                 240

Cys Val Phe Asn Ser Ile Leu Pro Gly Val Leu Ile Leu Phe Leu Thr
                245                 250                 255

Phe Phe Ala Phe Leu His Cys Trp Leu Asn Ala Phe Ala Glu Met Leu
            260                 265                 270

Arg Phe Gly Asp Arg Met Phe Tyr Lys Asp Trp Trp Asn Ser Thr Ser
        275                 280                 285

Tyr Ser Asn Tyr Tyr Arg Thr Trp Asn Val Val His Asp Trp Leu
    290                 295                 300

Tyr Tyr Tyr Ala Tyr Lys Asp Phe Leu Trp Phe Ser Lys Arg Phe
305                 310                 315                 320

Lys Ser Ala Ala Met Leu Ala Val Phe Ala Val Ser Ala Val His
                325                 330                 335

Glu Tyr Ala Leu Ala Val Cys Leu Ser Phe Phe Tyr Pro Val Leu Phe
            340                 345                 350

Val Leu Phe Met Phe Phe Gly Met Ala Phe Asn Phe Ile Val Asn Asp
        355                 360                 365
```

```
Ser Arg Lys Lys Pro Ile Trp Asn Val Leu Met Trp Thr Ser Leu Phe
    370                 375                 380
Leu Gly Asn Gly Val Leu Leu Cys Phe Tyr Ser Gln Glu Trp Tyr Ala
385                 390                 395                 400
Arg Arg His Cys Pro Leu Lys Asn Pro
                405

<210> SEQ ID NO 35
<211> LENGTH: 409
<212> TYPE: PRT
<213> ORGANISM: Mus musculus

<400> SEQUENCE: 35

Arg Gln Ser Leu Leu Asp Glu Leu Phe Glu Val Asp His Ile Arg Thr
1               5                   10                  15
Ile Tyr His Met Phe Ile Ala Leu Leu Ile Leu Phe Val Leu Ser Thr
                20                  25                  30
Ile Val Val Asp Tyr Ile Asp Glu Gly Arg Leu Val Leu Glu Phe Asn
            35                  40                  45
Leu Leu Ala Tyr Ala Phe Gly Lys Phe Pro Thr Val Ile Trp Thr Trp
    50                  55                  60
Trp Ala Met Phe Leu Ser Thr Leu Ser Ile Pro Tyr Phe Leu Phe Gln
65                  70                  75                  80
Pro Trp Ala His Gly Tyr Ser Lys Ser Ser His Pro Leu Ile Tyr Ser
                85                  90                  95
Leu Val His Gly Leu Leu Phe Leu Val Phe Gln Leu Gly Val Leu Gly
                100                 105                 110
Phe Val Pro Thr Tyr Val Val Leu Ala Tyr Thr Leu Pro Pro Ala Ser
            115                 120                 125
Arg Phe Ile Leu Ile Leu Glu Gln Ile Arg Leu Ile Met Lys Ala His
    130                 135                 140
Ser Phe Val Arg Glu Asn Ile Pro Arg Val Leu Asn Ala Ala Lys Glu
145                 150                 155                 160
Lys Ser Ser Lys Asp Pro Leu Pro Thr Val Asn Gln Tyr Leu Tyr Phe
                165                 170                 175
Leu Phe Ala Pro Thr Leu Ile Tyr Arg Asp Asn Tyr Pro Arg Thr Pro
                180                 185                 190
Thr Val Arg Trp Gly Tyr Val Ala Met Gln Phe Leu Gln Val Phe Gly
            195                 200                 205
Cys Leu Phe Tyr Val Tyr Tyr Ile Phe Glu Arg Leu Cys Ala Pro Leu
    210                 215                 220
Phe Arg Asn Ile Lys Gln Glu Pro Phe Ser Ala Arg Val Leu Val Leu
225                 230                 235                 240
Cys Val Phe Asn Ser Ile Leu Pro Gly Val Leu Ile Leu Phe Leu Ser
                245                 250                 255
Phe Phe Ala Phe Leu His Cys Trp Leu Asn Ala Phe Ala Glu Met Leu
                260                 265                 270
Arg Phe Gly Asp Arg Met Phe Tyr Lys Asp Trp Trp Asn Ser Thr Ser
            275                 280                 285
Tyr Ser Asn Tyr Tyr Arg Thr Trp Asn Val Val His Asp Trp Leu
    290                 295                 300
Tyr Tyr Tyr Val Tyr Lys Asp Leu Leu Trp Phe Ser Lys Arg Phe
305                 310                 315                 320
Lys Ser Ala Ala Met Leu Ala Val Phe Ala Leu Ser Ala Val Val His
```

```
                    325                 330                 335
Glu Tyr Ala Leu Ala Ile Cys Leu Ser Tyr Phe Tyr Pro Val Leu Phe
                340                 345                 350

Val Leu Phe Met Phe Phe Gly Met Ala Phe Asn Phe Ile Val Asn Asp
            355                 360                 365

Ser Arg Lys Arg Pro Ile Trp Asn Ile Met Val Trp Ala Ser Leu Phe
370                 375                 380

Leu Gly Tyr Gly Leu Ile Leu Cys Phe Tyr Ser Gln Glu Trp Tyr Ala
385                 390                 395                 400

Arg Gln His Cys Pro Leu Lys Asn Pro
                405

<210> SEQ ID NO 36
<211> LENGTH: 429
<212> TYPE: PRT
<213> ORGANISM: Saccharomyces cerevisiae

<400> SEQUENCE: 36

Asp Lys Ala Asp Ala Pro Pro Gly Glu Lys Leu Glu Ser Asn Phe Ser
1               5                   10                  15

Gly Ile Tyr Val Phe Ala Trp Met Phe Leu Gly Trp Ile Ala Ile Arg
                20                  25                  30

Cys Cys Thr Asp Tyr Tyr Ala Ser Tyr Gly Ser Ala Trp Asn Lys Leu
            35                  40                  45

Glu Ile Val Gln Tyr Met Thr Thr Asp Leu Phe Thr Ile Ala Met Leu
        50                  55                  60

Asp Leu Ala Met Phe Leu Cys Thr Phe Phe Val Val Phe Val His Trp
65                  70                  75                  80

Leu Val Lys Lys Arg Ile Ile Asn Trp Lys Trp Thr Gly Phe Val Ala
                85                  90                  95

Val Ser Ile Phe Glu Leu Ala Phe Ile Pro Val Thr Phe Pro Ile Tyr
            100                 105                 110

Val Tyr Tyr Phe Asp Phe Asn Trp Val Thr Arg Ile Phe Leu Phe Leu
        115                 120                 125

His Ser Val Val Phe Val Met Lys Ser His Ser Phe Ala Phe Tyr Asn
130                 135                 140

Gly Tyr Leu Trp Asp Ile Lys Gln Glu Leu Glu Tyr Ser Ser Lys Gln
145                 150                 155                 160

Leu Gln Lys Tyr Lys Glu Ser Leu Ser Pro Glu Thr Arg Glu Ile Leu
                165                 170                 175

Gln Lys Ser Cys Asp Phe Cys Leu Phe Glu Leu Asn Tyr Gln Thr Lys
            180                 185                 190

Asp Asn Asp Phe Pro Asn Asn Ile Ser Cys Ser Asn Phe Met Phe
        195                 200                 205

Cys Leu Phe Pro Val Leu Val Tyr Gln Ile Asn Tyr Pro Arg Thr Ser
210                 215                 220

Arg Ile Arg Trp Arg Tyr Val Leu Glu Lys Val Cys Ala Ile Ile Gly
225                 230                 235                 240

Thr Ile Phe Leu Met Met Val Thr Ala Gln Phe Phe Met His Pro Val
                245                 250                 255

Ala Met Arg Cys Ile Gln Phe His Asn Thr Pro Thr Phe Gly Gly Trp
            260                 265                 270

Ile Pro Ala Thr Gln Glu Trp Phe His Leu Leu Phe Asp Met Ile Pro
        275                 280                 285
```

```
Gly Phe Thr Val Leu Tyr Met Leu Thr Phe Tyr Met Ile Trp Asp Ala
        290                 295                 300

Leu Leu Asn Cys Val Ala Glu Leu Thr Arg Phe Ala Asp Arg Tyr Phe
305                 310                 315                 320

Tyr Gly Asp Trp Trp Asn Cys Val Ser Phe Glu Glu Phe Ser Arg Ile
                325                 330                 335

Trp Asn Val Pro Val His Lys Phe Leu Leu Arg His Val Tyr His Ser
                340                 345                 350

Ser Met Gly Ala Leu His Leu Ser Lys Ser Gln Ala Thr Leu Phe Thr
        355                 360                 365

Phe Phe Leu Ser Ala Val Phe His Glu Met Ala Met Phe Ala Ile Phe
370                 375                 380

Arg Arg Val Arg Gly Tyr Leu Phe Met Phe Gln Leu Ser Gln Phe Val
385                 390                 395                 400

Trp Thr Ala Leu Ser Asn Thr Lys Phe Leu Arg Ala Arg Pro Gln Leu
                405                 410                 415

Ser Asn Val Val Phe Ser Phe Gly Val Cys Ser Gly Pro
                420                 425
```

<210> SEQ ID NO 37
<211> LENGTH: 432
<212> TYPE: PRT
<213> ORGANISM: Saccharomyces cerevisiae

<400> SEQUENCE: 37

```
Glu Thr Val Val Thr Val Glu Thr Thr Ile Ile Ser Ser Asn Phe Ser
1               5                   10                  15

Gly Leu Tyr Val Ala Phe Trp Met Ala Ile Ala Phe Gly Ala Val Lys
            20                  25                  30

Ala Leu Ile Asp Tyr Tyr Gln His Asn Gly Ser Phe Lys Asp Ser
        35                  40                  45

Glu Ile Leu Lys Phe Met Thr Thr Asn Leu Phe Thr Val Ala Ser Val
    50                  55                  60

Asp Leu Leu Met Tyr Leu Ser Thr Tyr Phe Val Val Gly Ile Gln Tyr
65                  70                  75                  80

Leu Cys Lys Trp Gly Val Leu Lys Trp Gly Thr Thr Gly Trp Ile Phe
                85                  90                  95

Thr Ser Ile Tyr Glu Phe Leu Phe Val Ile Phe Tyr Met Tyr Leu Thr
            100                 105                 110

Glu Asn Ile Leu Lys Leu His Trp Leu Ser Lys Ile Phe Leu Phe Leu
        115                 120                 125

His Ser Leu Val Leu Leu Met Lys Met His Ser Phe Ala Phe Tyr Asn
130                 135                 140

Gly Tyr Leu Trp Gly Ile Lys Glu Glu Leu Gln Phe Ser Lys Ser Ala
145                 150                 155                 160

Leu Ala Lys Tyr Lys Asp Ser Ile Asn Asp Pro Lys Val Ile Gly Ala
                165                 170                 175

Leu Glu Lys Ser Cys Glu Phe Cys Ser Phe Glu Leu Ser Ser Gln Ser
            180                 185                 190

Leu Ser Asp Gln Thr Gln Lys Phe Pro Asn Asn Ile Ser Ala Lys Ser
        195                 200                 205

Phe Phe Trp Phe Thr Met Phe Pro Thr Leu Ile Tyr Gln Ile Glu Tyr
    210                 215                 220

Pro Arg Thr Lys Glu Ile Arg Trp Ser Tyr Val Leu Glu Lys Ile Cys
225                 230                 235                 240
```

```
Ala Ile Phe Gly Thr Ile Phe Leu Met Met Ile Asp Ala Gln Ile Leu
                245                 250                 255
Met Tyr Pro Val Ala Met Arg Ala Leu Ala Val Arg Asn Ser Glu Trp
                260                 265                 270
Thr Gly Ile Leu Asp Arg Leu Leu Lys Trp Val Gly Leu Leu Val Asp
                275                 280                 285
Ile Val Pro Gly Phe Ile Val Met Tyr Ile Leu Asp Phe Tyr Leu Ile
                290                 295                 300
Trp Asp Ala Ile Leu Asn Cys Val Ala Glu Leu Thr Arg Phe Gly Asp
305                 310                 315                 320
Arg Tyr Phe Tyr Gly Asp Trp Trp Asn Cys Val Ser Trp Ala Asp Phe
                325                 330                 335
Ser Arg Ile Trp Asn Ile Pro Val His Lys Phe Leu Leu Arg His Val
                340                 345                 350
Tyr His Ser Ser Met Ser Ser Phe Lys Leu Asn Lys Ser Gln Ala Thr
                355                 360                 365
Leu Met Thr Phe Phe Leu Ser Ser Val Val His Glu Leu Ala Met Tyr
                370                 375                 380
Val Ile Phe Lys Lys Leu Arg Phe Tyr Leu Phe Phe Gln Met Leu
385                 390                 395                 400
Gln Met Pro Leu Val Ala Leu Thr Asn Thr Lys Phe Met Arg Asn Arg
                405                 410                 415
Thr Ile Ile Gly Asn Val Ile Phe Trp Leu Gly Ile Cys Met Gly Pro
                420                 425                 430

<210> SEQ ID NO 38
<211> LENGTH: 1942
<212> TYPE: DNA
<213> ORGANISM: Arabidopsis thaliana

<400> SEQUENCE: 38
ctctcgtgaa tccttttcc tttcttcttc ttcttctctt cagagaaaac tttgcttctc      60
tttctataag gaaccagaca cgaatcccat tcccaccgat ttcttagctt cttccttcaa     120
tccgctcttt ccctctccat tagattctgt ttcctctttc aatttcttct gcatgcttct     180
cgattctctc tgacgcctct tttctcccga cgctgtttcg tcaaacgctt ttcgaaatgg     240
cgattttgga ttctgctggc gttactacgg tgacggagaa cggtggcgga gagttcgtcg     300
atcttgatag gcttcgtcga cggaaatcga gatcggattc ttctaacgga cttcttctct     360
ctggttccga taataattct ccttcggatg atgttggagc tcccgccgac gttagggatc     420
ggattgattc cgttgttaac gatgacgctc agggaacagc caatttggcc ggagataata     480
acggtggtgg cgataataac ggtggtggaa gaggcggcgg agaaggaaga ggaaacgccg     540
atgctacgtt tacgtatcga ccgtcggttc cagctcatcg gagggcgaga gagagtccac     600
ttagctccga cgcaatcttc aaacagagcc atgccggatt attcaacctc tgtgtagtag     660
ttcttattgc tgtaaacagt agactcatca tcgaaaatct tatgaagtat ggttggttga     720
tcagaacgga tttctggttt agttcaagat cgctgcgaga ttggccgctt ttcatgtgtt     780
gtatatccct ttcgatcttt cctttggctg cctttacggt tgagaaattg gtacttcaga     840
aatacatatc agaacctgtt gtcatctttc ttcatattat tatcaccatg acagaggttt     900
tgtatccagt ttacgtcacc ctaaggtgtg attctgcttt tttatcaggt gtcactttga     960
tgctcctcac ttgcattgtg tggctaaagt tggtttctta tgctcatact agctatgaca    1020
```

```
taagatccct agccaatgca gctgataagg ccaatcctga agtctcctac tacgttagct    1080
tgaagagctt ggcatatttc atggtcgctc ccacattgtg ttatcagcca agttatccac    1140
gttctgcatg tatacggaag ggttgggtgg ctcgtcaatt tgcaaaactg gtcatattca    1200
ccggattcat gggatttata atagaacaat atataaatcc tattgtcagg aactcaaagc    1260
atcctttgaa aggcgatctt ctatatgcta ttgaaagagt gttgaagctt tcagttccaa    1320
atttatatgt gtggctctgc atgttctact gcttcttcca cctttggtta aacatattgg    1380
cagagcttct ctgcttcggg gatcgtgaat tctacaaaga ttggtggaat gcaaaaagtg    1440
tgggagatta ctggagaatg tggaatatgc ctgttcataa atggatggtt cgacatatat    1500
acttcccgtg cttgcgcagc aagataccaa agacactcgc cattatcatt gctttcctag    1560
tctctgcagt ctttcatgag ctatgcatcg cagttccttg tcgtctcttc aagctatggg    1620
cttttcttgg gattatgttt caggtgcctt tggtcttcat cacaaactat ctacaggaaa    1680
ggtttggctc aacggtgggg aacatgatct tctggttcat cttctgcatt ttcggacaac    1740
cgatgtgtgt gcttctttat taccacgacc tgatgaaccg aaaaggatcg atgtcatgaa    1800
acaactgttc aaaaaatgac tttcttcaaa catctatggc ctcgttggat ctccgttgat    1860
gttgtggtgg ttctgatgct aaaacgacaa atagtgttat aaccattgaa gaagaaaaga    1920
caattagagt tgttgtatcg ca                                             1942
```

```
<210> SEQ ID NO 39
<211> LENGTH: 520
<212> TYPE: PRT
<213> ORGANISM: Arabidopsis thaliana

<400> SEQUENCE: 39

Met Ala Ile Leu Asp Ser Ala Gly Val Thr Val Thr Glu Asn Gly
  1               5                  10                  15

Gly Gly Glu Phe Val Asp Leu Asp Arg Leu Arg Arg Lys Ser Arg
                 20                  25                  30

Ser Asp Ser Ser Asn Gly Leu Leu Leu Ser Gly Ser Asp Asn Asn Ser
         35                  40                  45

Pro Ser Asp Asp Val Gly Ala Pro Asp Val Arg Asp Arg Ile Asp
     50                  55                  60

Ser Val Val Asn Asp Asp Ala Gln Gly Thr Ala Asn Leu Ala Gly Asp
 65                  70                  75                  80

Asn Asn Gly Gly Gly Asp Asn Asn Gly Gly Gly Arg Gly Gly Gly Glu
                 85                  90                  95

Gly Arg Gly Asn Ala Asp Ala Thr Phe Thr Tyr Arg Pro Ser Val Pro
                100                 105                 110

Ala His Arg Arg Ala Arg Glu Ser Pro Leu Ser Ser Asp Ala Ile Phe
            115                 120                 125

Lys Gln Ser His Ala Gly Leu Phe Asn Leu Cys Val Val Leu Ile
        130                 135                 140

Ala Val Asn Ser Arg Leu Ile Ile Glu Asn Leu Met Lys Tyr Gly Trp
145                 150                 155                 160

Leu Ile Arg Thr Asp Phe Trp Phe Ser Ser Arg Ser Leu Arg Asp Trp
                165                 170                 175

Pro Leu Phe Met Cys Cys Ile Ser Leu Ser Ile Phe Pro Leu Ala Ala
            180                 185                 190

Phe Thr Val Glu Lys Leu Val Leu Gln Lys Tyr Ile Ser Glu Pro Val
        195                 200                 205
```

-continued

```
Val Ile Phe Leu His Ile Ile Thr Met Thr Glu Val Leu Tyr Pro
    210             215             220
Val Tyr Val Thr Leu Arg Cys Asp Ser Ala Phe Leu Ser Gly Val Thr
225             230             235             240
Leu Met Leu Thr Cys Ile Val Trp Leu Lys Leu Val Ser Tyr Ala
            245             250             255
His Thr Ser Tyr Asp Ile Arg Ser Leu Ala Asn Ala Ala Asp Lys Ala
        260             265             270
Asn Pro Glu Val Ser Tyr Tyr Val Ser Leu Lys Ser Leu Ala Tyr Phe
    275             280             285
Met Val Ala Pro Thr Leu Cys Tyr Gln Pro Ser Tyr Pro Arg Ser Ala
290             295             300
Cys Ile Arg Lys Gly Trp Val Ala Arg Gln Phe Ala Lys Leu Val Ile
305             310             315             320
Phe Thr Gly Phe Met Gly Phe Ile Ile Glu Gln Tyr Ile Asn Pro Ile
            325             330             335
Val Arg Asn Ser Lys His Pro Leu Lys Gly Asp Leu Leu Tyr Ala Ile
            340             345             350
Glu Arg Val Leu Lys Leu Ser Val Pro Asn Leu Tyr Val Trp Leu Cys
        355             360             365
Met Phe Tyr Cys Phe Phe His Leu Trp Leu Asn Ile Leu Ala Glu Leu
    370             375             380
Leu Cys Phe Gly Asp Arg Glu Phe Tyr Lys Asp Trp Trp Asn Ala Lys
385             390             395             400
Ser Val Gly Asp Tyr Trp Arg Met Trp Asn Met Pro Val His Lys Trp
            405             410             415
Met Val Arg His Ile Tyr Phe Pro Cys Leu Arg Ser Lys Ile Pro Lys
            420             425             430
Thr Leu Ala Ile Ile Ile Ala Phe Leu Val Ser Ala Val Phe His Glu
        435             440             445
Leu Cys Ile Ala Val Pro Cys Arg Leu Phe Lys Leu Trp Ala Phe Leu
    450             455             460
Gly Ile Met Phe Gln Val Pro Leu Val Phe Ile Thr Asn Tyr Leu Gln
465             470             475             480
Glu Arg Phe Gly Ser Thr Val Gly Asn Met Ile Phe Trp Phe Ile Phe
            485             490             495
Cys Ile Phe Gly Gln Pro Met Cys Val Leu Leu Tyr Tyr His Asp Leu
        500             505             510
Met Asn Arg Lys Gly Ser Met Ser
    515             520
```

<210> SEQ ID NO 40
<211> LENGTH: 29
<212> TYPE: DNA
<213> ORGANISM: Artificial Sequence
<220> FEATURE:
<223> OTHER INFORMATION: Description of Artificial Sequence: Synthetic oligonucleotide primer

<400> SEQUENCE: 40
tgcaaattga cgagcacacc aaccccttc                                    29

<210> SEQ ID NO 41
<211> LENGTH: 28
<212> TYPE: DNA
<213> ORGANISM: Artificial Sequence
<220> FEATURE:

<223> OTHER INFORMATION: Description of Artificial Sequence: Synthetic
      oligonuclotide primer

<400> SEQUENCE: 41
aaggatgctt tgagttcctg acaatagg                                            28

<210> SEQ ID NO 42
<211> LENGTH: 1942
<212> TYPE: DNA
<213> ORGANISM: Arabidopsis thaliana

<400> SEQUENCE: 42

| | | | | | |
|---|---|---|---|---|---|
| ctctcgtgaa | tccttttcc | tttcttcttc | ttcttctctt | cagagaaaac | tttgcttctc | 60 |
| tttctataag | gaaccagaca | cgaatcccat | tcccaccgat | ttcttagctt | cttccttcaa | 120 |
| tccgctcttt | ccctctccat | tagattctgt | ttcctctttc | aatttcttct | gcatgcttct | 180 |
| cgattctctc | tgacgcctct | tttctcccga | cgctgtttcg | tcaaacgctt | ttcgaaatgg | 240 |
| cgattttgga | ttctgctggc | gttactacgg | tgacggagaa | cggtggcgga | gagttcgtcg | 300 |
| atcttgatag | gcttcgtcga | cggaaatcga | gatcggattc | ttctaacgga | cttcttctct | 360 |
| ctggttccga | taataattct | ccttcggatg | atgttggagc | tcccgccgac | gttagggatc | 420 |
| ggattgattc | cgttgttaac | gatgacgctc | agggaacagc | caatttggcc | ggagataata | 480 |
| acggtggtgg | cgataataac | ggtggtggaa | gaggcggcgg | agaaggaaga | ggaaacgccg | 540 |
| atgctacgtt | tacgtatcga | ccgtcggttc | cagctcatcg | gagggcgaga | gagagtccac | 600 |
| ttagctccga | cgcaatcttc | aaacagagcc | atgccggatt | attcaacctc | tgtgtagtag | 660 |
| ttcttattgc | tgtaaacagt | agactcatca | tcgaaaatct | tatgaagtat | ggttggttga | 720 |
| tcagaacgga | tttctggttt | agttcaagat | cgctgcgaga | ttggccgctt | ttcatgtgtt | 780 |
| gtatatccct | ttcgatcttt | cctttggctg | cctttacggt | tgagaaattg | gtacttcaga | 840 |
| aatacatatc | agaacctgtt | gtcatctttc | ttcatattat | tatcaccatg | acagaggttt | 900 |
| tgtatccagt | ttacgtcacc | ctaaggtgtg | attctgcttt | tttatcaggt | gtcactttga | 960 |
| tgctcctcac | ttgcattgtg | tggctaaagt | tggtttctta | tgctcatact | agctatgaca | 1020 |
| taagatccct | agccaatgca | gctgataagg | ccaatcctga | agtctcctac | tacgttagct | 1080 |
| tgaagagctt | ggcatatttc | atggtcgctc | ccacattgtg | ttatcagcca | agttatccac | 1140 |
| gttctgcatg | tatacggaag | ggttgggtgg | ctcgtcaatt | tgcaaaactg | gtcatattca | 1200 |
| ccggattcat | gggatttata | atagaacaat | atataaatcc | tattgtcagg | aactcaaagc | 1260 |
| atcctttgaa | aggcgatctt | ctatatgcta | ttgaaagagt | gttgaagctt | tcagttccaa | 1320 |
| atttatatgt | gtggctctgc | atgttctact | gcttcttcca | cctttggtta | aacatattgg | 1380 |
| cagagcttct | ctgcttcggg | gatcgtgaat | tctacaaaga | ttggtggaat | gcaaaaagtg | 1440 |
| tgggagatta | ctggagaatg | tggaatatgc | ctgttcataa | atggatggtt | cgacatatat | 1500 |
| acttcccgtg | cttgcgcagc | aagataccaa | agacactcgc | cattatcatt | gctttcctag | 1560 |
| tctctgcagt | cttcatgag | ctatgcatcg | cagttccttg | tcgtctcttc | aagctatggg | 1620 |
| cttttcttgg | gattatgttt | caggtgcctt | tggtcttcat | cacaaactat | ctacaggaaa | 1680 |
| ggtttggctc | aacggtgggg | aacatgatct | tctggttcat | cttctgcatt | ttcggacaac | 1740 |
| cgatgtgtgt | gcttctttat | taccacgacc | tgatgaaccg | aaaaggatcg | atgtcatgaa | 1800 |
| acaactgttc | aaaaaatgac | tttcttcaaa | catctatggc | ctcgttggat | ctccgttgat | 1860 |
| gttgtggtgg | ttctgatgct | aaaacgacaa | atagtgttat | aaccattgaa | gaagaaaga | 1920 |

```
caattagagt tgttgtatcg ca                                              1942
```

<210> SEQ ID NO 43
<211> LENGTH: 234
<212> TYPE: DNA
<213> ORGANISM: Glycine max
<220> FEATURE:
<221> NAME/KEY: unsure
<222> LOCATION: (1)..(234)
<223> OTHER INFORMATION: n=unknown

<400> SEQUENCE: 43

```
gtaagcttca agagcttagc atanttcctg gttgcccta ncattatgtt accagccaan      60
ctatcctcgc acaccttata ttcgaaaggg ttggctgttt cgccaacttg tcaactgata    120
atatttacag gagttatggg atttataata gaacaataca ttaatcccat tgtacaaaat    180
tcacagcatc ctctcaaggg aaaccttctt tacgccatcg agagagttct gaag          234
```

<210> SEQ ID NO 44
<211> LENGTH: 267
<212> TYPE: DNA
<213> ORGANISM: Glycine max

<400> SEQUENCE: 44

```
ctgcttttgt atctggtgtc acgttgatgc tattaacttg cattgtgtgg ttaaaattgg     60
tgtcatatgc acatacaaac tatgatatga gagcacttac tgtttcgaat gaaaagggag   120
aaacattacc caatactttg atatggagta ccgtacact gtgaccttca ggagtttggc    180
atacttcatg gttgctccta cattatgcta tcagacaagc tatcctcgca caccttcagt   240
tcgaaagggt tgggtgtttc gtcaact                                        267
```

<210> SEQ ID NO 45
<211> LENGTH: 275
<212> TYPE: DNA
<213> ORGANISM: Glycine max
<220> FEATURE:
<221> NAME/KEY: unsure
<222> LOCATION: (1)..(275)
<223> OTHER INFORMATION: n=unknown

<400> SEQUENCE: 45

```
gtggaatgcc aaaactgttg aagattattg gaggatgtgg aatatgcctg ttcacaaatg     60
gatgatccgc cacctatatt ttccatgttt aaggcacggt ataccaaagg ccgttgctct   120
tttaattgcc ttcctggttc tgctttattc catgagctgt gcatcgctgt tccttgccca   180
catattcaag tngtgggttt cngnggaatt nagtttcagg tnccttgggt ttcnaccnna   240
attnntnggc naaaaaattc cnngaacccc ggggg                               275
```

<210> SEQ ID NO 46
<211> LENGTH: 257
<212> TYPE: DNA
<213> ORGANISM: Glycine max

<400> SEQUENCE: 46

```
aacggaattg agactccaga gaatatgcca aaatgtatta ataattgtca caacttggaa     60
ggcttttgga aaaactggca tgcttccttc aacaagtggc ttgtgaggta tatatacatt   120
cctcttgggg gatctaagaa aaagctacta aatgtgtggg ttgttttcac atttgttgca   180
atctggcatg atttagagtg gaagcttctt tcatgggcat ggttgacgtg tttattcttc   240
atccctgagt tggtttt                                                   257
```

<210> SEQ ID NO 47
<211> LENGTH: 253
<212> TYPE: DNA
<213> ORGANISM: Zea mays

<400> SEQUENCE: 47

| | | | | | |
|---|---|---|---|---|---|
| agaaaatgga | acatgcctgt | gcataaatgg | attgttcgtc | atatatattt | tccttgcatg | 60 |
| cgaaatggta | tatcaaagga | agttgctgtt | tttatatcgt | tcttgtttct | gctgtacttc | 120 |
| atgagttatg | tgttgctgtt | ccctgccaca | tactcaagtt | ctgggctttt | tttaggaatc | 180 |
| atgcttcaga | ttcccctcat | catattgaca | tcatacctca | aaaataaatt | cagtgacaca | 240 |
| atggttggca | ata | | | | | 253 |

<210> SEQ ID NO 48
<211> LENGTH: 254
<212> TYPE: DNA
<213> ORGANISM: Zea mays

<400> SEQUENCE: 48

| | | | | | |
|---|---|---|---|---|---|
| tgaagtatgg | cttattaata | agatctggct | tttggtttaa | tgctacatca | ttgcgagact | 60 |
| ggccactgct | aatgtgttgc | cttagtctac | ccatatttcc | ccttggtgca | tttgcagtcg | 120 |
| aaaagttggc | attcaacaat | ctcattagtg | atcctgctac | tacctgtttt | cacatccttt | 180 |
| ttacaacatt | tgaaattgta | tatccagtgc | tcgtgattct | taagtgtgat | tctgcagttt | 240 |
| tatcaggctt | tgtg | | | | | 254 |

<210> SEQ ID NO 49
<211> LENGTH: 262
<212> TYPE: DNA
<213> ORGANISM: Zea mays

<400> SEQUENCE: 49

| | | | | | |
|---|---|---|---|---|---|
| gaagtatggc | ttattaataa | gatctggctt | ttggtttaat | gctacatcat | tgcgagactg | 60 |
| gccactgcta | atgtgttgcc | ttagtctacc | catatttccc | cttggtgcat | ttgcagtcga | 120 |
| aaagttggca | ttcaacaatc | tcattagtga | tcctgctact | acctgttttc | acatcctttt | 180 |
| tacaacattt | gaaattgtat | atccagtgct | cgtgattctt | aagtgtgatt | ctgcagtttt | 240 |
| acaggctttg | tgttgatgtt | ta | | | | 262 |

<210> SEQ ID NO 50
<211> LENGTH: 325
<212> TYPE: DNA
<213> ORGANISM: Zea mays
<220> FEATURE:
<221> NAME/KEY: unsure
<222> LOCATION: (1)..(325)
<223> OTHER INFORMATION: n=unknown

<400> SEQUENCE: 50

| | | | | | |
|---|---|---|---|---|---|
| taatcnaacc | tcgntncngg | ttcagctgta | tnccatgaga | tatgtaatgc | ggtgccgtgc | 60 |
| cacatantca | natctnggca | tnncngggat | catngttcag | ataccgntgg | nattcttgac | 120 |
| aagatatctc | catgctacgt | tcaagcatgt | aatggtgggc | aacatgatan | tttggntctn | 180 |
| cagtatagtc | ggacagccga | tgtnnnnnna | tctatactac | catgacgtca | tgaacaggca | 240 |
| ggcccaggca | agtagatagt | ncggcagaga | catgtacttc | aacatcganc | atcagnagca | 300 |
| nacngagcga | gcggcangaa | ncagc | | | | 325 |

<210> SEQ ID NO 51
<211> LENGTH: 519
<212> TYPE: DNA
<213> ORGANISM: Mortierrella alpina
<220> FEATURE:
<221> NAME/KEY: unsure
<222> LOCATION: (1)..(519)
<223> OTHER INFORMATION: n=unknown

<400> SEQUENCE: 51

```
gagnnnngna acgtttagcc tnccgtagcc gccaaaatcc aagggncnac cnaccctncg      60
ttanactnaa ttngaaaatn cnnncccaac ttnaggnact tnnagncccc ccnacttgac     120
aacggagcac tatatttacc ccgtggtngt tcaacccagc catctcaccc ttgcgagcat     180
tggtgctgct cttgataccc ttcatgctta actatctcat gatcttttac atcattttcg     240
agtgcatctg caacgccttt gcggaactaa gttgctttgc ggatcgcaac ttttacgagg     300
attggtggaa ctgcgtcagc tttgatgagt gggcacgcaa atggaacaag cctgtgcaac     360
acttcttgct ccgccacgtg tacgactcga gcatccgagt ccttccactt gtccgaaatc     420
caatgccgcn aattgcaaac gttccttccc ggtcgtcaat gcgttcaacg aacctgggtg     480
aagaatgggt ggtgacaacg ttaaagtgcg cccggtatc                            519
```

<210> SEQ ID NO 52
<211> LENGTH: 45
<212> TYPE: DNA
<213> ORGANISM: Artificial Sequence
<220> FEATURE:
<223> OTHER INFORMATION: Description of Artificial Sequence: Oligonucleotide primer

<400> SEQUENCE: 52

```
ggatccgcgg ccgcacaatg aaaaaaatat cttcacatta ttcgg                      45
```

<210> SEQ ID NO 53
<211> LENGTH: 40
<212> TYPE: DNA
<213> ORGANISM: Artificial Sequence
<220> FEATURE:
<223> OTHER INFORMATION: Description of Artificial Sequence: Oligonucleotide primer

<400> SEQUENCE: 53

```
ggatcccctg caggtcattc attgacggca ttaacattgg                            40
```

<210> SEQ ID NO 54
<211> LENGTH: 44
<212> TYPE: DNA
<213> ORGANISM: Artificial Sequence
<220> FEATURE:
<223> OTHER INFORMATION: Description of Artificial Sequence: Synthetic oligonucleotide primer

<400> SEQUENCE: 54

```
ggatccgcgg ccgcacaatg ggagcgaatt cgaaatcagt aacg                       44
```

<210> SEQ ID NO 55
<211> LENGTH: 40
<212> TYPE: DNA
<213> ORGANISM: Artificial Sequence
<220> FEATURE:
<223> OTHER INFORMATION: Description of Artificial Sequence: Synthetic oligonucleotide primer

<400> SEQUENCE: 55

```
ggatccctg caggttaata cccactttta tcaagctccc                                    40

<210> SEQ ID NO 56
<211> LENGTH: 41
<212> TYPE: DNA
<213> ORGANISM: Artificial Sequence
<220> FEATURE:
<223> OTHER INFORMATION: Description of Artificial Sequence: Synthetic
      oligonucleotide primer

<400> SEQUENCE: 56
ggatccgcgg ccgcacaatg tctctattac tggaagagat c                                 41

<210> SEQ ID NO 57
<211> LENGTH: 41
<212> TYPE: DNA
<213> ORGANISM: Artificial Sequence
<220> FEATURE:
<223> OTHER INFORMATION: Description of Artificial Sequence: Synthetic
      oligonucleotide primer

<400> SEQUENCE: 57 ggatccctg caggttatgc atcaacagag acacttacag c                                  41

<210> SEQ ID NO 58
<211> LENGTH: 41
<212> TYPE: DNA
<213> ORGANISM: Artificial Sequence
<220> FEATURE:
<223> OTHER INFORMATION: Description of Artificial Sequence: Synthetic
      oligonucleotide primer

<400> SEQUENCE: 58
ggatccgcgg ccgcacaatg ggctggattc cgtgtccgtg c                                 41

<210> SEQ ID NO 59
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide primer

<400> SEQUENCE: 59 ggatccctg caggttaacc agaatcaact actttgtg                                      38

<210> SEQ ID NO 60
<211> LENGTH: 39
<212> TYPE: DNA
<213> ORGANISM: Artificial Sequence
<220> FEATURE:
<223> OTHER INFORMATION: Description of Artificial Sequence:
      Oligonucleotide primer

<400> SEQUENCE: 60
tcgacctgca ggaagcttag aaatggcgat tttggattc                                    39

<210> SEQ ID NO 61
<211> LENGTH: 36
<212> TYPE: DNA
<213> ORGANISM: Artificial Sequence
<220> FEATURE:
<223> OTHER INFORMATION: Description of Artificial Sequence:
      Oligonucleotide primer

<400> SEQUENCE: 61
```

```
ggatccgcgg ccgctcatga catcgatcct tttcgg                              36
```

<210> SEQ ID NO 62
<211> LENGTH: 56
<212> TYPE: DNA
<213> ORGANISM: Artificial Sequence
<220> FEATURE:
<223> OTHER INFORMATION: Description of Artificial Sequence: Annealed
      oligonucleotide adapter

<400> SEQUENCE: 62

```
cgcgatttaa atggcgcgcc ctgcaggcgg ccgcctgcag ggcgcgccat ttaaat        56
```

<210> SEQ ID NO 63
<211> LENGTH: 32
<212> TYPE: DNA
<213> ORGANISM: Artificial Sequence
<220> FEATURE:
<223> OTHER INFORMATION: Description of Artificial Sequence: Ligating
      oligonucleotide

<400> SEQUENCE: 63

```
tcgaggatcc gcggccgcaa gcttcctgca gg                                  32
```

<210> SEQ ID NO 64
<211> LENGTH: 32
<212> TYPE: DNA
<213> ORGANISM: Artificial Sequence
<220> FEATURE:
<223> OTHER INFORMATION: Description of Artificial Sequence: Ligating
      oligonucleotide

<400> SEQUENCE: 64

```
tcgacctgca ggaagcttgc ggccgcggat cc                                  32
```

<210> SEQ ID NO 65
<211> LENGTH: 32
<212> TYPE: DNA
<213> ORGANISM: Artificial Sequence
<220> FEATURE:
<223> OTHER INFORMATION: Description of Artificial Sequence: Ligating
      oligonucleotide

<400> SEQUENCE: 65

```
tcgacctgca ggaagcttgc ggccgcggat cc                                  32
```

<210> SEQ ID NO 66
<211> LENGTH: 32
<212> TYPE: DNA
<213> ORGANISM: Artificial Sequence
<220> FEATURE:
<223> OTHER INFORMATION: Description of Artificial Sequence: Ligating
      oligonucleotide

<400> SEQUENCE: 66

```
tcgaggatcc gcggccgcaa gcttcctgca gg                                  32
```

<210> SEQ ID NO 67
<211> LENGTH: 36
<212> TYPE: DNA
<213> ORGANISM: Artificial Sequence
<220> FEATURE:
<223> OTHER INFORMATION: Description of Artificial Sequence: Ligating
      oligonucleotide

<400> SEQUENCE: 67

```
tcgaggatcc gcggccgcaa gcttcctgca ggagct                              36
```

<210> SEQ ID NO 68
<211> LENGTH: 28
<212> TYPE: DNA
<213> ORGANISM: Artificial Sequence
<220> FEATURE:
<223> OTHER INFORMATION: Description of Artificial Sequence: Ligating oligonucleotide

<400> SEQUENCE: 68
cctgcaggaa gcttgcggcc gcggatcc                                      28

<210> SEQ ID NO 69
<211> LENGTH: 36
<212> TYPE: DNA
<213> ORGANISM: Artificial Sequence
<220> FEATURE:
<223> OTHER INFORMATION: Description of Artificial Sequence: Ligating oligonucleotide

<400> SEQUENCE: 69
tcgacctgca ggaagcttgc ggccgcggat ccagct                             36

<210> SEQ ID NO 70
<211> LENGTH: 28
<212> TYPE: DNA
<213> ORGANISM: Artificial Sequence
<220> FEATURE:
<223> OTHER INFORMATION: Description of Artificial Sequence: Ligating oligonucleotide

<400> SEQUENCE: 70
ggatccgcgg ccgcaagctt cctgcagg                                      28

<210> SEQ ID NO 71
<211> LENGTH: 39
<212> TYPE: DNA
<213> ORGANISM: Artificial Sequence
<220> FEATURE:
<223> OTHER INFORMATION: Description of Artificial Sequence: Ligating oligonucleotide

<400> SEQUENCE: 71
gatcacctgc aggaagcttg cggccgcgga tccaatgca                          39

<210> SEQ ID NO 72
<211> LENGTH: 31
<212> TYPE: DNA
<213> ORGANISM: Artificial Sequence
<220> FEATURE:
<223> OTHER INFORMATION: Description of Artificial Sequence: Ligating oligonucleotide

<400> SEQUENCE: 72
ttggatccgc ggccgcaagc ttcctgcagg t                                  31

<210> SEQ ID NO 73
<211> LENGTH: 2013
<212> TYPE: DNA
<213> ORGANISM: Arabidopsis thaliana

<400> SEQUENCE: 73
atgcccctta ttcatcggaa aaagccgacg gagaaaccat cgacgccgcc atctgaagag    60
gtggtgcacg atgaggattc gcaaaagaaa ccacacgaat cttccaaatc ccaccataag   120
aaatcgaacg gaggagggaa gtggtcgtgc atcgattctt gttgttggtt cattgggtgt   180

-continued

```
gtgtgtgtaa cctggtggtt tcttctcttc ctttacaacg caatgcctgc gagcttccct    240
cagtatgtaa cggagcgaat cacgggtcct ttgcctgacc cgcccggtgt taagctcaaa    300
aaagaaggtc ttaaggcgaa acatcctgtt gtcttcattc ctgggattgt caccggtggg    360
ctcgagcttt gggaaggcaa acaatgcgct gatggtttat ttagaaaacg tttgtggggt    420
ggaacttttg gtgaagtcta caaaaggcct ctatgttggg tggaacacat gtcacttgac    480
aatgaaactg ggttggatcc agctggtatt agagttcgag ctgtatcagg actcgtggct    540
gctgactact tgctcctgg ctactttgtc tgggcagtgc tgattgctaa ccttgcacat    600
attggatatg aagagaaaaa tatgtacatg gctgcatatg actggcggct ttcgtttcag    660
aacacagagg tacgtgatca gactcttagc cgtatgaaaa gtaatataga gttgatggtt    720
tctaccaacg gtgaaaaaa agcagttata gttccgcatt ccatgggggt cttgtatttt    780
ctacatttta tgaagtgggt tgaggcacca gctcctctgg gtggcggggg tgggccagat    840
tggtgtgcaa agtatattaa ggcggtgatg aacattggtg gaccatttct tggtgttcca    900
aaagctgttg cagggctttt ctctgctgaa gcaaaggatg ttgcagttgc cagagcgatt    960
gccccaggat tcttagacac cgatatattt agacttcaga ccttgcagca tgtaatgaga   1020
atgacacgca catgggactc aacaatgtct atgttaccga agggaggtga cacgatatgg   1080
ggcgggcttg attggtcacc ggagaaaggc cacacctgtt gtgggaaaaa gcaaaagaac   1140
aacgaaactt gtggtgaagc aggtgaaaac ggagtttcca agaaaagtcc tgttaactat   1200
ggaaggatga tatcttttgg gaaagaagta gcagaggctg cgccatctga gattaataat   1260
attgattttc gaggtgctgt caaaggtcag agtatcccaa atcacacctg tcgtgacgtg   1320
tggacagagt accatgacat gggaattgct gggatcaaag ctatcgctga gtataaggtc   1380
tacactgctg gtgaagctat agatctacta cattatgttg ctcctaagat gatggcgcgt   1440
ggtgccgctc atttctctta tggaattgct gatgatttgg atgacaccaa gtatcaagat   1500
cccaaatact ggtcaaatcc gttagagaca aaattaccga atgctcctga gatggaaatc   1560
tactcattat acggagtggg gataccaacg gaacagagca tacgtataca agcttaaccag   1620 tctcccgaca gttgcatccc ctttcagata ttcacttctg ctcacgagga ggacgaagat   1680
agctgtctga agcaggagt ttacaatgtg gatggggat aaacagtacc cgtcctaagt   1740
gccgggtaca tgtgtgcaaa agcgtggcgt ggcaagacaa gattcaaccc ttccggaatc   1800
aagacttata taagagaata caatcactct ccgccggcta acctgttgga agggcgcggg   1860
acgcagagtg gtgcccatgt tgatatcatg ggaaactttg ctttgatcga agatatcatg   1920
agggttgccg ccggaggtaa cgggtctgat ataggacatg accaggtcca ctctggcata   1980
tttgaatggt cggagcgtat tgacctgaag ctg                                 2013
```

<210> SEQ ID NO 74
<211> LENGTH: 671
<212> TYPE: PRT
<213> ORGANISM: Arabidopsis thaliana

<400> SEQUENCE: 74

Met Pro Leu Ile His Arg Lys Lys Pro Thr Glu Lys Pro Ser Thr Pro
1               5                   10                  15

Pro Ser Glu Glu Val Val His Asp Glu Asp Ser Gln Lys Lys Pro His
            20                  25                  30

Glu Ser Ser Lys Ser His His Lys Lys Ser Asn Gly Gly Gly Lys Trp
        35                  40                  45

-continued

```
Ser Cys Ile Asp Ser Cys Cys Trp Phe Ile Gly Cys Val Cys Val Thr
    50              55                  60
Trp Trp Phe Leu Leu Phe Leu Tyr Asn Ala Met Pro Ala Ser Phe Pro
65              70                  75                  80
Gln Tyr Val Thr Glu Arg Ile Thr Gly Pro Leu Pro Asp Pro Pro Gly
                85                  90                  95
Val Lys Leu Lys Lys Glu Gly Leu Lys Ala Lys His Pro Val Val Phe
                100                 105                 110
Ile Pro Gly Ile Val Thr Gly Gly Leu Glu Leu Trp Glu Gly Lys Gln
            115                 120                 125
Cys Ala Asp Gly Leu Phe Arg Lys Arg Leu Trp Gly Thr Phe Gly
    130                 135                 140
Glu Val Tyr Lys Arg Pro Leu Cys Trp Val Glu His Met Ser Leu Asp
145                 150                 155                 160
Asn Glu Thr Gly Leu Asp Pro Ala Gly Ile Arg Val Arg Ala Val Ser
                165                 170                 175
Gly Leu Val Ala Ala Asp Tyr Phe Ala Pro Gly Tyr Phe Val Trp Ala
                180                 185                 190
Val Leu Ile Ala Asn Leu Ala His Ile Gly Tyr Glu Glu Lys Asn Met
            195                 200                 205
Tyr Met Ala Ala Tyr Asp Trp Arg Leu Ser Phe Gln Asn Thr Glu Val
    210                 215                 220
Arg Asp Gln Thr Leu Ser Arg Met Lys Ser Asn Ile Glu Leu Met Val
225                 230                 235                 240
Ser Thr Asn Gly Gly Lys Lys Ala Val Ile Val Pro His Ser Met Gly
                245                 250                 255
Val Leu Tyr Phe Leu His Phe Met Lys Trp Val Glu Ala Pro Ala Pro
                260                 265                 270
Leu Gly Gly Gly Gly Pro Asp Trp Cys Ala Lys Tyr Ile Lys Ala
    275                 280                 285
Val Met Asn Ile Gly Gly Pro Phe Leu Gly Val Pro Lys Ala Val Ala
    290                 295                 300
Gly Leu Phe Ser Ala Glu Ala Lys Asp Val Ala Val Ala Arg Ala Ile
305                 310                 315                 320
Ala Pro Gly Phe Leu Asp Thr Asp Ile Phe Arg Leu Gln Thr Leu Gln
                325                 330                 335
His Val Met Arg Met Thr Arg Thr Trp Asp Ser Thr Met Ser Met Leu
                340                 345                 350
Pro Lys Gly Gly Asp Thr Ile Trp Gly Gly Leu Asp Trp Ser Pro Glu
                355                 360                 365
Lys Gly His Thr Cys Cys Gly Lys Lys Gln Lys Asn Asn Glu Thr Cys
    370                 375                 380
Gly Glu Ala Gly Glu Asn Gly Val Ser Lys Ser Pro Val Asn Tyr
385                 390                 395                 400
Gly Arg Met Ile Ser Phe Gly Lys Glu Val Ala Glu Ala Pro Ser
                405                 410                 415
Glu Ile Asn Asn Ile Asp Phe Arg Gly Ala Val Lys Gly Gln Ser Ile
                420                 425                 430
Pro Asn His Thr Cys Arg Asp Val Trp Thr Glu Tyr His Asp Met Gly
            435                 440                 445
Ile Ala Gly Ile Lys Ala Ile Ala Glu Tyr Lys Val Tyr Thr Ala Gly
450                 455                 460
```

```
Glu Ala Ile Asp Leu Leu His Tyr Val Ala Pro Lys Met Met Ala Arg
465                 470                 475                 480
Gly Ala Ala His Phe Ser Tyr Gly Ile Ala Asp Leu Asp Asp Thr
            485                 490                 495
Lys Tyr Gln Asp Pro Lys Tyr Trp Ser Asn Pro Leu Glu Thr Lys Leu
            500                 505                 510
Pro Asn Ala Pro Glu Met Glu Ile Tyr Ser Leu Tyr Gly Val Gly Ile
            515                 520                 525
Pro Thr Glu Arg Ala Tyr Val Tyr Lys Leu Asn Gln Ser Pro Asp Ser
        530                 535                 540
Cys Ile Pro Phe Gln Ile Phe Thr Ser Ala His Glu Glu Asp Glu Asp
545                 550                 555                 560
Ser Cys Leu Lys Ala Gly Val Tyr Asn Val Asp Gly Asp Glu Thr Val
                565                 570                 575
Pro Val Leu Ser Ala Gly Tyr Met Cys Ala Lys Ala Trp Arg Gly Lys
            580                 585                 590
Thr Arg Phe Asn Pro Ser Gly Ile Lys Thr Tyr Ile Arg Glu Tyr Asn
            595                 600                 605
His Ser Pro Pro Ala Asn Leu Leu Glu Gly Arg Gly Thr Gln Ser Gly
        610                 615                 620
Ala His Val Asp Ile Met Gly Asn Phe Ala Leu Ile Glu Asp Ile Met
625                 630                 635                 640
Arg Val Ala Ala Gly Gly Asn Gly Ser Asp Ile Gly His Asp Gln Val
                645                 650                 655
His Ser Gly Ile Phe Glu Trp Ser Glu Arg Ile Asp Leu Lys Leu
            660                 665                 670

<210> SEQ ID NO 75
<211> LENGTH: 1986
<212> TYPE: DNA
<213> ORGANISM: Saccharomyces cerevisiae

<400> SEQUENCE: 75
atgggcacac tgtttcgaag aaatgtccag aaccaaaaga gtgattctga tgaaaacaat      60
aaaggggttt ctgttcataa caagcgagag agcagaaacc acattcatca tcaacaggga     120
ttaggccata agagaagaag gggtattagt ggcagtgcaa aaagaaatga gcgtggcaaa     180
gatttcgaca ggaaaagaga cgggaacggt agaaaacgtt ggagagattc cagaagactg     240
attttcattc ttggtgcatt cttaggtgta cttttgccgt ttagctttgg cgcttatcat     300
gttcataata gcgatagcga cttgtttgac aactttgtaa attttgattc acttaaagtg     360
tatttggatg attggaaaga tgttctccca caagtataa gttcgtttat tgatgatatt     420
caggctggta actactccac atcttcttta gatgatctca gtgaaaattt tgccgttggt     480
aaacaactct acgtgattaa taatatcgag gccaaacatc ctgttgtaat ggttcctggt     540
gtcatttcta cgggaattga agctgggga gttattggag acgatgagtg cgatagttct     600
gcgcattttc gtaaacggct gtggggaagt ttttacatgc tgagaacaat ggttatggat     660
aaagtttgtt ggttgaaaca tgtaatgtta gatcctgaaa caggtctgga cccaccgaac     720
tttacgctac gtgcagcaca gggcttcgaa tcaactgatt atttcatcgc agggtattgg     780
atttggaaca aagttttcca aaatctggga gtaattggct atgaacccaa taaaatgacg     840
agtgctgcgt atgattggag gcttgcatat ttagatctag aaagacgcga taggtacttt     900
acgaagctaa aggaacaaat cgaactgttt catcaattga gtggtgaaaa agtttgttta     960
```

-continued

```
attggacatt ctatgggttc tcagattatc ttttacttta tgaaatgggt cgaggctgaa    1020
ggccctcttt acggtaatgg tggtcgtggc tgggttaacg aacacataga ttcattcatt    1080
aatgcagcag ggacgcttct gggcgctcca aaggcagttc cagctctaat tagtggtgaa    1140
atgaaagata ccattcaatt aaatacgtta gccatgtatg gtttggaaaa gttcttctca    1200
agaattgaga gagtaaaaat gttacaaacg tggggtggta taccatcaat gctaccaaag    1260
ggagaagagg tcatttgggg ggatatgaag tcatcttcag aggatgcatt gaataacaac    1320
actgacacat acggcaattt cattcgattt gaaaggaata cgagcgatgc tttcaacaaa    1380
aatttgacaa tgaaagacgc cattaacatg acattatcga tatcacctga atggctccaa    1440
agaagagtac atgagcagta ctcgttcggc tattccaaga atgaagaaga gttaagaaaa    1500
aatgagctac accacaagca ctggtcgaat ccaatggaag taccacttcc agaagctccc    1560
cacatgaaaa tctattgtat atacggggtg aacaacccaa ctgaaagggc atatgtatat    1620
aaggaagagg atgactcctc tgctctgaat ttgaccatcg actacgaaag caagcaacct    1680
gtattcctca ccgaggggga cggaaccgtt ccgctcgtgg cgcattcaat gtgtcacaaa    1740
tgggcccagg gtgcttcacc gtacaaccct gccggaatta acgttactat tgtggaaatg    1800
aaacaccagc cagatcgatt tgatatacgt ggtggagcaa aaagcgccga acacgtagac    1860
atcctcggca gcgcggagtt gaacgattac atcttgaaaa ttgcaagcgg taatggcgat    1920
ctcgtcgagc cacgccaatt gtctaatttg agccagtggg tttctcagat gcccttccca    1980
atgtaa                                                                1986
```

<210> SEQ ID NO 76
<211> LENGTH: 661
<212> TYPE: PRT
<213> ORGANISM: Saccharomyces cerevisiae

<400> SEQUENCE: 76

```
Met Gly Thr Leu Phe Arg Arg Asn Val Gln Asn Gln Lys Ser Asp Ser
  1               5                  10                  15

Asp Glu Asn Asn Lys Gly Gly Ser Val His Asn Lys Arg Glu Ser Arg
             20                  25                  30

Asn His Ile His His Gln Gln Gly Leu Gly His Lys Arg Arg Arg Gly
         35                  40                  45

Ile Ser Gly Ser Ala Lys Arg Asn Glu Arg Gly Lys Asp Phe Asp Arg
     50                  55                  60

Lys Arg Asp Gly Asn Gly Arg Lys Arg Trp Arg Asp Ser Arg Arg Leu
 65                  70                  75                  80

Ile Phe Ile Leu Gly Ala Phe Leu Gly Val Leu Leu Pro Phe Ser Phe
                 85                  90                  95

Gly Ala Tyr His Val His Asn Ser Asp Ser Asp Leu Phe Asp Asn Phe
            100                 105                 110

Val Asn Phe Asp Ser Leu Lys Val Tyr Leu Asp Asp Trp Lys Asp Val
        115                 120                 125

Leu Pro Gln Gly Ile Ser Ser Phe Ile Asp Asp Ile Gln Ala Gly Asn
    130                 135                 140

Tyr Ser Thr Ser Ser Leu Asp Asp Leu Ser Glu Asn Phe Ala Val Gly
145                 150                 155                 160

Lys Gln Leu Leu Arg Asp Tyr Asn Ile Glu Ala Lys His Pro Val Val
                165                 170                 175

Met Val Pro Gly Val Ile Ser Thr Gly Ile Glu Ser Trp Gly Val Ile
            180                 185                 190
```

-continued

Gly Asp Asp Glu Cys Asp Ser Ser Ala His Phe Arg Lys Arg Leu Trp
        195                 200                 205

Gly Ser Phe Tyr Met Leu Arg Thr Met Val Met Asp Lys Val Cys Trp
        210                 215                 220

Leu Lys His Val Met Leu Asp Pro Glu Thr Gly Leu Asp Pro Pro Asn
225                 230                 235                 240

Phe Thr Leu Arg Ala Ala Gln Gly Phe Glu Ser Thr Asp Tyr Phe Ile
                245                 250                 255

Ala Gly Tyr Trp Ile Trp Asn Lys Val Phe Gln Asn Leu Gly Val Ile
                260                 265                 270

Gly Tyr Glu Pro Asn Lys Met Thr Ser Ala Ala Tyr Asp Trp Arg Leu
        275                 280                 285

Ala Tyr Leu Asp Leu Glu Arg Asp Arg Tyr Phe Thr Lys Leu Lys
        290                 295                 300

Glu Gln Ile Glu Leu Phe His Gln Leu Ser Gly Glu Lys Val Cys Leu
305                 310                 315                 320

Ile Gly His Ser Met Gly Ser Gln Ile Ile Phe Tyr Phe Met Lys Trp
                325                 330                 335

Val Glu Ala Glu Gly Pro Leu Tyr Gly Asn Gly Gly Arg Gly Trp Val
                340                 345                 350

Asn Glu His Ile Asp Ser Phe Ile Asn Ala Ala Gly Thr Leu Leu Gly
                355                 360                 365

Ala Pro Lys Ala Val Pro Ala Leu Ile Ser Gly Glu Met Lys Asp Thr
        370                 375                 380

Ile Gln Leu Asn Thr Leu Ala Met Tyr Gly Leu Glu Lys Phe Phe Ser
385                 390                 395                 400

Arg Ile Glu Arg Val Lys Met Leu Gln Thr Trp Gly Ile Pro Ser
                405                 410                 415

Met Leu Pro Lys Gly Glu Val Ile Trp Gly Asp Met Lys Ser Ser
                420                 425                 430

Ser Glu Asp Ala Leu Asn Asn Asn Thr Asp Thr Tyr Gly Asn Phe Ile
        435                 440                 445

Arg Phe Glu Arg Asn Thr Ser Asp Ala Phe Asn Lys Asn Leu Thr Met
        450                 455                 460

Lys Asp Ala Ile Asn Met Thr Leu Ser Ile Ser Pro Glu Trp Leu Gln
465                 470                 475                 480

Arg Arg Val His Glu Gln Tyr Ser Phe Gly Tyr Ser Lys Asn Glu Glu
                485                 490                 495

Glu Leu Arg Lys Asn Glu Leu His His Lys His Trp Ser Asn Pro Met
                500                 505                 510

Glu Val Pro Leu Pro Glu Ala Pro His Met Lys Ile Tyr Cys Ile Tyr
        515                 520                 525

Gly Val Asn Asn Pro Thr Glu Arg Ala Tyr Val Tyr Lys Glu Asp
        530                 535                 540

Asp Ser Ser Ala Leu Asn Leu Thr Ile Asp Tyr Glu Ser Lys Gln Pro
545                 550                 555                 560

Val Phe Leu Thr Glu Gly Asp Gly Thr Val Pro Leu Val Ala His Ser
                565                 570                 575

Met Cys His Lys Trp Ala Gln Gly Ala Ser Pro Tyr Asn Pro Ala Gly
                580                 585                 590

Ile Asn Val Thr Ile Val Glu Met Lys His Gln Pro Asp Arg Phe Asp
                595                 600                 605

-continued

```
Ile Arg Gly Gly Ala Lys Ser Ala Glu His Val Asp Ile Leu Gly Ser
    610                 615                 620
Ala Glu Leu Asn Asp Tyr Ile Leu Lys Ile Ala Ser Gly Asn Gly Asp
625                 630                 635                 640
Leu Val Glu Pro Arg Gln Leu Ser Asn Leu Ser Gln Trp Val Ser Gln
                645                 650                 655
Met Pro Phe Pro Met
            660

<210> SEQ ID NO 77
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide primer

<400> SEQUENCE: 77
ggatccgcgg ccgcacaatg ccccttattc atcgg                              35

<210> SEQ ID NO 78
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide primer

<400> SEQUENCE: 78
ggatcccctg caggtcacag cttcaggtca atacg                              35

<210> SEQ ID NO 79
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide primer

<400> SEQUENCE: 79
ggatccgcgg ccgcacaatg ggcacactct ttcgaag                            37

<210> SEQ ID NO 80
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide primer

<400> SEQUENCE: 80
ggatcccctg caggttacat tgggcacact gtttcgaag                          39
```